(12) United States Patent
LeCursi et al.

(10) Patent No.: US 10,874,539 B2
(45) Date of Patent: Dec. 29, 2020

(54) CONFIGURABLE ORTHOSIS AND METHOD OF DEFINITIVE ORTHOTIC DESIGN, FABRICATION AND VALIDATION

(71) Applicant: Becker Orthopedic Appliance Company, Troy, MI (US)

(72) Inventors: Nicholas LeCursi, Troy, MI (US); Beatrice Janka, Troy, MI (US); Alec Bashore, Sterling Heights, MI (US); Nicholas Zalinski, Macomb Township, MI (US); Rodger Broick, Romeo, MI (US); James Campbell, Clarkston, MI (US)

(73) Assignee: Becker Orthopedic Appliance Company, Troy, MI (US)

( * ) Notice: Subject to any disclaimer, the term of this patent is extended or adjusted under 35 U.S.C. 154(b) by 648 days.

(21) Appl. No.: 15/587,816

(22) Filed: May 5, 2017

(65) Prior Publication Data

US 2018/0318122 A1 Nov. 8, 2018

(51) Int. Cl.
*A61F 5/01* (2006.01)
*B29C 64/386* (2017.01)
(Continued)

(52) U.S. Cl.
CPC .......... *A61F 5/0127* (2013.01); *A61B 5/1077* (2013.01); *A61F 5/0102* (2013.01);
(Continued)

(58) Field of Classification Search
CPC ............ A61F 5/0127; A61F 2005/0158; A61F 2005/0137; A61F 2005/0167;
(Continued)

(56) References Cited

U.S. PATENT DOCUMENTS 4,672,955 A 6/1987 Cooper
4,819,660 A 4/1989 Smith
(Continued)

FOREIGN PATENT DOCUMENTS

DE 19941368 A1 4/2001
WO WO2008033852 A2 3/2008
(Continued)

OTHER PUBLICATIONS

International Searching Authority (ISA/US); International Search Report and Written Opinion of the ISA; US PCT/US2018/031178, International Filing Date May 4, 2018; dated Jul. 27, 2018, 24 pages.
(Continued)

*Primary Examiner* — Ophelia A Hawthorne
(74) *Attorney, Agent, or Firm* — Hinshaw & Culbertson LLP

(57) ABSTRACT

Configurable orthoses having a high degree of independent adjustability of various parameters are provided. In the example of a rehabilitation-evaluation ankle-foot orthosis (REAFO), these parameters may include calf band antero-posterior, height, width, sagittal tilt, coronal tilt, and medio-lateral displacement adjustments; mediolateral displacement adjustments of a supramalleolar support; heel width/stirrup separation adjustment; and sagittal active joint resistance and neutral angle adjustments. Calf band mediolateral displacement adjustment may be provided by a lockable four-bar pivoting frame linkage of the REAFO. In one aspect, the configurable orthosis is used in conjunction with a plastically deformable precursor member to facilitate the design and manufacture of a definitive orthosis customized for a particular patient. In another aspect, the orthosis communicatively transmits limb shape data to either a positive shape receiver apparatus or a CAD/CAM apparatus, to facilitate design and manufacture of a definitive orthosis.

33 Claims, 20 Drawing Sheets

(51) Int. Cl.
  *B33Y 80/00* (2015.01)
  *A61B 5/107* (2006.01)
  *B29C 39/02* (2006.01)
  *B29C 39/44* (2006.01)
  *B29L 31/00* (2006.01)

(52) U.S. Cl.
  CPC .............. *B29C 39/02* (2013.01); *B29C 39/44* (2013.01); *B29C 64/386* (2017.08); *B33Y 80/00* (2014.12); *A61F 2005/0137* (2013.01); *A61F 2005/0158* (2013.01); *A61F 2005/0167* (2013.01); *B29L 2031/753* (2013.01)

(58) Field of Classification Search
  CPC ...... A61F 5/0102; A61F 5/0585; A61F 13/04; A61H 3/00; A61H 1/024; A61H 2201/1207; A61H 2201/1246; A61H 2201/164; A61H 2201/1642; A61H 2201/165; A61H 2201/1652; A61H 2201/1676; A61H 2201/5007; A61H 1/0237
  See application file for complete search history.

(56) References Cited

U.S. PATENT DOCUMENTS

| | | |
|---|---|---|
| 5,044,360 A | 9/1991 | Janke |
| 5,076,871 A | 12/1991 | Frye et al. |
| 5,176,623 A | 1/1993 | Stetman et al. |
| 5,445,603 A | 8/1995 | Wilkerson |
| 5,470,622 A | 11/1995 | Rinde et al. |
| 5,486,157 A | 1/1996 | DiBenedetto |
| 5,571,077 A | 11/1996 | Klearman et al. |
| 5,571,078 A | 11/1996 | Malewicz |
| 5,651,743 A | 7/1997 | Stephan et al. |
| 5,698,055 A | 12/1997 | Benkoczy |
| 5,788,618 A | 8/1998 | Joutras |
| 5,902,259 A | 5/1999 | Wilkerson |
| 6,036,665 A | 3/2000 | Towsley |
| 6,056,712 A | 5/2000 | Grim |
| 6,129,690 A | 10/2000 | Hamlin et al. |
| 6,299,587 B1 | 10/2001 | Birmingham |
| 6,319,218 B1 | 11/2001 | Birmingham |
| 6,488,644 B1 | 12/2002 | Ostrom et al. |
| 6,752,774 B2 | 6/2004 | Townsend et al. |
| 6,821,638 B2 | 11/2004 | Obeshaw |
| 6,824,523 B2 | 11/2004 | Carlson |
| 6,860,864 B2 | 3/2005 | Meyer |
| 7,018,350 B2 | 3/2006 | Hinshon |
| 7,101,346 B1 | 9/2006 | Davis |
| 7,201,728 B2 | 4/2007 | Sterling |
| 7,691,076 B2 | 4/2010 | Castro |
| 7,740,602 B2 | 6/2010 | Christensen |
| 7,766,851 B2 | 8/2010 | Lindh et al. |
| 7,846,120 B2 | 12/2010 | DeToro et al. |
| 7,878,993 B2 | 2/2011 | Agrawal et al. |
| 7,886,618 B2 | 2/2011 | Macomber et al. |
| 7,922,774 B2 | 4/2011 | Macomber et al. |
| 8,075,633 B2 | 12/2011 | Herr et al. |
| 8,114,042 B2 | 2/2012 | Klotz et al. |
| 8,215,186 B2 | 7/2012 | Macomber et al. |
| 8,221,341 B1 | 7/2012 | Al-Oboudi |
| 8,241,739 B2 | 8/2012 | Schonfeld et al. |
| 8,251,935 B2 | 8/2012 | Bonutti et al. |
| 8,287,477 B1 | 10/2012 | Herr et al. |
| 8,298,294 B2 | 10/2012 | Kaltenborn et al. |
| 8,313,451 B2 | 11/2012 | Cox |
| 8,376,971 B1 | 2/2013 | Herr et al. |
| 8,382,694 B2 | 2/2013 | Wenger |
| 8,409,297 B2 | 4/2013 | Boone et al. |
| 8,444,583 B2 | 5/2013 | Phillips |
| 8,454,543 B2 | 6/2013 | Skahan et al. |
| 8,465,445 B2 | 6/2013 | George |
| 8,474,666 B2 | 7/2013 | Vitillo et al. |
| 8,480,604 B2 | 7/2013 | Messer |
| 8,480,760 B2 | 7/2013 | Hansen et al. |
| 8,491,511 B2 | 7/2013 | Gentz et al. |
| 8,500,668 B2 | 8/2013 | Siegler et al. |
| 8,512,269 B1 | 8/2013 | Stano et al. |
| 8,512,415 B2 | 8/2013 | Herr et al. |
| 8,538,570 B2 | 9/2013 | Stanhope et al. |
| 8,551,029 B1 | 10/2013 | Herr et al. |
| 8,551,169 B2 | 10/2013 | Fitz et al. |
| D693,471 S | 11/2013 | Bradshaw |
| 8,578,634 B2 | 11/2013 | Nguyen et al. |
| 8,585,708 B2 | 11/2013 | Fitz et al. |
| 8,591,446 B2 | 11/2013 | Helm |
| 8,597,369 B2 | 12/2013 | Hansen et al. |
| 8,696,764 B2 | 4/2014 | Hansen et al. |
| 8,728,171 B2 | 5/2014 | Kaltenborn et al. |
| 8,734,371 B2 | 5/2014 | Robertson |
| D706,942 S | 6/2014 | Bradshaw |
| 8,753,275 B2 | 6/2014 | Najafi et al. |
| D708,343 S | 7/2014 | Davis |
| 8,771,211 B2 | 7/2014 | Bonutti et al. |
| 8,784,502 B2 | 7/2014 | Macomber et al. |
| 8,790,282 B2 | 7/2014 | Jung et al. |
| 8,808,214 B2 | 8/2014 | Herr et al. |
| 8,814,868 B2 | 8/2014 | Janna et al. |
| 8,821,588 B2 | 9/2014 | Latour |
| 8,828,095 B2 | 9/2014 | Mosler et al. |
| 8,838,263 B2 | 9/2014 | Sivak et al. |
| 8,852,292 B2 | 10/2014 | Ragnarsdottir et al. |
| 8,858,482 B2 | 10/2014 | Ingimundarson et al. |
| 8,870,801 B2 | 10/2014 | Tomiyama et al. |
| 9,278,014 B2 | 3/2016 | Macomber et al. |
| 9,295,576 B2 | 3/2016 | Boone et al. |
| 2001/0051780 A1 | 12/2001 | Birmingham |
| 2002/0183674 A1 | 12/2002 | Castillo |
| 2002/0188238 A1 | 12/2002 | Townsend et al. |
| 2003/0060745 A1 | 3/2003 | Seligman |
| 2003/0219578 A1 | 11/2003 | Jones et al. |
| 2004/0015112 A1 | 1/2004 | Salutterback et al. |
| 2005/0096576 A1 | 5/2005 | Castro |
| 2006/0206043 A1 | 9/2006 | Yakimovich et al. |
| 2007/0049858 A1 | 3/2007 | Agrawal et al. |
| 2007/0219475 A1 | 9/2007 | Bonutti et al. |
| 2008/0255489 A1 | 10/2008 | Genda et al. |
| 2010/0076346 A1 | 3/2010 | Abel et al. |
| 2010/0125231 A1 | 5/2010 | Knecht |
| 2010/0185301 A1 | 7/2010 | Hansen et al. |
| 2010/0275338 A1 | 11/2010 | Hyde et al. |
| 2011/0201983 A1 | 8/2011 | Swanson |
| 2011/0251539 A1 | 10/2011 | Gentz et al. |
| 2012/0016493 A1 | 1/2012 | Hansen et al. |
| 2012/0209163 A1 | 8/2012 | Phillips |
| 2013/0006386 A1 | 1/2013 | Hansen et al. |
| 2013/0220645 A1 | 8/2013 | Kirkpatrick et al. |
| 2013/0245524 A1 | 9/2013 | Schofield |
| 2013/0281898 A1 | 10/2013 | Cropper et al. |
| 2013/0296754 A1 | 11/2013 | Campbell et al. |
| 2013/0345611 A1 | 12/2013 | Phillips |
| 2014/0066829 A1 | 3/2014 | Drillio |
| 2014/0088729 A1 | 3/2014 | Herr et al. |
| 2014/0180185 A1 | 6/2014 | Zachariasen |
| 2014/0276304 A1 | 9/2014 | Dollar et al. |
| 2014/0276316 A1 | 9/2014 | Bradshaw |
| 2015/0216701 A1 | 8/2015 | Semsch et al. |
| 2015/0216703 A1 | 8/2015 | Madden |

FOREIGN PATENT DOCUMENTS

| | | |
|---|---|---|
| WO | WO2010006340 A1 | 1/2010 |
| WO | 2010070364 A1 | 6/2010 |
| WO | WO2012050908 A2 | 4/2012 |
| WO | WO2012174623 A1 | 12/2012 |

OTHER PUBLICATIONS

Lecursi, Nicholas, "Sports Shoes and Orthoses," DeLee & Drez's Orthopaedic Sports Medicine Principles and Practice, Fourth Edition 2015, pp. 1385-1386, El Sevier Saunders, Philadelphia, PA.

(56) References Cited

OTHER PUBLICATIONS

Becker Orthopedic Appliance Company, Stride Family Catalog, pp. 1-19, Jun. 2012.
International Searching Authority (ISA/US), PCT/US2018/031178, International Filing Date May 4, 2018; International Search Report and Written Opinion of the ISA; dated Jul. 27, 2018, 24 pages.

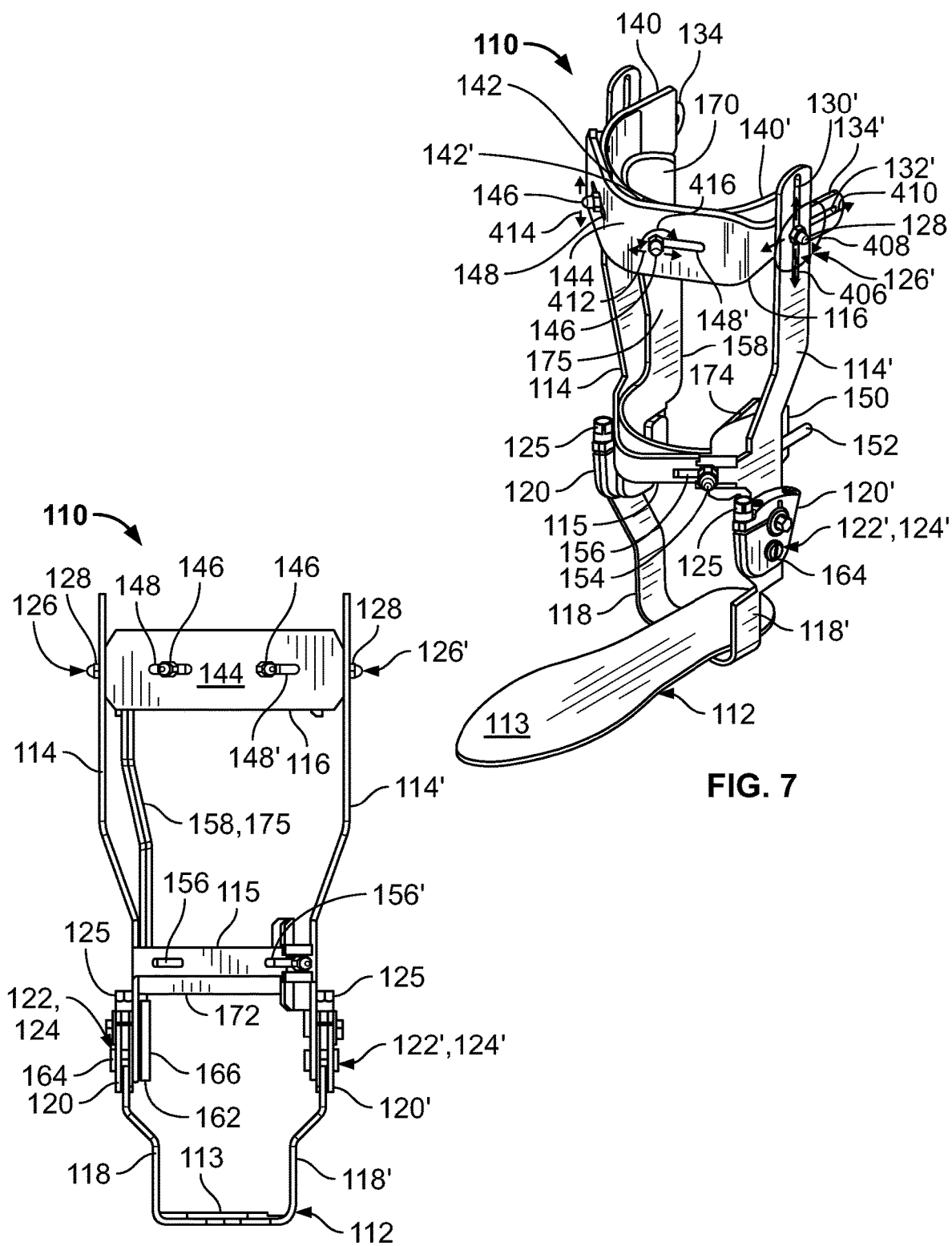

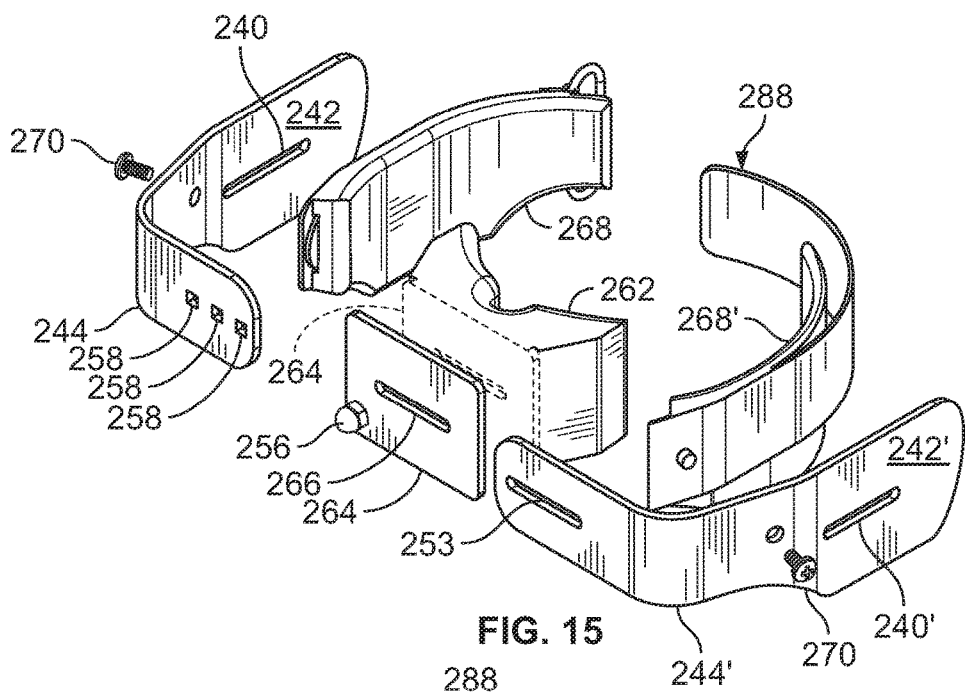
FIG. 15
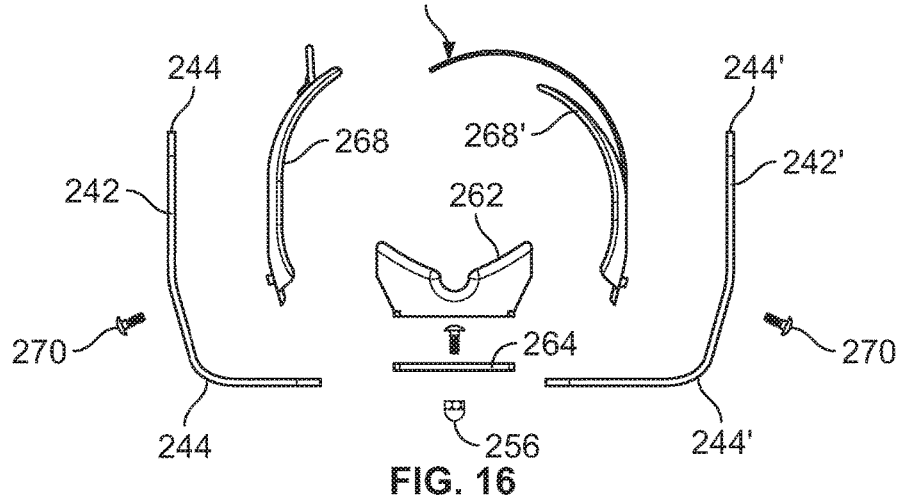
FIG. 16
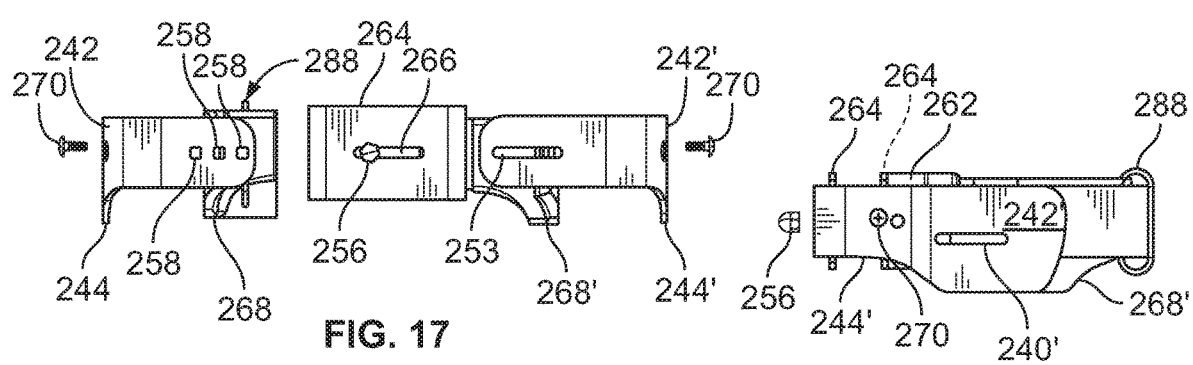
FIG. 17
FIG. 18

CONFIGURABLE ORTHOSIS AND METHOD OF DEFINITIVE ORTHOTIC DESIGN, FABRICATION AND VALIDATION

FIELD OF THE INVENTION

The present invention relates to orthotic devices and to methods of delivering orthotic care. More particularly, the present invention relates to a prefabricated rehabilitation/evaluation orthosis and the use thereof to determine patient candidacy for orthotic treatment, design a definitive orthosis using the rehabilitation/evaluation orthosis, and validate the orthotic design before fabrication, fitting and delivery of a definitive orthosis.

BACKGROUND

Customary Orthotic Practice: Description

The field of orthotic practice has traditionally relied upon the skill and experience of the clinician to determine patient candidacy for orthotic treatment, translate clinical indicators into the orthotic design and anticipate the benefit of the orthotic device to the patient prior to fabrication and fitting.

The role of the orthotist and customary care practiced by the orthotist is in the treatment of patients with musculoskeletal pathology. The customary practice of orthotics does not typically utilize direct means to evaluate the benefit of an orthotic device prior to fabrication and fitting of the definitive orthotic device. One reason that this is not typically done is due to the challenge of orthotically influencing the musculoskeletal system without creating the definitive, custom orthosis.

The foot and ankle complex is comprised of a chain of oblique, partially constrained, polyarticular synovial joints. These joints connect the body segments and are articulated by the neuromotor system. The muscles that attach to these segments may cross one or more joints and may influence one, two, three or more articulations. The shape of the bones, ligamentous constraints and muscle attachments influence the action of the muscles. The influence of the neuromotor system that mobilizes the body segments is further complicated by the effect of weight bearing posture. The neuromotor system controls the coordinated or in neuromotor pathology, uncoordinated motor action.

Orthoses function by applying torque across anatomical joints and altering pressure distribution to influence joint torque by direct and indirect mechanical action. Direct orthotic action implies that the anatomical joint is enclosed by the orthotic device; indirect action implies that the influence is through manipulation of the ground reaction vector on non-encompassed joint moments. Indirect orthotic action may also be inferred though biomechanical coupling of muscles acting across multiple body segments.

Evidence suggests that orthoses may elicit a beneficial change in biomechanical variables, not just through the tactile feel of the orthosis (though that may be influential as well), but also by altering joint moments through eliciting a beneficial motor response by the patient to the orthotic stimulus. With neuromotor pathology and an uncoordinated response to the orthotic stimulus, the prediction of the beneficial impact of the orthotic device on biomechanical variables is significantly complicated. Anticipating an uncoordinated response to the orthotic stimulus is very challenging in clinical practice and also may impact the mechanical action of the orthosis.

It is because of this level of complexity and the nature of the mechanical and neuromotor orthotic influence that the design and evaluation of an orthosis prior to fabrication and fitting of the definitive orthosis is so complicated. The clinician makes a "best guess" as to the effectiveness of the orthotic design by utilizing clinical assessment, history of care and experience. But often the orthotic device design will require "adjustment" to its shape, alignment, stiffness or compressibility to refine the design during fitting and optimization. If the orthosis as fabricated is close enough to the optimal design, then it can be adjusted to suit the needs of the patient. If, however, the design is not close enough to optimal, the device may need to be refabricated, need exists for a more efficient method and a system for designing, evaluating and producing a definitive orthosis for a patient. Existing Apparatus and Process for Determining and Evaluating the Orthotic Design Prior to Fabrication 1. Diagnostic Check Orthosis If a definitive orthosis is to be fabricated using materials or methods difficult to adjust following fabrication, the clinician may order the fabrication of what is called a diagnostic check orthosis (DCO). A DCO is fabricated using transparent material that is easily adjusted to the shape of the patient's limb. The material is drape molded over the cast used for custom fabrication of the definitive orthosis. This type of evaluation tool is used to evaluate the contour of the preliminary design with respect to the non-weight bearing limb, but is typically not suitable for functional evaluation. This lack of functional evaluation may be a significant limitation due to the complex nature of orthotic postural support. If effectively used however, the DCO may help to improve gross aspects of the orthotic fit, and can reduce the likelihood of re-fabrication of the definitive orthosis. Production of a DCO is, however, time consuming, requires multiple visits for the patient and is expensive.

2. Evaluation Orthosis

Another type of evaluation tool that is sometimes used in orthotic practice is the Evaluation Orthosis. This type of orthotic device is a pre-fabricated design, intended for functional evaluation of gross aspects of orthotic support that are being considered for the definitive orthotic design.

The PreStride® knee-ankle-foot orthosis (KAFO) is one type of evaluation orthosis manufactured by Becker Orthopedic Appliance Company. This device is used to determine patient candidacy for orthotic treatment using stance control knee orthoses. The device is a generically shaped open frame device, adjustable to suit a variety of limb shapes and patients. The primary orthotic support element is resistance to knee flexion provided by the stance control knee component of the orthosis and therefore the open frame design is suitable for functional evaluation unlike the DCO. However, the intimacy of fit is poor and not suitable for direct translation into the definitive shaped orthosis.

The PreStride® KAFO device does not significantly influence planes of motion or anatomical joints other than the knee in the sagittal plane. This may significantly simplify the orthotic design of the evaluation orthosis. Triplane influence over the foot and ankle complex may require greater intimacy of fit and precise adjustment of orthotic supportive elements than single plane influence over the knee, however. To help explain the challenges inherent in designing a pre-fabricated evaluation orthosis suitable for functional evaluation of orthotic designs intended to influence the foot and ankle, it is helpful to describe orthoses in terms of the type of support they are intended to provide.

3. Elements of Lower Extremity Orthotic Support and Orthotic Design

A lower extremity orthosis may be described in terms of a set of orthotic supportive elements with unique, anatomically shaped features designed specifically to address a patient's biomechanical deficits. A lower extremity orthosis that is intended to support only the foot and ankle may be described by ten or more such elements. Anecdotal evidence suggests that these elements are not equally influential, their influence on biomechanical function may depend on their relative shape and stiffness with respect to the weightbearing limb, and the neuromotor response to the orthotic stimulus. In the treatment of chronic stroke for example, the patient's limb posture may tend toward spastic equinovarus. Because this posture is often the result of the position of the hindfoot, orthotic supportive elements acting at the sagittal and coronal hindfoot may be more influential than other supportive elements in managing posture and function of the foot. These hindfoot elements are described by the free body diagrams in FIGS. 2A, 2B, 3A, and 3B.

The supportive elements in a lower extremity orthosis (a/k/a "ankle-foot orthosis" or "AFO") may include, for example, three point bending principally in the coronal plane at the subtalar joint resisting hindfoot inversion and/or resisting hindfoot eversion (FIGS. 2A, 2B), and three point bending principally in the sagittal plane at the talotibial joint resisting ankle dorsiflexion and/or resisting ankle plantarflexion (FIGS. 3A, 3B). In each of FIGS. 2A-2B, presented as static free-body diagrams of schematically illustrated lower extremity orthosis components, coronal three point bending support is indicated in terms of an upper reaction force 502, central reaction force 500, and lower reaction force (LF) 504 transmitted to upper and/or lower orthosis components 508, 506 by a wearer's lower leg and foot (not shown), and a wearer's weight W 510 and slightly offset ground reaction force 512 (equal to the wearer's weight) are also indicated. In FIGS. 2A-2B, the medial side is on the left and the lateral side is on the right. In the static free body diagrams shown in FIGS. 3A-3B, dorsiflexion resistive and plantarflexion resistive three point bending support, respectively, are similarly indicated by an upper reaction force 502, central reaction force 500, and lower reaction force 504. In FIG. 3A, lower reaction force (LF) 504, which urges lower orthosis component 506 to pivot in dorsiflexion, is the portion of a total ground reaction force W concentrated at the ball of the wearer's foot, while the remaining ground reaction force 514 (W-LF) is indicated as concentrated at the wearer's heel. In FIG. 3B, on the other hand, a portion of the wearer's weight W that has shifted to the ball of the wearer's foot is expressed as lower reaction force (LF) 504, urging lower orthosis component 506 to pivot in plantarflexion, while the portion of the wearer's weight that remains concentrated at the wearer's heel is expressed as 510 (W-LF).

Numerous other supportive elements distal to the ankle may also be included, such as those elements resisting foot pronation, such as by increased arch support, three point bending to resist midfoot abduction, and/or forefoot wedging to accommodate forefoot inversion or eversion; or those elements resisting complex postures like excessive supination or pronation, such as by decreased arch support, increased arch support or, three point bending to resist midfoot adduction/abduction, and/or forefoot wedging to accommodate forefoot eversion (not shown).

The provision of supportive elements to provide three-point bending principally in the sagittal plane or principally in the coronal plane at the hindfoot is only one facet of the orthotic design necessary to effectively evaluate its influence and to translate it into a definitive orthosis. As stated previously, the orthotic influence may be considered some combination of direct or indirect mechanical action and the elicited neuro-motor response.

The relative shape of the orthosis with respect to the weight bearing limb in the sagittal, coronal and transverse planes appears to play an important role, as does the shape and relationship between the supportive elements. The transition between elements also may play a significant role. In addition, the structure, stiffness of the orthotic shell materials, and compressibility of any interface materials also may play a significant role in determining the level of orthotic support.

4. Design and Fabrication of the Definitive Orthosis

To fabricate the definitive orthosis, the shape of the patient's limb is captured by any suitable technique, including, for example, by tracing the limb on a sheet of paper or by molding the limb using a casting technique. The shape of the limb may also be captured by optical scan, though this method limits the ability of the practitioner to sense the resistance of the limb to corrections in posture during the shape capture operation; an essential aspect of determining the orthotic design.

Using the casting technique, when the clinician casts the patient as the first step in the orthotic design process she palpates the limb to identify bony prominences, and positions the limb to get a 'feel' for the resistance of the limb to postural realignment. This positioning of the limb is typically done with the patient on the exam table so that the practitioner can most effectively sense and position the limb as the first step in the orthotic design process. Whether the position of the limb or shape of the mold is optimal cannot, however, be explicitly determined prior to fabrication of the definitive orthosis. The performance of the orthotic design is intuitively anticipated within a margin of error for adjustment of the definitive orthosis. To help better inform clinical intuition, the practitioner may evaluate the patient's postural and tactile response to trials conducted using discrete orthotic support elements. These elements may take the form of prefabricated orthoses, the patient's former orthosis (if one exists), a diagnostic check orthosis, or a discrete postural support element like an arch support.

There exists, however, a need for improvements to the evaluation of the effect of these supportive elements as relates to the orthotic design functional impact on the patient as well as apparatus and methods to translate the details of that design into the definitive orthosis with high confidence in an improved and successful clinical outcome.

SUMMARY OF THE INVENTION

Several aspects of configurable orthoses, methods of orthotic treatment using configurable orthoses, and methods of making custom/definitive orthoses using configurable orthoses, are summarized in this section.

Configurable Orthosis with Plastically Deformable Precursor Member

According to an aspect of the invention, a configurable orthosis is provided, comprising a first link; a second link; a plastically deformable precursor member; and a first support member. A "plastically deformable member" means a member that, when subjected to stresses falling within a significant range of stresses that a clinician can readily apply by hand, either directly or via movement of a support member of a rehabilitation-evaluation orthosis (REO), undergoes "plastic deformation", that is, deformation (a/k/a "strain") that is "irreversible" in the sense of not reversing itself when the stress is removed, without the member fracturing. In engineering, plastic deformation of a member is said to occur at stresses greater than or equal to the "yield strength" of the member, (below which any strain will be elastic, i.e., self-reversing), and less than the "ultimate strength" of the member, at which the member will fracture. Thus, a "plastically deformable member" may further be understood as a member that, when taking account of its shape, has a low enough yield strength to permit a clinician to apply forces manually to produce stresses above the yield strength at a desired region of the member, while at the same time having sufficient ductility, that is, an ultimate strength sufficiently greater than its yield strength, to provide a significant margin of safety against fracturing when being manipulated in the plastic deformation range. In some cases, the member may have a thinner cross section in regions where plastic deformation is desired and a thicker cross section in adjacent regions where shape retention is desired. The scope of "plastically deformable precursor member" is not limited to members of any particular material or class of material, but only requires that it possess the physical properties specified above. Suitable materials for a deformable precursor member may include, without limitation, malleable/ductile metals such as aluminum or steel, soft thermoplastics, or suitable composite materials such as described in more detail below for "conformable composite (bar) precursors" or "CBar" precursors.

In addition, the modifier "precursor" will not be understood to imply that the plastically deformable precursor member is necessarily "curable" to form a "definitive" (or "custom" or "permanent" member). Rather, "precursor" simply refers to the member performing a function in a REO that may be performed by a corresponding definitive member of a subsequently designed and manufactured definitive orthosis. Such a definitive member of the definitive orthosis may be, but need not be, the precursor member itself incorporated into the definitive orthosis, with or without first permanently altering its physical properties to become more elastic and/or more rigid (such as by application of heat, chemical doping, or otherwise) after plastic deformation to the desired shape (i.e., "curing"). In other instances, the definitive member may not include the precursor member, even in a cured state, but may instead be made using the precursor member (or using support members of the REO used to deform or brace deformed portions of the precursor member) as a mold, tool or observational guide.

For ease of reference, the terms "plastically deformable" and "plastically deform" will be understood to refer not only to a portion or portions of the precursor member whose shape is altered by the local application of manipulative stresses, but also to portions of the precursor member that are deflected or displaced relative to other portions of the precursor member, without themselves incurring stresses or shape change. For example, a bending deformation of a local portion of the precursor member may change an angle between remote portions of the precursor member and/or draw those remote portions closer together or farther apart, without reshaping those remote portions. Examples of a "plastically deformable precursor member" are also referred to herein as a "conformable composite bar precursor", or "CBar precursor", for short.

The first link is configured to extend along a lateral side of a first limb segment of a limb of a user when the orthosis is worn by the user. It will be understood that the terms "first link" and "second link" do not necessarily imply that the orthosis permits relative articulation thereof. The links may instead be lockably and releasably constrained in a fixed relation to each other, or they may be portions of the same stiff or rigid member. The terms "lateral side" and "contralateral side" are used herein to refer generically and broadly to generally opposite sides of the user's limb segment, generally spaced apart in a direction parallel to an axis of articulation of a user's joint supported by the orthosis. The term "lateral" is not intended in the more specific technical sense of "outer" or "opposite of medial (inner)", nor to exclude "anterior"/"front" or "posterior"/"rear" or any other particular side, except where expressly indicated or clearly implied by context. The second link is configured to extend along a lateral side of a second limb segment of the user's limb when the orthosis is worn by the user, the user's second limb segment joined to the user's first limb segment by a physiological joint of the user that articulates about at least a first physiological joint axis, the second link being connected to the first link proximate to the first physiological joint axis at a lateral side of the physiological joint, the lateral side of the user's second limb segment being adjacent said lateral side of the user's first limb segment.

The plastically deformable precursor member is removably affixed to a member of the orthosis, such as the first link, to facilitate deformation thereof to provide customized benefits to a patient wearing the configurable orthosis. In the case of a rehabilitation-evaluation ankle-foot orthosis (RE-AFO), the precursor member is advantageously attached to a component of the orthosis, if any, which pivots with the user's lower leg, thus keeping contact surfaces of the precursor member aligned with corresponding contact portions of the user's lower leg as the orthosis and the user's lower leg and ankle articulate together. Furthermore, an attachment point for the precursor member should be spaced away from the user's lower leg, preferably disposed over an area of the user's lower leg where direct contact support is not needed, and sufficiently displaced from areas of the user's lower leg where direct contact support is needed, to permit deflection of those areas toward the contact portions of the user's lower leg.

The precursor member includes a first contact surface, the first support member being movably connected to the first link for movement to a fixed first support member adjustment position relative to the first link, to engage and deform the precursor member and to move said first contact surface into contact with a first contact portion of the user's first limb segment, when the orthosis is worn by the user. The adjustment position is selected from a range of adjustment positions, typically varying in at least one degree of freedom, which may be in one or more lines of translation and/or one or more axes of rotation. In this manner, the first contact surface of the precursor member is configured to transmit an aligning force to said first contact portion of the user's first limb segment to urge or restrain a first articulation of the user's first limb segment about the first physiological joint axis relative to the user's second limb segment.

For example, the first support member may be a generally flat plate or an angled or curved band, typically made of a stiff material such as a metal (e.g., steel, aluminum, titanium, or a suitable alloy), carbon fiber, a hard plastic (e.g., polypropylene or a copolymer), or similar. The first contact surface may be part of the first support member; that is, the first support member itself may be configured to contact the first contact portion of the user's first limb segment when the orthosis is worn. Alternatively or additionally, the first support member may be configured to carry, support, or brace a separate contact member. The contact member may, for example, be a flexible member (such as referred to throughout as a "strap") elastically deformable member (such as a type of member referred to throughout as a "pad") or a plastically deformable member (i.e., "conformable"

member, such as a type of member referred to throughout as a "conformable composite precursor" or "CBar precursor") member, or a portion thereof, against the first contact portion of the user's first limb segment when the orthosis is worn.

The first support member may support, carry, or brace multiple contact members for transmission of multiple aligning forces to multiple contact portions of the user's first limb segment, such as when a calf band component carries a pretibial pad for transmitting a posterior alignment force to urge a user's lower leg to pivot rearwardly in the sagittal plane to effect plantarflexion of the user's foot; mediolateral pads to urge a user's lower leg to pivot medially or laterally in a coronal plane to correct or adapt to a user's ankle inversion or eversion; and a rear strap for transmitting an anterior alignment force to urge a user's lower leg to pivot forwardly in the sagittal plane to effect dorsiflexion. The first support member may be connected to the first link for pivotal and/or linear movement as appropriate, to facilitate adjustment to a desired position relative to the first contact portion of a particular user's first limb segment.

In an embodiment, the configurable orthosis with plastically deformable precursor member further comprises an orthotic joint component. The orthotic joint component may, for example, include an orthotic joint, a biasing component, and a lockable alignment joint. The orthotic joint connects one of the first link and the second link for pivotal movement relative to the joint component about an orthotic joint axis approximately aligned with the first physiological joint axis when the orthosis is worn by the user. The biasing component is configured to produce a biasing torque to urge said one of the first link and the second link to articulate relative to the joint component link in a biased pivoting direction about the orthotic joint when an angular orientation of said one of the first link and the second link relative to the joint component is within an active angular range within which the biasing component is engaged. The lockable alignment joint connects the other of the first link and the second link for pivotal movement of the other link to a lockable angular orientation relative to the joint component about an alignment joint axis parallel to the orthotic joint axis, to determine a neutral angular orientation of the first link relative to the second link toward which the biasing component biases said one of the first link and the second link.

Significantly, the effect of such neutral angle adjustment is "felt" by the first contact portion of the wearer's first limb segment as rotation of a neutral position of the first contact surface of the precursor member about the alignment joint axis. Thus, when the freedom of movement of the first support member includes a component tangential to pivotal movement of the first link about the alignment joint axis, the angle of the wearer's first limb segment corresponding to the neutral angular orientation of the first link depends on the selected adjustment position of the first support member. Preferably, the first support member is adjusted to align the first limb segment, or a predominant bone thereof, parallel to the first link, when the orthosis is worn by the user and the first contact portion of the first limb segment contacts the first contact surface of the precursor member. In this manner, provided that an axis of the first link extends at least approximately through the orthotic joint, and the orthotic joint is at least approximately aligned with the physiological joint, the user's first limb segment and the first link will remain at least approximately parallel as they rotate in concert.

Preferably, said orthotic joint axis and said alignment joint axis comprise the same axis. This permits the neutral alignment of the first link to be adjusted while maintaining an orientation of its axis extending through the orthotic joint axis, facilitating parallel alignment of the first link with the user's first limb segment throughout a range of orthotic joint articulation.

The orthosis may further include a first contralateral link aligned with a contralateral side of the users first limb segment generally opposite to the lateral side of the user's first limb segment and a second contralateral link aligned with a contralateral side of the user's second limb segment generally opposite to the lateral side of the user's second limb segment, the contralateral side of the user's second limb segment being adjacent the contralateral side of the user's first limb segment. A contralateral orthotic joint component may be connected between the first contralateral link and the second contralateral link to permit pivotal movement of the first contralateral link relative to the second contralateral link about the orthotic joint axis referred to above.

When the orthosis includes contralateral links (i.e., is of a "double-upright" type construction), the first support member may, for example, be a lateral connecting member configured to join the first link in fixed relation to the lateral connecting member and to the first contralateral link, and the first contact portion of the user's first limb segment may be comprised in a front side of the user's first limb segment disposed between said lateral and contralateral sides. When the lateral connecting member is a calf band of a rehabilitation-evaluation ankle-foot orthosis (REAFO), the calf band may also contact, or indirectly brace, lateral and contralateral sides of the user's first limb segment (i.e., lower leg). As used generally, "front side" is an arbitrary designation of a side disposed between the lateral and contralateral sides, not necessarily corresponding to the front side of a user's body as in the case of the calf band of an REAFO.

Where the orthosis is an REAFO, the physiological joint is an ankle joint of the user, the first link and first contralateral link may be tibial shank components, the second link and second contralateral link may be stirrup uprights, the first support member may be a calf band (as noted above), configured to be disposed near an upper portion of the user's lower leg. In that case, the aligning force transmitted by the first contact surface of the precursor member tends to urge the user's lower leg to pivot rearwardly in a sagittal plane to produce plantarflexion (i.e., resist dorsiflexion) of the user's foot.

Alternatively, the "first support member" may refer to a support member of the configurable orthosis disposed at the lateral side of the user's first limb segment, when the orthosis is worn by the user, and being connected to the first link for lateral and contralateral movement relative to the first link. The first contact portion, in that case, may be comprised in the lateral side of the user's first limb segment.

For example, such a laterally positioned first support member may be a supramalleolar support of any embodiment of a of a rehabilitation-evaluation ankle-foot orthosis, or REAFO, described herein; a right or left width adjustment bar of a calf-band assembly that is mediolaterally translatable independently of an opposite-side width adjustment bar as in a second embodiment of an REAFO described herein; and, to some degree, a curved portion of a pretibial pad of a third embodiment of an REAFO described herein, the opposite sides of which are disposed to contact a portion of the lateral sides of a user's pretibial lower leg region and to urge the user's tibia/fibula toward the mediolateral center of the pretibial pad, owing to its concave rear face, the pretibial pad being independently mediolaterally translatable by loosening the same bolt that locks a calf band width adjustment.

Again, "lateral" being used in a generic sense, these supports of an REAFO may be provided as appropriate at the "lateral" (outer) "medial" (inner), or both sides of the wearer's lower leg or ankle, to supply the appropriate corrective, supportive, or adaptive constraint, restraint, or urging of a coronal plane rotation of the user's lower leg relative to the user's foot. In each of these cases, it is understood that the contact force on the respective "first contact portion" of the user's "first limb segment" is counterbalanced by forces from the REAFO acting along at least two other lines of action, at least one of them applied to the "second limb segment", to produce three-point bending about the physiological joint, as generally described above in the background section.

In other, distinct cases, a movement of one support member is met by a generally equal and opposite movement of an opposed counterpart support member, so that any change in contact force at one side is met by an opposite change in contact force at the opposite side along the same line of action, with no net bending effect, as in symmetrical adjustments of the independently adjustable right and left width adjustment bars of the second REAFO embodiment described herein, or stirrup width adjustments of the third and fourth REAFO embodiments, which are constrained to be symmetrical by a rack-and-pinion mechanism.

In another embodiment, the configurable orthosis comprises a second support member in addition to the first support member. The second support member is movably connected to the first link for movement to a fixed second support member adjustment position relative to the first link. This movement of the second support member to the second support member adjustment position is configured to engage and deform the precursor member and to move a second contact surface thereof into contact with a second contact portion of the user's first limb segment, when the orthosis is worn by the user. In turn, the second contact surface of the precursor member is configured to transmit an aligning force to said second contact portion of the user's first limb segment, to urge or restrain a second articulation of the user's first limb segment relative to the user's second limb segment. The second articulation may be an articulation about the same or a different physiologic joint axis as the first articulation. The second physiologic joint axis may, for example, be generally orthogonal to the first. In the example of an REAFO, the first support member and first precursor member contact surface may cooperate to urge or restrain a sagittal plane articulation of the user's lower leg and foot about the ankle joint, while the second support member and second precursor member contact surface cooperate to urge or restrain a coronal plane articulation of the user's lower leg and foot about the ankle joint.

In another embodiment, the first support member is connected for at least two degrees of freedom of movement relative to the first link. Said at least two degrees of freedom of movement may comprise independent translation in two non-parallel directions, as in vertical/height and anteroposterior adjustments of a REAFO calf band. Alternatively or in addition to a second translation, another degree of freedom may be rotational, such as sagittal pivoting of a REAFO calf band relative to REAFO tibial shanks. More generally, such freedoms of movement may be provided for by a first elongate slot formed in one of the first support member and the first link, a pin carried by the other of the first support member and the first link, the pin being retained in the first elongate slot to permit translation of the first support member relative to first link along a direction aligned with a length of the first elongate slot and rotation of the first support member relative to the first link about an axis of the pin; and a locking mechanism configured to selectively restrain said translation and said rotation of the first support member relative to the first link. A second translational degree of freedom may be provided by a second elongate slot formed in the other of the first support member and the first link, the pin being retained in the second elongate slot to permit translation of the first support member relative to the first link along a direction aligned with a length of the second elongate slot. With or without the second elongate slot, the pin may provide the rotational degree of freedom.

Treatment Method Using Orthosis with Plastically Deformable Precursor

According to another aspect of the invention, a rehabilitation and evaluation orthotic treatment method is provided. The method makes use of a configurable orthosis with plastically deformable precursor substantially as described above. The method comprises aligning the first link at the lateral side of the patient's first limb segment and the second link at the lateral side of the patient's second limb segment, with the precursor member attached to the first link and the first contact surface of the precursor member positioned between the first support member and the first contact portion of the patient's first limb segment, moving the first support member to the fixed first support member adjustment position to engage and deform the precursor member to move the first contact surface of the precursor member into contact with the first contact portion of the patient's first limb segment to urge or restrain said first articulation of the user's first limb segment about the first physiological joint axis, and providing the orthosis including the deformed precursor member for the patient to wear during a rehabilitation and evaluation period.

When observation of the patient during the rehabilitation and evaluation period indicates prescribing the patient a custom orthosis, the configurable rehabilitation evaluation orthosis (REO) facilitates the manufacture of the custom orthosis. The process involves removing the deformed precursor member from the first link, curing the deformed precursor member to form a non-plastically deformable cured custom orthotic member configured to be worn on the patient's first limb segment with the first contact surface in contact with the first contact portion of the patient's first limb segment; connecting the cured custom orthotic member to a second limb segment orthotic member configured to be worn on the patient's second limb segment when the cured custom orthotic member is worn on the patient's first limb segment, to form the custom orthosis; and providing the custom orthosis to the patient.

In some cases, before curing the deformed precursor member, further deformations of the precursor member may be made based on patient feedback and/or clinician observations of the patient wearing the orthosis during the rehabilitation and evaluation period. Thus, the first support member may be moved to a post-evaluation first support member adjustment position, to further deform the precursor member; so as to change the aligning force transmitted by the first contact surface of the precursor member to the first contact portion of the patient's first limb segment. Post-evaluative further deformation of the precursor member may alternatively be effected by hand. For example, if the aligning force turns out to be too great, due to the first contact surface of the precursor member encroaching too far into/against the contact portion of the limb segment, the first support member is retracted away from engagement with the precursor member, but having plastically deformed, the precursor member will not passively retreat to meet the first support member. In that case, further deformation of the precursor member may be effected by the first contact portion of the patient's first limb segment pushing the first contact surface toward reengagement with the first support member, or by the clinician manually pressing the first contact surface outwardly toward the first support member to reengage the precursor member with the first support member to make room for the patient's first limb segment to don the orthosis with the further-deformed precursor member. The initial and post-evaluation deformations of the precursor member may occur during a single office visit or a single hospital stay. Alternatively, the patient may wear the rehabilitation-evaluation orthosis home, and the patient may return for a second visit with the rehabilitation-evaluation orthosis, for a determination of whether to prescribe the patient a custom orthosis, further deform the precursor member for further evaluation, or terminate orthotic treatment.

Manufacturing System and Method Using an Orthosis Communicatively Linked to a Shape Data Receiver In accordance with another aspect of the invention, a system for the manufacture of a custom orthosis using a configurable orthosis communicatively linked to a shape data receiver apparatus is provided. The configurable orthosis comprises similar structural/mechanical components to those described above for the orthosis with plastically deformable precursor, but where the first and second support members may directly contact the user's leg to urge or resist the pivotal joint articulations as desired. In addition, the orthosis includes an electronic shape data sensor and an electronic shape data signal transmitter configured, respectively, to sense and electronically transmit a user limb shape data signal corresponding to the first support member adjustment position to the shape data receiver apparatus.

The electronic shape data sensor may comprise one or more suitable data capturing devices, which may for example include a force, torque, or pressure sensor, such as an electronic strain gauge or pressure gauge; a position or distance/displacement sensor, which may be optical, electrically resistive or capacitive; or even a photographic camera or other topographical imaging device, such as an optical or electromagnetic scanner. Accordingly, the shape data may comprise a single state parameter or collection of state parameters, which may range in complexity from a single numerical figure to a large digital image data file, for example. Simple shape data parameters representable by a single numerical figure or a small number of numerical figures may include, for example, a force torque or pressure applied by a support element to a wearer's limb, or a distance or displacement by which the support element is adjusted from a reference position to contact and/or apply a desired supportive force to the wearer's limb. Stepping up to a moderate level of complexity, a contour gauge (not shown) associated with the configurable orthosis, such as of the type comprising a number of sliding pins or the like, arrayed in one or two dimensions to capture a linear contour or two-dimensional surface contour of a portion of the wearer's limb, may capture shape data comprising a relatively large number of numerical figures, each representing a position of one of the sliding pins when positioned against the wearer's limb, which in turn corresponds to a point on a finite contour element on the surface of the wearer's limb. Alternatively, the shape data may take a still more complex form, such as a digital representation of a photographic or other topographical image, as in a bitmap (.bmp), joint photographic experts group (JPEG/.jpg) or portable network graphic (.png) file captured by a digital camera; or some other topographical image object captured by a suitable imaging device.

The shape data receiver apparatus comprises an electronic shape data signal receiver, an electronic shape data processor, and at least one shape approximating member. In response to the electronic shape data signal receiver receiving the user limb shape data signal, at the direction of the electronic shape data processor, the shape approximating member is configured to transform to a position or a shape determined by the user limb shape data signal, to approximate a position or shape of at least the first contact portion of the user's first limb segment, to facilitate the formation of a corresponding custom orthotic member around the shape receiver apparatus; conforming the custom orthotic member to a position or shape of at least a portion of the shape approximating member.

According to another aspect of the invention, a method of fabricating a custom orthosis is provided. The method uses a configurable orthosis and a shape data receiver apparatus communicatively linked to the configurable orthosis, substantially as described above. The method comprises positioning the user's limb in the configurable orthosis; moving the first support member to the first support member adjustment position; the electronic shape data sensor sensing the user limb shape data; and the electronic shape data signal transmitter transmitting the user limb shape data signal to the electronic shape data signal receiver. In response to the electronic shape data signal receiver receiving the user limb shape data signal, at the direction of the electronic shape data processor, the shape approximating member transforms to a position or a shape determined by the user limb shape data signal, to approximate a position or shape of at least the first contact portion of the user's first limb segment. A component of the custom orthosis is made to conform to at least a portion of the user limb approximating portion of the receiver apparatus shape.

In an embodiment, forming a component of the custom orthosis according to the method includes shaping the plastically deformable precursor member in engagement with the receiver apparatus to conform to at least a portion of the user limb approximating portion of the receiver apparatus shape, and curing the shaped precursor member to form a non-plastically deformable custom orthotic member; the method further comprising connecting the cured custom orthotic member to a second limb segment orthotic member configured to be worn on the user's second limb segment when the cured custom orthotic member is worn on the user's first limb segment, to form the custom orthosis.

CAD/CAM Apparatus Manufacturing System and Method

According to another aspect of the invention, a system and method of fabricating a custom orthosis using a configurable orthosis and a CAD/CAM apparatus is provided. The orthosis used in a CAD/CAM system according to this aspect preferably includes mechanical components similar to those of the orthosis communicatively linked to a shape receiver device of the above-described manufacturing system and method, as well as an electronic shape data sensor and an electronic shape data transmitter configured, respectively, to sense and directly communicate user limb shape data to a CAD/CAM apparatus, such as by electronically transmitting a user limb shape data signal. The method includes aligning the first link at the lateral side of the user's first limb segment and the second link at the lateral side of the user's second limb segment; moving the first support member the first support member adjustment position; the electronic shape data sensor sensing the user limb shape data, the electronic shape data signal transmitter transmitting the user limb shape data signal to a remotely located CAD/CAM apparatus; in response to receiving the user limb shape data signal, the CAD/CAM apparatus forming a custom orthotic member conforming to at least the first contact portion of the user's first limb segment as indicated by the user limb shape data signal.

Orthosis and Treatment Method with Limb Segment Width Adjustment

According to another aspect of the invention, an orthosis including movable limb segment width adjustment members is provided. The orthosis includes a frame configured to attach to a first limb segment and a second limb segment of a limb of a user, the user's second limb segment being joined to the user's first limb segment by a physiologic joint of the user; a first compressive support member connected to the frame to be disposed at a first side of the user's first limb segment; and a second compressive support member connected to the frame to be disposed at a second side of the user's first limb segment, the second side being generally opposite the first side and spaced apart therefrom in a lateral direction.

A "compressive support member" will be understood to mean a support member that is configured to be loaded in compression to transmit normal contact pressure in the same direction as the loading; in contrast to a strap, for example; which is primarily loaded in circumferential tension to apply radially inward normal contact pressure. A compressive support member is preferably a rigid member, composed of a metal, carbon fiber, hard plastic, or other rigid material, mechanically linked to the frame; optionally further including padding attached to the rigid member; preferably of an elastically compressible material such as a suitable rubber or foam.

The first compressive support member is movably connected to the frame for movement relative to at least a portion of the frame to a selected one of a plurality of first compressive support member lateral adjustment positions. This adjustment movement may or may not be exclusively or primarily in the lateral direction, but at least includes a component in the lateral direction, to engage a first side contact portion of the user's first limb segment when the orthosis is worn by the user. For example, the support member may be separate from the frame, with only a single point of connection thereto, as in the various supramalleolar supports described herein, and the calf band width adjustment bars of the second REAFO embodiment, so that adjustment movement of the support member is the same relative to any part of the frame. Alternatively, the support member may comprise a link of the frame or a portion of a link of the frame, so that adjustment movement of the support member changes the shape of the frame by moving a portion of the frame relative to other portions of the frame. Such is the case, for example, for the stirrup uprights of the third and fourth REAFO embodiments, which comprise portions of the stirrup/foot plate component, the latter being one of the four links of the four-bar coronal pivoting linkage constituting the frame of the third and fourth embodiments. Thus, widening or narrowing the distance between the lower ends of the stirrup uprights necessarily produces some flexing of the stirrup uprights and/or tibial shank assemblies. Any bending strain associated with such flexing is attenuated by the relatively small range of heel width adjustment compared to the combined vertical length of the stirrup shanks and tibial shank assemblies, i.e., compared to the vertical distance between the foot plate and calf band assembly.

Likewise, the second compressive support member is movably connected to the frame for movement relative to at least a portion of the frame to a selected one of a plurality of second compressive support member lateral adjustment positions, said movement including a component in said lateral direction, to engage a second side contact portion of the user's first limb segment when the orthosis is worn by the user. In this manner, the first and second compressive support member lateral adjustment positions define a lateral width clearance for retaining the user's first limb segment between the first and second compressive support members. The orthosis further includes first and second compressive support member locking mechanisms configured to at least substantially prevent displacement of the first and second compressive support members away from the other member in said lateral direction. Thus, when locked, the locking mechanisms permit the support members to grip or brace the user's first limb segment at opposite sides.

A "compressive support member locking mechanism" may be inherently comprised in a self-locking adjustment mechanism, such as a threaded rod that rotates to produce an axial translation, or an air bladder in communication with a one-way valve. Alternatively, a separate locking mechanism may be employed to lock the compressive support member in its selected adjustment position. Locking mechanisms illustrated herein are typically frictional, such as a bolt that is tightened to lock its own radial sliding movement in a slot, or a set screw that is tightened against a side of a rod to lock axial sliding of the rod in a sleeve or bushing. However, other types of locking mechanisms, such as normal contact stops, may be employed where suitable.

In an embodiment, movements of the first and second compressive support members in said transverse plane are independent of each other. Such first and second compressive support member movements are embodied, for example, in the width adjustment mechanism of the calf band assembly of the second embodiment of an REAFO described herein, wherein the respective transverse planar movements of a respective left and right width adjustment band are independent of each other. Advantageously, for a given calf width that falls between the two extremes accommodated, this permits mediolateral position adjustments to be performed by moving both support members the same distance in the same direction.

In another embodiment, said movements of the first and second compressive support members are constrained to be symmetrical about a midplane, which is perpendicular to the lateral direction and equidistant from each of the first and second compressive support members. In other words, in this embodiment, any movement of the first compressive support member will be accompanied by a movement of the second compressive support member having an equal and opposite component in the lateral direction, and a like component in any orthogonal direction, so that the position of the midplane, essentially defining a lateral position of a portion of the user's leg passively supported between the first and second compressive support members, does not change. One example of a mechanism producing such a kinematic constraint is a rack and pinion mechanism, housed in the foot plate, for adjusting the lateral positions of the stirrup uprights in the third and fourth embodiments of an REAFO described herein, wherein the same lockable pinion drives equal and opposite lateral movements of a respective rack associated with each stirrup upright. Such symmetrical movements of the first and second compressive support members may, for example, be movements in the lateral direction driven by rotating an adjustment pinion to simultaneously impart equal and opposite translational movements to each of two respective first and second tooth racks integral to said first and second compressive support members.

According to another aspect of the invention, a treatment method using the above described orthosis with limb segment width adjustment is provided. The method includes donning the configurable orthosis to a patient with a first limb segment of the patient disposed between the first and second compressive support members, moving the first compressive support member to said selected first compressive support member adjustment position to contact a first side contact portion of the patient's first limb segment, and moving the second compressive support member to said selected second compressive support member adjustment position to engage a second side contact portion of the patent's first limb segment.

Four-Bar Pivotal Frame Linkage Orthosis

According to another aspect of the invention, a four-bar frame linkage orthosis is provided, including generally parallel side links and generally parallel first limb segment and second limb segment attachment links. The four-bar pivotal frame linkage of this aspect permits a readily lockable, generally translational "swaying" adjustment of the position of a portion of a user's first limb segment in a gentle arcuate path "over" a portion of a second limb segment of the user. The arcuate path traversed by this swaying adjustment most closely approximates lateral translation of the limb segment attachment links in a range of angles closest to a rectangular configuration of the frame linkage. In particular embodiments, orthoses according to this aspect also provide equal side-link length adjustments to effect separation between limb segment attachment links, unequal side link length adjustments to effect relative tilt of the limb attachment links in the plane of articulation of the frame linkage, an active joint component as a sub-element of one of the links of the frame linkage, providing articulation in a plane perpendicular to the plane of articulation of the frame linkage, lockable adjustment of a neutral angle of such an active joint component, and particular bar components used to lock the frame linkage.

An orthosis according to this aspect comprises a frame configured to attach to a first limb segment and a second limb segment of a limb of a user, the user's second limb segment being joined to the user's first limb segment by a physiologic joint of the user. The frame comprises a first limb segment link configured to attach to an attachment portion of said first limb segment, a second limb segment link configured to attach to an attachment portion of said second limb segment, a first side link pivotally connected to the first limb segment link and to the second limb segment link at a first side of the first limb segment for pivoting of the first side link in a frontal plane about the first and second limb segment links, a second side link pivotally connected to the first limb segment link and to the second limb segment link at a second side of the first limb segment, generally opposite the first side and spaced apart therefrom in a lateral direction in said frontal plane, for pivoting of the second side link in said frontal plane about the first and second limb segment links. Thus, the first and second limb segment links and the first and second side links, collectively, constitute a pivotal four-bar frame linkage in which the first limb segment link is maintained approximately parallel to the second limb segment link and the first side link is maintained approximately parallel to the second side link.

A "parallel" pair of opposite links of the four-bar frame linkage will be understood to refer to a pair opposite links for which a line extending through "ends" of one of the pair is parallel to a line extending through "ends" of the other, where the "ends" of a link of the four-bar frame linkage are in turn defined as the locations of the two axes about which the link pivots in the frontal plane of articulation of the frame linkage, referred to above. Articulation of the four-bar frame linkage is configured to at least approximately effect translation of the first limb segment link relative to the second limb segment link in the lateral direction separating the side links (also generally corresponding to the direction of a length of each limb segment link), to produce a desired lateral displacement of the attachment portion of the user's first limb segment relative to the attachment portion of the user's second limb segment.

The first limb segment link may, for example, be a calf band or calf band assembly of an REAFO with its internal adjustments locked. The second limb segment link may, for example, be a subassembly of an REAFO including its stirrup-foot plate component, left and right sagittal joint components, and upper bar components with their respective sagittal alignments locked. Although the second limb segment link, so defined, encompasses a sagittally articulating sub-linkage, the overarching four-bar frame linkage articulates essentially in the coronal plane which is orthogonal to the sagittal plane. Articulation of the four-bar frame linkage is therefore essentially insensitive to sagittal articulation of the second limb segment link. Thus, for purposes of the four-bar frame linkage, such a second limb segment link may be treated as one link.

In an embodiment, the orthosis further includes a locking mechanism configured to selectively lock said articulation of the four-bar frame linkage.

In another embodiment, the orthosis further comprises the first and second side links including a respective side link adapter and side link extension. The adapter and extension are connected by a first lockable side link length adjustment connection, permitting relative translation of the adapter and extension to adjust a length of the respective side link extending between respective axes about which the respective side link pivots relative to the limb segment links. Such first and second side link length adjustments are embodied, for example, in the upper bar height adjustments of the third and fourth illustrated REAFO embodiments described in the detailed description hereof. The side link length adjustment connection is illustrated in those embodiments as a frictionally locking pin/bolt and slot joint, but other types of linear displacement connections are also possible, including, but not limited to other types of continuous displacement connections, such as of a turnbuckle type (with the benefit of being inherently self-locking against linear forces), and indexing displacement connections, such as may employ a ratchet mechanism or a removable pin extending through a selected one of a plurality of holes formed at different length positions in one or both of the side link adapter and side link extension.

In one example, the first and second lockable side link length adjustment connections permit equal adjustment of said first side link length and said second side link length to effect a linear displacement of said first limb segment link relative to said second limb segment link. This corresponds, for example, to a calf band height adjustment of the third and fourth REAFO embodiments. The first and second lockable side link length adjustment connections may, alternatively or additionally, permit unequal adjustment of said first side link length and said second side link length to effect a tilt of said first limb segment link relative to said second limb segment link in said frontal plane. This is embodied, for example, in the calf band coronal tilt adjustment of the third and fourth REAFO embodiments. The length adjustment connections of the third and fourth REAFO embodiments are illustrated as being independent of each other, but they could be made dependent as desired, such as to constrain the adjustments to be equal, thus facilitating height adjustment. For example, a detachable cross-bar (not shown), affixed at approximately right angles to each of the two upper bar extensions 235 when attached, may be employed during upper bar extension height adjustment to ensure a uniform calf band height adjustment, and removed as needed to permit a "sway" (mediolateral calf band) adjustment.

Preferably, the pivotal connections of the first side link and the second side link to the second limb segment are approximately disposed at opposite sides of said physiologic joint of the user along a line extending in said lateral direction, for pivotal articulation about axes generally parallel to an axis of articulation of the user's first and second limb segments about the physiological joint, so that articulation of the four-bar frame linkage approximately effects articulation of the user's first and second limb segments about said axis of articulation of the physiological joint.

In another embodiment, the second limb segment link includes a sub-linkage configured to articulate in a sagittal plane approximately perpendicular to said frontal plane and approximately parallel to said side links. Such sub-linkage articulation is provided, for example, by joint components 220, 220' of the third and fourth REAFO embodiments. The sub-linkage (or more particularly, joint components thereof) may comprise biasing components configured to bias a first sub-link of said sub-linkage to pivot in said sagittal plane in at least one pivotal direction toward a neutral sagittal alignment angle relative to a second sub-link of said sub-linkage. Still further, the sub-linkage may comprise a lockable alignment adjustment component configured to permit lockable adjustment of said sagittal alignment angle to a selected angle, as embodied, for example, in the sagittal alignment adjustment of tibial shank assemblies 214, 214' of the third and fourth REAFO embodiments, locked and unlocked by respective alignment locking bolts 225. Note that tibial shank assemblies 214, 214' encompass the respective side links of the REAFO frame linkage (upper bar component adapters 246, 246' and upper bar extensions 235, 235') and also portions of the second limb segment link thereof (upper bar components 248, 248', which are constrained to pivot sagittally with the entire respective tibial shank assembly, but coronally with the other components of the second limb segment link, i.e., joint components 220, 220' and stirrup-foot plate assembly 212).

In another embodiment, the orthosis comprises a particular locking mechanism for articulation of the frame linkage. The locking mechanism comprises at least a first sway bar connected between a first pair of opposite pivotal joints of said four-bar frame linkage, the first sway bar being pivotally connected at each of the first pair of opposite pivotal joints to each of two links of said four-bar frame linkage connected at the respective opposite pivotal joint, and the first sway bar further being slidingly connected to at least one of said first pair of opposite pivotal joints to permit a distance between said first pair of opposite pivotal joints to vary, to permit articulation of said four-bar frame linkage. The sliding connection of the first sway bar to at least one of said first pair of opposite pivotal joints is lockable (that is, if the sway bar is slidingly connected to both opposite pivotal joints, both sliding connections are lockable, and if only to one, that sliding connection is lockable) to fix a distance between said first pair of opposite pivotal joints, to prevent articulation of said four-bar frame linkage.

In another embodiment, the locking further comprises a second sway bar connected between a second pair of opposite pivotal joints of said four-bar frame linkage in a manner similar to the first. In this manner, the four-bar frame linkage is permitted to articulate only when both sway bars are permitted to slide with respect to at least one of the respective pair of opposite pivotal joints, that is, only when neither of said distances between opposite pivotal joints is fixed. In addition, while locking one sway bar is sufficient to kinematically lock the mechanism; two sway bars provide greater stiffness when both are locked. The sway bar may have a bent shape as shown in the drawings illustrating the third and fourth REAFO embodiments, thus providing greater frictional resistance to collapse of the frame linkage when unlocked, or may be a straight bar (not shown).

According to another aspect of the invention, an orthotic treatment method is provided, which uses a configurable, pivotal four-bar frame linkage type of orthosis substantially as described above. The method comprises donning the orthosis to first and second limb segments of a patient; articulating the four-bar frame linkage to produce a desired lateral displacement of an attachment portion of the patient's first limb segment relative to an attachment portion of the patient's second limb segment. The method thus facilitates configuring a REO to adjust a "sway" displacement of a retained portion of a patient's first limb segment relative to a retained portion of the patient's second limb segment, accompanied by a corresponding, generally slight, angular realignment of the patient's two limb segments.

Configurable Ankle Foot Orthosis and Orthotic Treatment Method with Plastically Deformable Precursor Member According to another aspect of the invention, a configurable ankle-foot orthosis (also referred to as a rehabilitation-evaluation ankle foot orthosis or REAFO) is provided; comprising a calf band; a left tibial shank connected to the calf band; a right tibial shank connected to the calf band; a left sagittal pivotal joint component; a right sagittal pivotal joint component; a stirrup component pivotally connected to the left tibial shank by the left joint component and to the right tibial shank by the right joint component for sagittal pivoting of the stirrup component relative to the left and right tibial shanks; a mediolaterally adjustable supramalleolar support connected to at least one of the left tibial shank, right tibial shank; and stirrup component and configured to be positioned at a left or right side of a patient's lower leg above the patient's ankle; a precursor member receiver component; and a plastically deformable precursor member configured to be removably installed in the orthosis in fixed relation to at least one of the left tibial shank and right tibial shank by connecting to the precursor member receiver component. The calf band includes a pair of mediolaterally adjustable side members defining an adjustable calf band width clearance for receiving an upper portion of a patient's lower leg; and the calf band is connected to the tibial shanks for adjustment of an anteroposterior position and a generally vertical height position relative thereto.

According to another aspect of the invention, the above-described REAFO is used in an orthotic treatment method, which includes a particular process of adjusting the REAFO to fit a patient. The method comprises retracting the calf band side members and supramalleolar support to receive a patient's lower leg in the orthosis; donning the orthosis to the patient; adjusting the anteroposterior position of the calf band to position a front portion of the calf band proximate to a front side of the patient's lower leg. With the lateral uprights positioned along the long axis or midline of the leg to afford anteroposterior alignment of the centers of pressure applied at the calf band and supramalleolar pad along the tibia and/or fibula bones, the height position of the calf band is adjusted to below a fibula neck of the patient's lower leg, and the precursor member is installed in the orthosis. In addition, with the precursor member installed, the method further comprises adjusting the calf band side members to plastically deform left and right side calf support portions of the precursor member to contact left and right side upper portions of the patient's lower leg in quiet standing; and with the patient's weight off of the orthosis, adjusting a mediolateral position of the supramalleolar support to plastically deform a supramalleolar support portion of the precursor member to draw the supramalleolar support portion to a desired position relative to the patient's lower leg, to provide desired resistance to inversion or eversion of the patient's ankle by contacting a supramalleolar contact portion of the patient's lower leg at a left or right side thereof, above the patient's ankle.

In an embodiment, the method further comprises removing the precursor member with deformed left and right side calf support portions and supramalleolar support portion from the orthosis; curing the precursor member to form a non-plastically deformable cured custom orthotic member; forming a custom orthosis including the non-plastically deformable cured custom orthotic member; and donning the custom orthosis to the patient's lower leg with the left and right side upper portions of the patient's lower leg received between the deformed left and right side calf support portions of the cured custom orthotic member, and the supramalleolar contact portion of the patient's lower leg in contact with the supramalleolar support portion of the cured custom orthotic member.

BRIEF DESCRIPTION OF THE DRAWINGS

FIG. 7 is a front-left perspective view of the rehabilitation-evaluation ankle-foot orthosis shown in FIG. 5, with the conformable composite bar precursor component attached thereto.

FIG. 8 is a front elevation view of the rehabilitation-evaluation ankle-foot orthosis as shown in FIG. 7.

FIG. 15 is an exploded perspective view of a calf band assembly of the rehabilitation-evaluation ankle-foot orthosis shown in FIG. 10, with scales omitted.

FIG. 16 is an exploded top view of the calf band assembly shown in FIG. 15.

FIG. 17 is an exploded front elevation view of the calf band assembly shown in FIG. 15.

FIG. 18 is an exploded left-side elevation view of the calf band assembly shown in FIG. 15.

DETAILED DESCRIPTION OF THE INVENTION

The present invention comprises a significant improvement in the design of a rehabilitation and evaluation orthosis (REO) as well as methodology for translating the REO design to a definitive orthotic design prior to fabrication of a permanent or long-term orthosis.

The devices described and illustrated herein are configurable rehabilitation-evaluation ankle-foot orthoses (RE-AFO) that are highly adjustable to meet the specific supportive needs of a variety of patients. The method described is also applicable to orthotic management of the lower extremity, upper extremity and spine using other REO devices designed for that purpose.

Embodiment: First REAFO

Figures 4A, 4B:
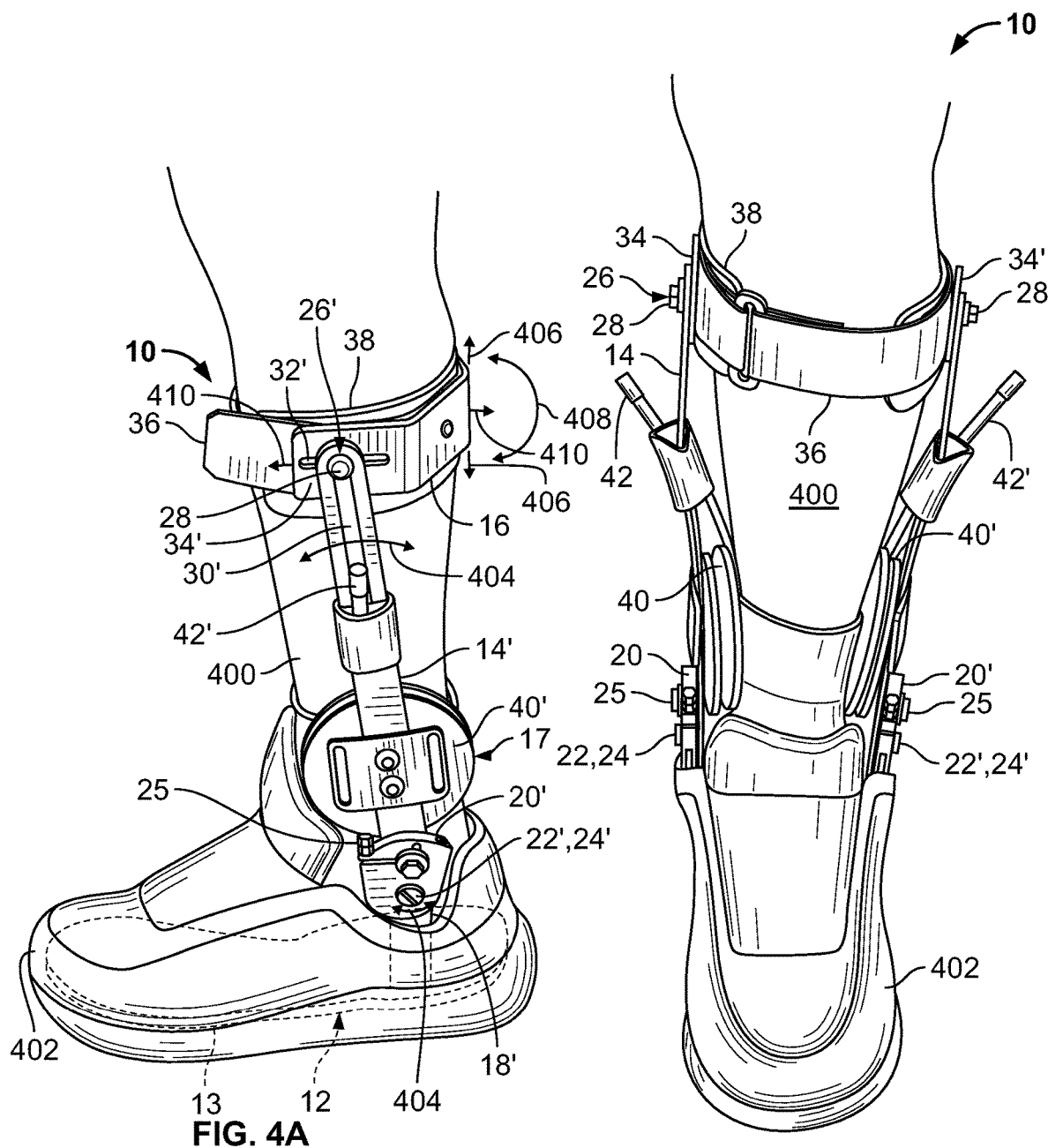
FIG. 4A is a left side perspective view of a rehabilitation-evaluation ankle-foot orthosis according to another embodiment of the invention, as worn by a patient.
FIG. 4B is a front perspective view of the rehabilitation-evaluation ankle-foot orthosis shown in FIG. 4A, as worn by a patient.

A first configurable rehabilitation-evaluation ankle-foot orthosis, embodying aspects of the present invention, is described in this section as orthosis 10 ("orthosis 10") and illustrated in FIGS. 4A-4B.

Support Sections

Orthosis 10, depicted as worn over the lower leg 400 and within the shoe 402 of a patient in FIGS. 4A and 4B, includes four principal interconnected support sections, each of which is adjustable in at least one dimension with respect to each neighboring section. These four sections are a foot plate/stirrup component 12, a right tibial shank 14, a left tibial shank 14', a calf band 16, and a supramalleolar support 17.

Tibial Shank Angle Adjustment

Foot plate/stirrup component 12 includes a foot plate 13 and a right stirrup shank (not shown) and left stirrup shank 18' attached thereto, each pivotally connected to a respective one of tibial shanks 14, 14' via a respective right or left active joint component 20, 20'. As illustrated, each active joint component 20, 20' is connected to the respective stirrup shank 18, 18' by an active pivotal joint 22, 22', through which resistive-assistive torques may be provided in dorsiflexion and plantarflexion directions in the sagittal plane. Parameters of pivotal joint 22, 22', including, for example, active angular ranges and magnitudes of dorsiflexion resistance and plantarflexion resistance torques, and any hard stop limits on angular range of motion in the sagittal plane, may be adjustable. Active joint component 20, 20' may, for example, be a staged resistance joint component with highly independent parameter adjustment, such as those described in detail in U.S. patent application Ser. No. 14/738,212 and PCT Patent Application No. PCT/US2016/037010, the entire disclosures of which are hereby expressly incorporated by reference. Active joint components embodying aspects of the afore-mentioned applications are provided by Becker Orthopedic Appliance Company. In addition, each joint component 20, 20' is connected to the respective tibial shank 14, 14' by an adjustable locking pivotal alignment joint 24, 24', lockable by a tibial shank angle alignment locking bolt 25, to provide independent neutral tibial shank angle adjustment 404 of tibial shank 14, 14' relative to the respective stirrup shank 18, 18', as also described in greater detail in the above-referenced applications. In the illustrated embodiment, pivotal alignment joint 24, 24' shares an axis with active pivotal joint 22, 22', advantageously allowing a neutral angle of tibial shanks 14, 14' relative to stirrup shanks 18, 18' to be adjusted while maintaining the alignment of tibial shanks 14, 14' with active pivotal joints 22, thus tending to maintain close sagittal plane alignment of tibial shanks 14, 14' with the wearer's tibia. Alternatively, offsetting these two axes slightly (as in other embodiments of active pivotal joints disclosed in the above-referenced patent applications) may have other advantages, including that of permitting a thinner component body in which the thicknesses of a tibial shank and a stirrup shank need not overlap.

Calf Band Height, Anteroposterior, and Sagittal Tilt Adjustments

Calf band 16 is adjustably connected at each of its mediolateral sides to a respective tibial shank 14, 14' via a respective lockable calf band-shank joint 26, 26', comprising a locking bolt 28, a generally vertical right tibial shank height adjustment slot (not shown) and left tibial shank height adjustment slot 30' formed in and generally aligned with a longitudinal axis of the respective tibial shank 14, 14', and a generally horizontal right side anteroposterior adjustment slot (not shown) and left side anteroposterior adjustment slot 32' formed in and generally aligned with a longitudinal axis of a respective right or left elongate side bar 34, 34' of calf band 16, each of height adjustment slot 30' and anteroposterior adjustment slot 32' retaining locking bolt 28 for generally sagittal rotation and translational movements of locking bolt 28 in each respective slot, when locking bolt 28 is loosened to permit such movements. Calf band-shank joints 26, 26' thus provide calf band 16 three simultaneously lockable degrees of freedom relative to tibial shanks 14, 14', namely, a generally vertical calf band height adjustment 406 generally in a longitudinal dimension of tibial shanks 14, 14', a calf band sagittal tilt adjustment 408 generally in the sagittal plane (calf band sagittal tilt adjustment 408 should be performed after tibial shank angle adjustment 404, as only the former can be performed without affecting the other) and a calf band anteroposterior adjustment 410 generally in a longitudinal dimension of side bars 34, 34' of calf band 16.

Attached to calf band 16 is a retention strap 36 configured to adjustably retain calf band 16 with desired tightness to an upper portion of lower leg 400. In addition, a suitable cushioning pad 38 may be disposed between the wearer's lower leg 400 and calf band 16, which is typically a rigid member that is disposed to extend around an upper portion of either the wearer's calf or the wearer's shin, depending on the chosen angular position of calf band 16. In this embodiment, calf band 16 is shown extending behind leg 400, around the wearer's calf, whereas in the second and third embodiments described below, analogous calf bands are shown disposed to extend forwardly around a wearer's shin (i.e., toward a distal toe end of the respective foot plate). When a rigid calf band is to be oriented to extend around and in close proximity to a wearer's upper shin, it is generally desirable to mount a conformable member between the calf band and the wearer's shin and/or to provide the calf band with integral padding, as illustrated in the below embodiments by way of example.

A calf band according to the invention may incorporate, embody, or carry other adjustable support elements not shown or described in detail herein. As a non-limiting example of one such other support element, an REAFO may include an adjustable and/or conformable patellar tendon bearing support element, associated with a calf band thereof, which may or may not be otherwise generally similar or equivalent to calf band 16 or to either of calf bands 116, 216 to be described below.

Supramalleolar Support Adjustment

Figure 1:
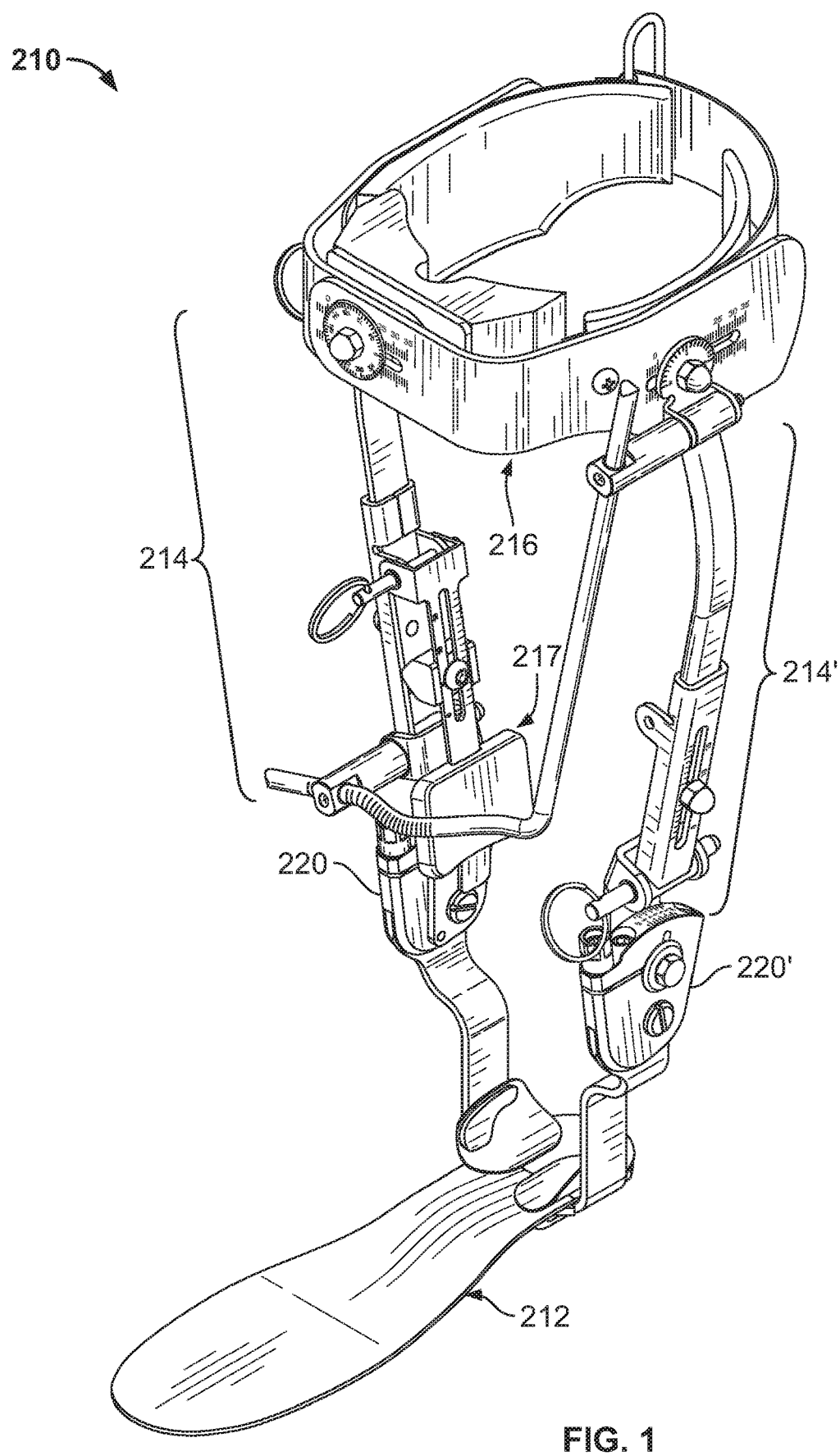
FIG. 1 is a front-left perspective view of a rehabilitation-evaluation ankle-foot orthosis according to one embodiment of the invention, with only principal support sections labeled.
Figure 2A:
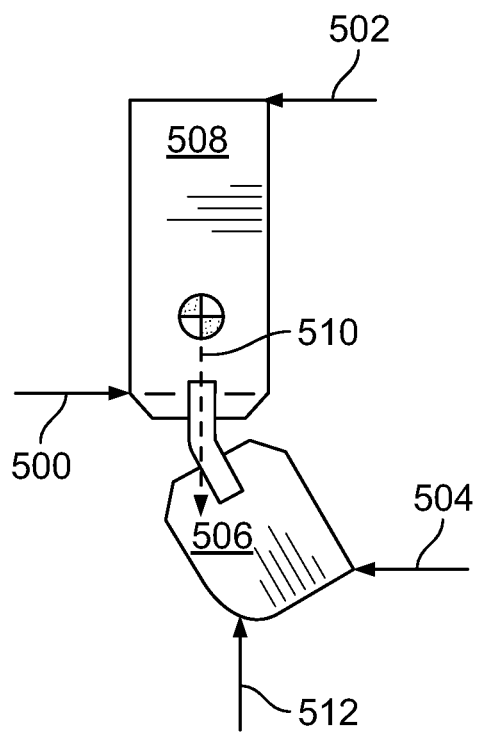
FIG. 2A is a rear-elevation schematic free body diagram of one example of forces acting on an orthosis providing three-point bending support in the coronal plane.
Figure 2B:
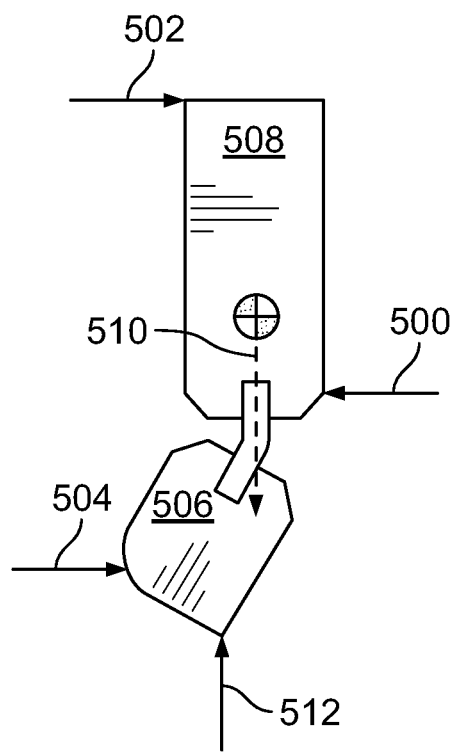
FIG. 2B is a rear-elevation schematic free body diagram of another example of forces acting on an orthosis providing three-point bending support in the coronal plane.
Figure 3A:
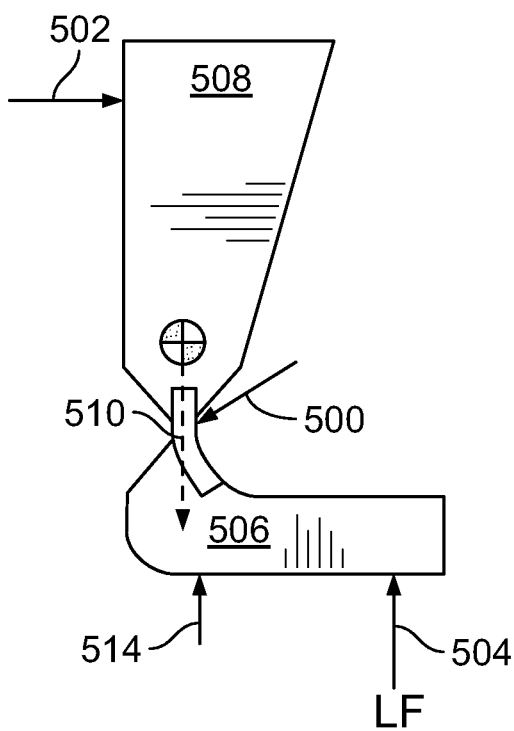
FIG. 3A is a side-elevation schematic free body diagram of three-point bending dorsiflexion forces acting on a lower-leg orthosis, which may provide active resistance thereto.
Figure 3B:
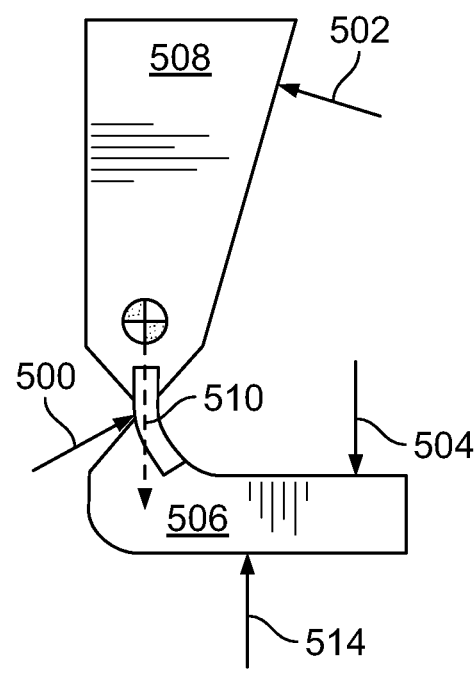
FIG. 3B is a side elevation free body diagram of three-point bending plantarflexion forces acting on a lower-leg orthosis, which may provide active resistance thereto.

At least one of tibial shanks 14, 14' is configured to carry a respective supramalleolar support 17, which tends to urge a portion of the wearers lower leg above the ankle in a medial or lateral direction. Supramalleolar support 17 comprises right and left air bladders 40, 40' in communication with valves 42, 42' for expanding air bladders 40, 40' to thereby increase a medial or lateral supporting force provided by air bladders 40, 40'. This central supporting force is the counterpart to a central reaction force 500 from a wearer's lower leg in coronal plane three-point bending support, as discussed above with reference to FIGS. 2A, 2B. In orthosis 10, an upper supporting force similarly corresponding to upper reaction force 502 is supplied by the elongate side bar 34, 34' of calf band 16 that is contralateral to the supramalleolar support supplying the central supporting force, while a lower supporting force is supplied by a lower portion of the contralateral stirrup shank 18' and/or an adjacent area of foot plate 13.

Embodiment: Second REAFO

A second configurable rehabilitation-evaluation ankle-foot orthosis, embodying aspects of the present invention, is described in this section as rehabilitation-evaluation ankle-foot orthosis 110 ("orthosis 110") and illustrated in FIGS. 5-9F.

Support Sections

Orthosis 110 includes four principal interconnected support sections, each of which is adjustable in at least one dimension with respect to each neighboring section. These four sections are a foot plate/stirrup component 112, a right tibial shank 114 and a left tibial shank 114' joined together by a supramalleolar crossbar 115, a calf band assembly 116, and a supramalleolar support 117.

Tibial Shank Angle Adjustment

Foot plate/stirrup component 112 includes a foot plate 113 and a right stirrup shank 118 and a left stirrup shank 118' attached thereto, each pivotally connected to a respective one of tibial shanks 114, 114' via a respective right or left active joint component 120, 120'. As illustrated, each active joint component 120, 120' is connected to the respective stirrup shank 118, 118' by an active pivotal joint 122, 122', through which resistive-assistive torques may be provided in dorsiflexion and plantarflexion directions in the sagittal plane. Parameters of pivotal joint 122, 122', including, for example, active angular ranges and magnitudes of dorsiflexion resistance and plantarflexion resistance torques, and any hard stop limits on angular range of motion in the sagittal plane, may be interdependently or independently adjustable. Active joint component 120, 120' may, for example, be a staged resistance joint component with highly independent parameter adjustment, such as those described in detail in U.S. patent application Ser. No. 14/738,212 and PCT Patent Application No. PCT/US2016/037010, the entire disclosures of which are hereby expressly incorporated by reference. Active joint components embodying aspects of the aforementioned applications are provided by Becker Orthopedic Appliance Company. In addition, each joint component 120, 120' is connected to the respective tibial shank 114, 114' by an adjustable locking pivotal alignment joint 124, 124', lockable by a tibial shank angle alignment locking bolt 125, to provide independent neutral tibial shank angle adjustment 404 of tibial shank 114, 114' relative to the respective stirrup shank 118, 118', as also described in greater detail in the above-referenced applications. In the illustrated embodiment, pivotal alignment joint 124, 124' shares an axis with active pivotal joint 122, 122', advantageously allowing a neutral angle of tibial shanks 114, 114' relative to stirrup shanks 118, 118' to be adjusted while maintaining the alignment of tibial shanks 114, 114' with active pivotal joint 122, 122', thus tending to maintain close sagittal plane alignment of tibial shanks 114, 114' with the wearer's tibia. Alternatively, offsetting these two axes slightly (as in other embodiments of active pivotal joints disclosed in the above-referenced patent applications) may have other advantages, including that of permitting a thinner component body in which the thicknesses of a tibial shank and a stirrup shank need not overlap.

Calf Band Height, Anteroposterior, Sagittal Tilt, Width, and Coronal Tilt Adjustments Calf band assembly 116 is adjustably connected at each of its mediolateral sides to a respective tibial shank 114, 114' via a respective lockable calf band-shank joint 126, 126', comprising a locking bolt 128, a generally vertical height adjustment slot 130, 130' formed in and generally aligned with a longitudinal axis of tibial shank 114, 114', and a generally horizontal anteroposterior adjustment slot 132, 132' formed in and generally aligned with a longitudinal axis of a respective elongate side bar 134, 134' of calf band assembly 116, each of height adjustment slot 130, 130' and anteroposterior adjustment slot 132, 132' retaining locking bolt 128 for generally sagittal rotation and translational movements of locking bolt 128 in each respective slot, when locking bolt 128 is loosened to permit such movements. Calf band-shank joints 126, 126' thus provide calf band assembly 116 three simultaneously lockable degrees of freedom relative to tibial shanks 114, 114', namely, a generally vertical calf band height adjustment 406 generally in a longitudinal dimension of tibial shanks 114, 114', a calf band sagittal tilt adjustment 408 generally in the sagittal plane (calf band sagittal tilt adjustment STA 408 should be performed after tibial shank angle adjustment 404, as only the former can be performed without affecting the other), and a calf band anteroposterior adjustment 410 generally in a longitudinal dimension of side bars 134, 134' of calf band assembly 116.

Figure 5:
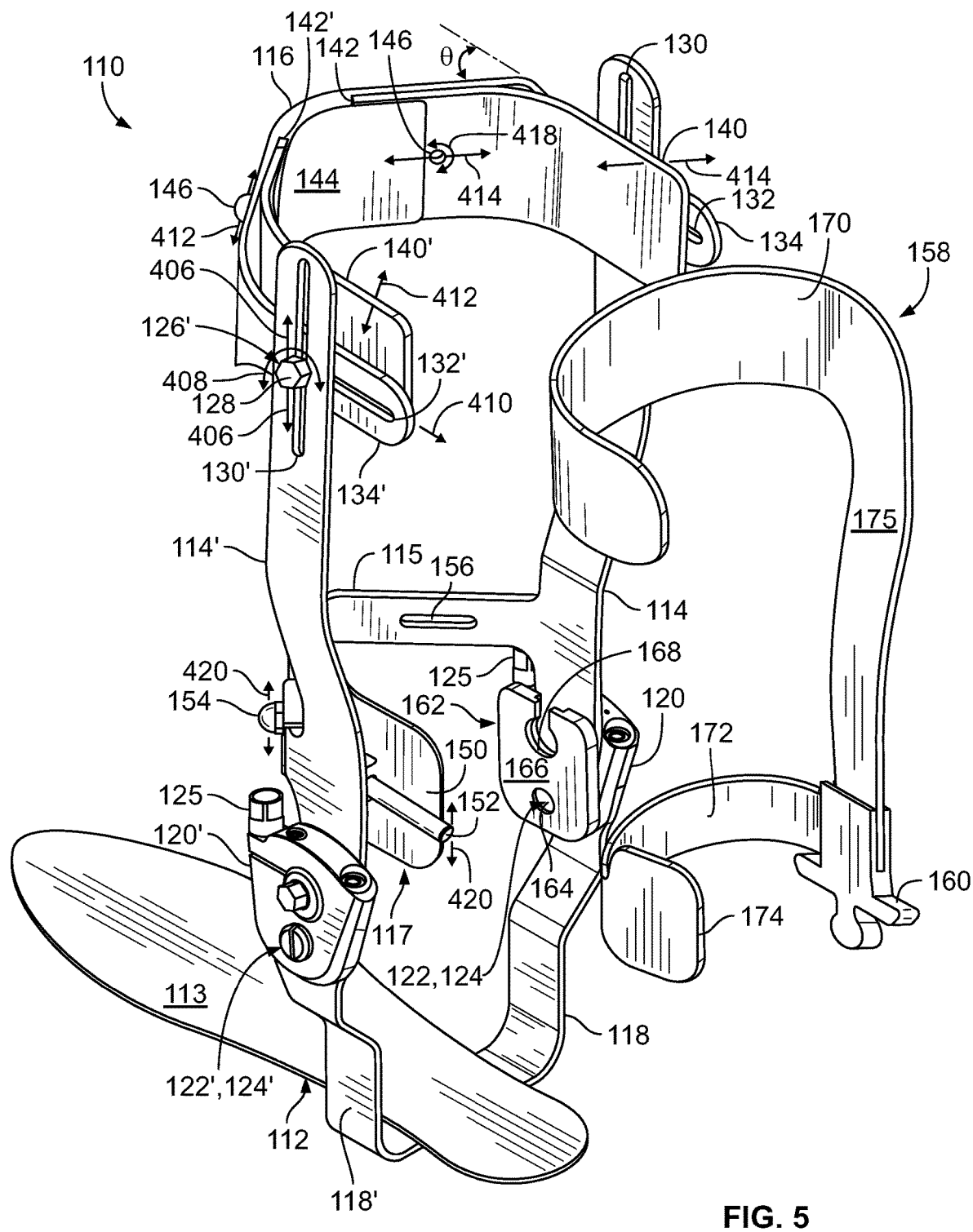
FIG. 5 is a left-rear perspective view of a rehabilitation-evaluation ankle-foot orthosis according to another embodiment, with a conformable composite bar precursor component exploded out from the orthosis.
Figure 6:
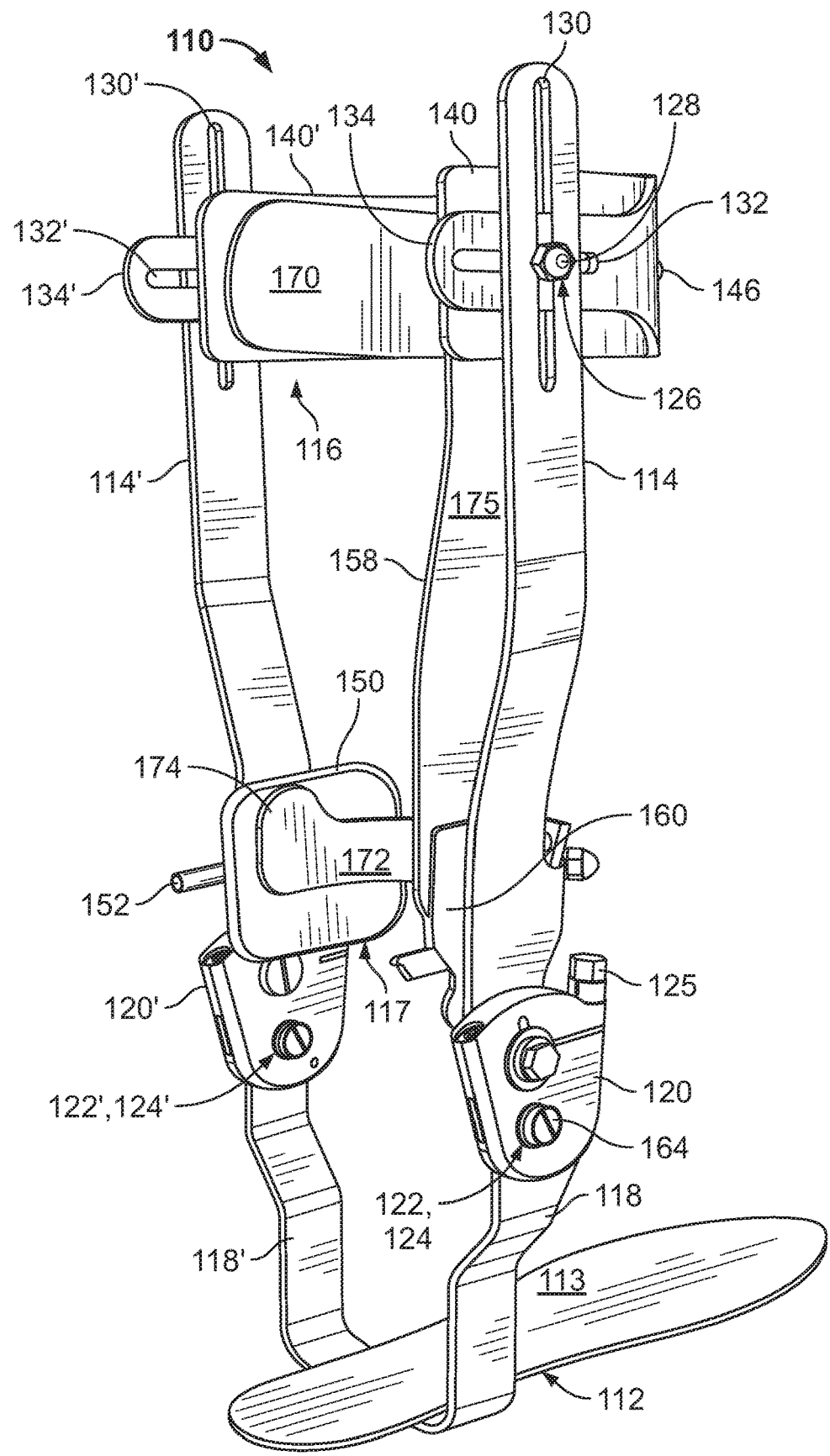
FIG. 6 is a right-rear perspective view of the rehabilitation-evaluation ankle-foot orthosis shown in FIG. 5, with the conformable composite bar precursor component positioned as when attached thereto, and a connector for receiving the conformable composite bar precursor component removed.

In addition, calf band assembly 116 further includes right and left width and coronal tilt adjustment bars 140, 140. Adjustment bars 140, 140' are slidingly received in a pair of angled bar slots 142, 142' formed in a central bar 144 and connected to central bar 144 by a width adjustment bolt 146 retained in a respective pin slot 148, 148' formed in central bar 144. These connections permit a left width adjustment (LWA) 412 and right width adjustment (RWA) 414 (each of which incidentally includes an anteroposterior component, whose magnitude is greater the more a calf band transverse bend angle θ differs from 90°, as shown in FIG. 5, and therefore should be adjusted before performing independent anteroposterior adjustment 410), as well as respective left and right coronal tilt adjustments 416 and 418 (each of which incidentally includes a sagittal tilt component and affects a width clearance for the corresponding portion of a wearer's lower extremity and, therefore, should be adjusted concurrently with respective left and right width adjustments 412 and 414 and before sagittal tilt adjustment 408). Because left and right calf band width adjustments 412 and 414 are independent, they permit not only adjusting the width clearance for a wearer's leg, but also the mediolateral position of that clearance over foot plate 113. Advantageously, adjusting the mediolateral position at which the wearer's leg is retained by calf band assembly 116 can allow a clinician to control an upper supportive force associated with coronal three-point bending for resisting hindfoot inversion or eversion, corresponding to an upper reaction force 502 discussed above with reference to FIGS. 2A-2B. However, the freedom to adjust mediolateral leg position over foot plate 113 at calf band assembly 116 in this manner is limited by hard-stop constraints on LWA and RWA adjustment ranges of motion, resulting in less freedom to adjust the mediolateral position of the width clearance as the width clearance approaches its widest and narrowest extremes. This limitation is overcome by an independent mediolateral calf band adjustment mechanism of a third REAFO to be described further below.

A suitable retention strap (not shown), analogous to retention strap 36, may be attached to calf band assembly 116 and configured to attach behind a wearer's lower leg to adjustably retain calf band central bar 144 and right and left adjustment bars 140, 140' with desired tightness to the front and mediolateral sides of an upper portion of a wearer's lower leg.

Supramalleolar Support Adjustment

As noted above, tibial shanks 114, 114' are joined by a supramalleolar cross bar 115, In addition to augmenting the stiffness of orthosis 110 and promoting conformity between left and right tibial shank angle adjustments 404, supramalleolar cross bar 115 provides an adjustable mount for a solid supramalleolar support 117 configured to urge a portion of the wearer's lower leg above the ankle in a medial or lateral direction. Supramalleolar support 117 comprises a support plate 150 pivotally connected to a generally anteroposteriorly aligned clevis pin 152 permitting passive coronal tilt conformity with a supramalleolar medial or lateral side of a wearer's lower leg. Clevis pin 152, in turn, is carried by and slidingly connected to cross bar 115 by a sliding connection including a mediolateral supramalleolar support adjustment pin 154 retained in a respective right or left (lateral or medial) pin slot 156, 156'. As shown in FIGS. 5-9F, adjustment pin 154 is retained in left pin slot 156'. Preferably, supramalleolar support 117 is symmetrical about its horizontal midplane to permit attachment of support 117 alternatively at slot 156 by flipping support 117 vertically. This provides for a linear supramalleolar support mediolateral adjustment (SMSMA) 420. It will be appreciated that mediolateral adjustment SMSMA may include a significant incidental anteroposterior component, but that this need not significantly affect the rehabilitative/evaluative function of support plate 150 at any mediolateral adjustment position, provided that support plate 150 has a sufficient anteroposterior length, generally uniform height, and generally flat shape generally aligned parallel to the sagittal plane.

Alternatively, a plate or pad of a supramalleolar support can translate on a mounting rod or bracket in the anteroposterior direction. This sliding action permits adjustment of the pad to the midline of the leg and facilitates shaping of the pad to the best fit radius of the leg, thereby increasing the total contact area of the pad to the leg and decreasing the focal pressure applied to the leg. In addition, the pad may swivel in the coronal plane about the attachment rod, facilitating self-leveling of the pad (analogous to the passive coronal tilt conformity of support plate 150 described above) to the coronal contour of the leg. This swivel may provide a lockable orientation, such that after the pad has 'found' the contour of the leg through fitting, the orientation and anteroposterior position of the pad may be locked. Optionally, the orientation and/or anteroposterior position of the pad may also be metered by a suitable scale or scales, indicating the position and orientation of the pad with respect to the REO frame, for the purpose of quantifying the shape of the feature for translation into the definitive shape of the orthosis.

Support plate 150 contributes a central supporting force to resist hindfoot inversion and/or eversion, which is the counterpart to a central reaction force 500 from a wearer's lower leg in coronal plane three-point bending support, as discussed above with reference to FIGS. 2A, 2B. In orthosis 110, an upper supporting force similarly corresponding to upper reaction force 502 is supplied by the elongate side bar 134, 134' of calf band 116 that is contralateral to the supramalleolar support supplying the central supporting force, while a lower supporting force is supplied by a lower rounded portion of the contralateral stirrup shank 118, 118' and/or an adjacent area of foot plate 113.

Conformable Composite Bar Precursor Attachment

Figure 9A:
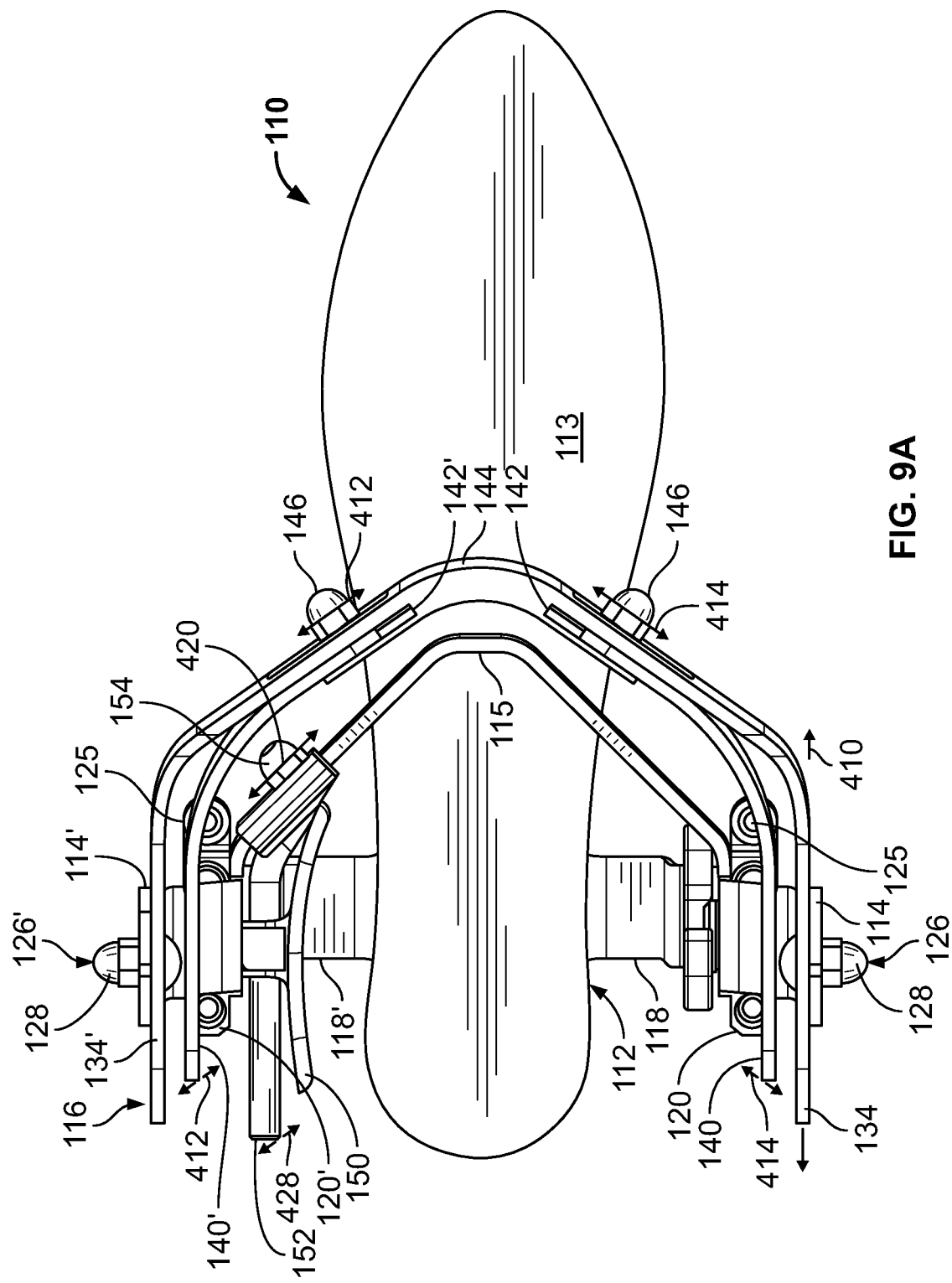
FIG. 9A is a top plan view of the rehabilitation-evaluation ankle-foot orthosis as shown in FIG. 7.
Figure 9B:
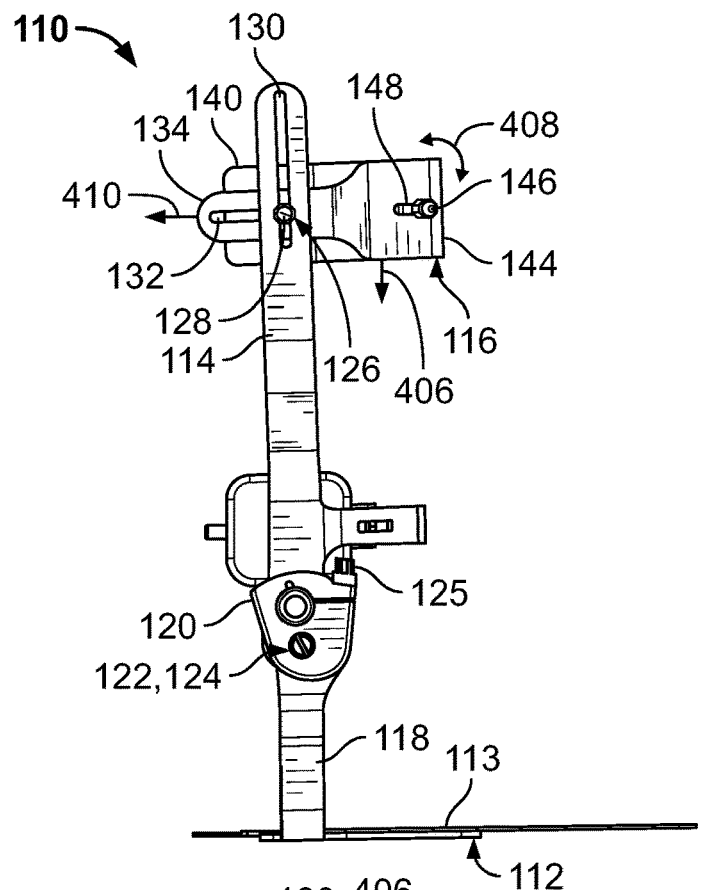
FIG. 9B is a right side elevation view of the rehabilitation-evaluation ankle-foot orthosis shown in FIG. 5 with the conformable composite bar precursor component removed.
Figure 9C:
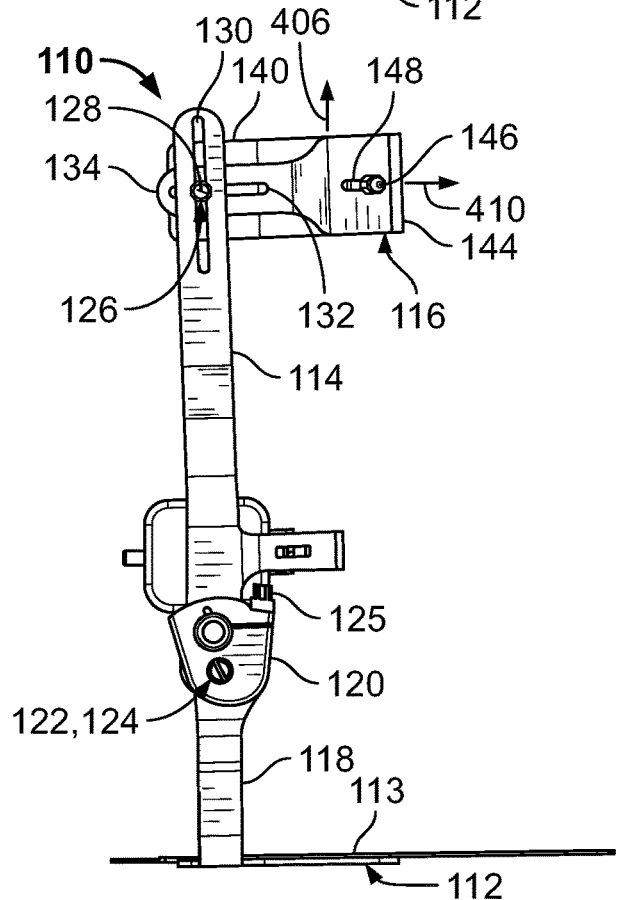
FIG. 9C is a right side elevation view of the rehabilitation-evaluation ankle-foot orthosis as shown in FIG. 9B, with a calf-band component in a higher and forward-adjusted position relative to its position shown in FIG. 9B.
Figure 9D:
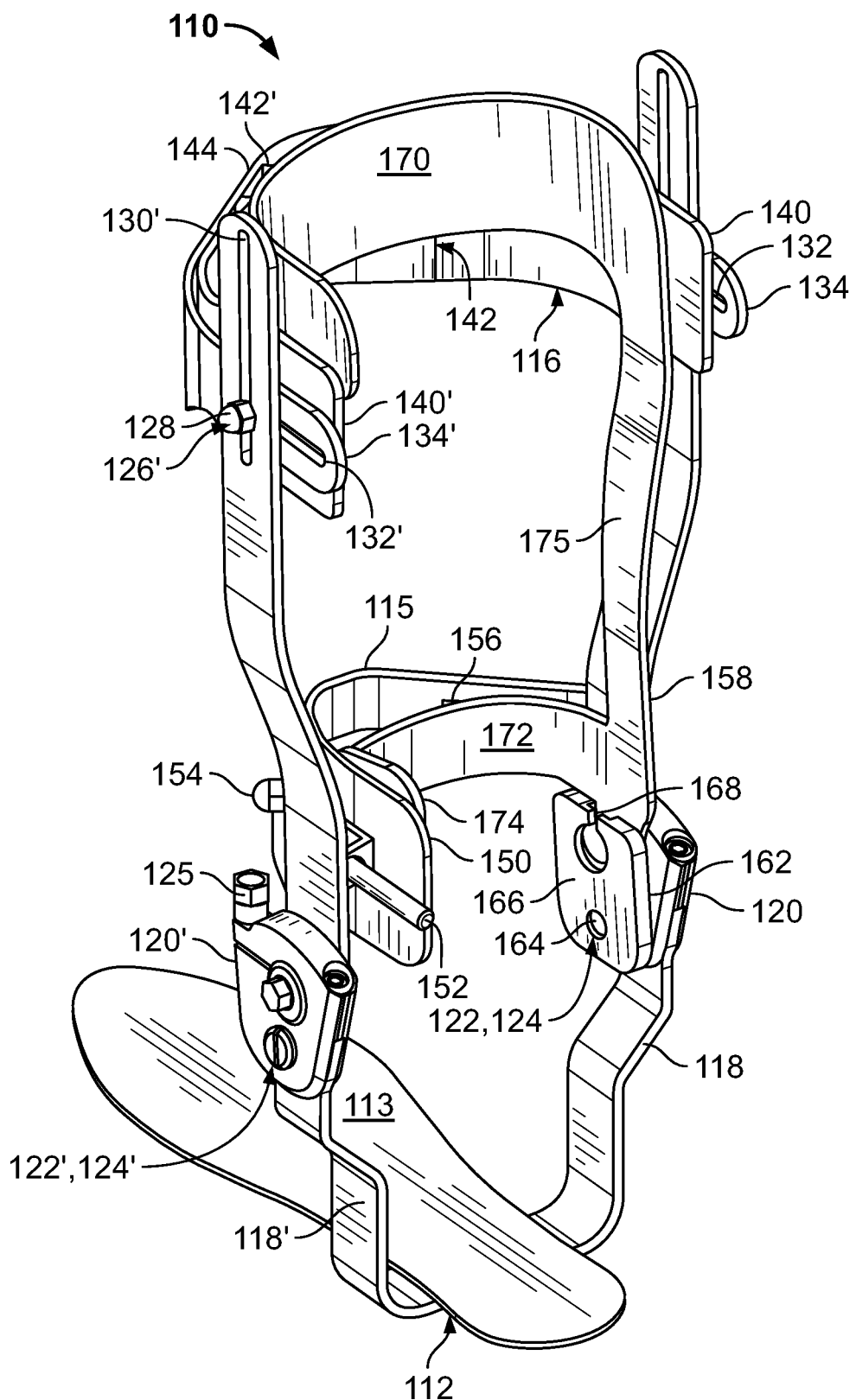
FIG. 9D is a left-rear perspective view of the rehabilitation-evaluation ankle-foot orthosis shown in FIG. 5, with the conformable composite bar precursor component positioned for attachment in a receiver component ready to be tightened to secure the conformable composite bar precursor component.
Figure 9E:
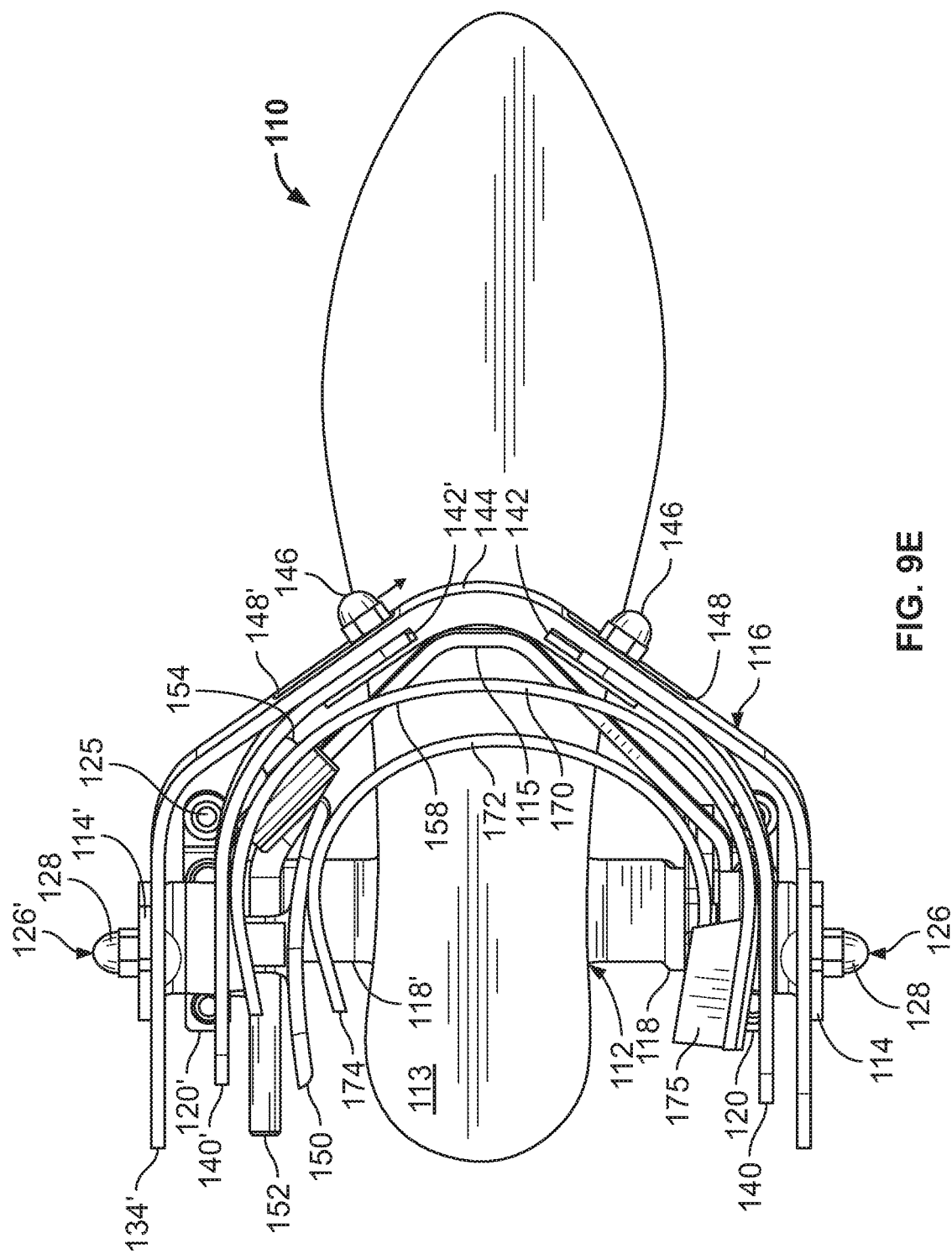
FIG. 9E is a top plan view of the rehabilitation-evaluation ankle-foot orthosis as shown in FIG. 7.
Figure 9F:
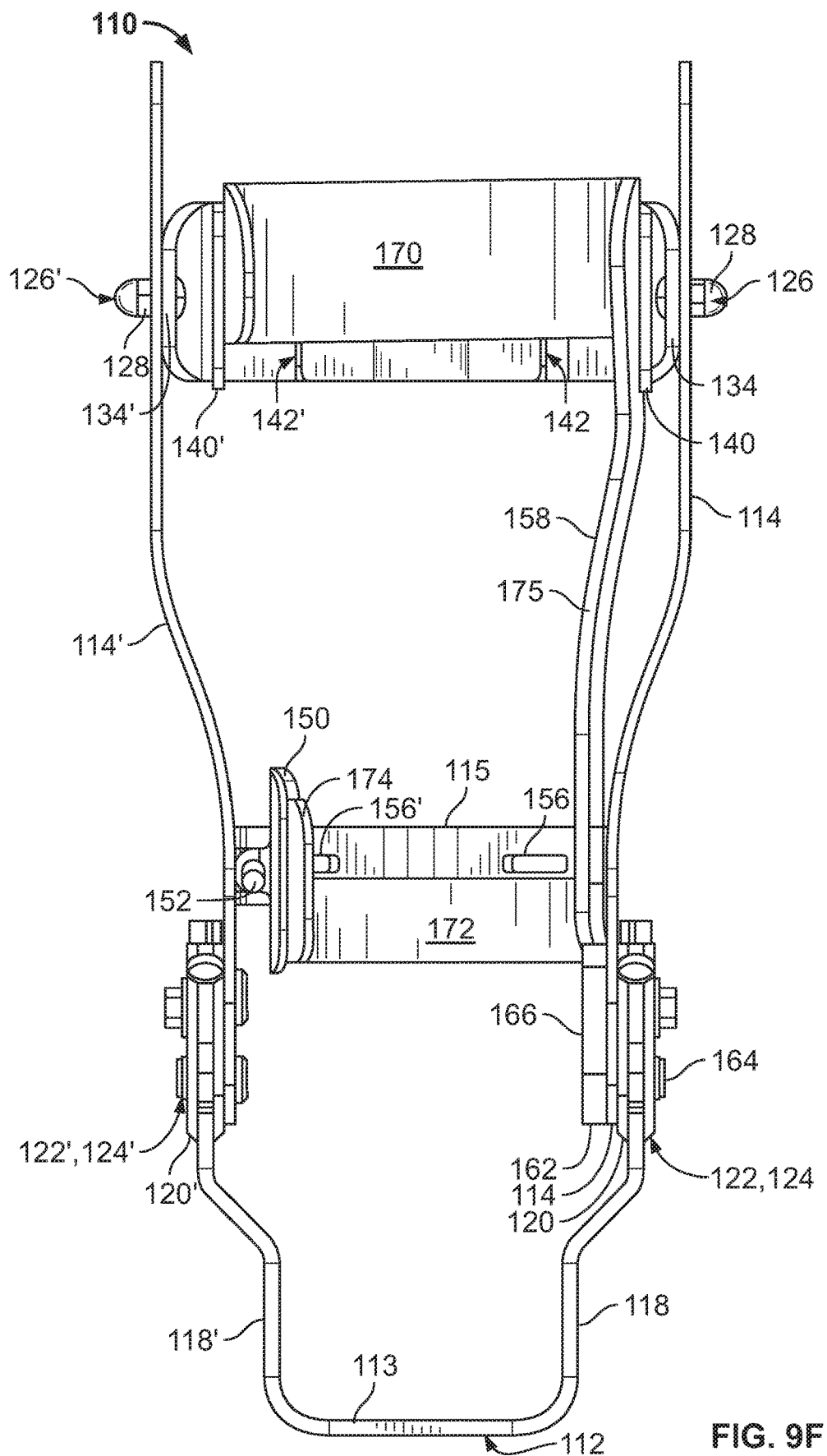
FIG. 9F is a rear elevation view of the rehabilitation-evaluation ankle-foot orthosis as shown in FIG. 7.

With reference to FIGS. 5 and 9D, a single-upright conformable composite bar precursor 158 may be connected to orthosis 110 by inserting a puzzle piece adapter 160 of precursor 158 into a corresponding puzzle piece receiver 162 carried by an appropriate one of joint components 120, 120' (illustrated as joint component 120) at a leg-facing inner side of the corresponding tibial shank 114, 114'. Puzzle piece receiver 162 may be pivotally supported by a joint component pin/bolt 164 of joint component 120, 120' associated with active pivotal joint 122, 122' and locking pivotal alignment joint 124, 124'. Receiver 162 may be "opened" to receive puzzle piece adapter 160 by, for example, loosening pin/bolt 164 to permit separation of receiver 162 from tibial shank 114, as shown in FIG. 5. A leg-facing side 166 of receiver 162 may include a slightly overlapping lip 168 around its female receptacle to prevent mediolateral escape of receiver 162 once in position, and once pin/bolt 164 is retightened to secure receiver 162 and adapter 160 adjacent tibial shank 114, 114', and tibial shank 114, 114' adjacent joint component 120, 120, in a side-by-side-by-side arrangement best shown in the rear elevation view depicted in FIG. 9F. Receiver 162 should be constrained to rotate together with tibial shank 114, 114', such as by receiving tibial shank 114, 114' in a slot (not shown) formed in receiver 162 between adapter 160 and joint component 120, 120', or by bonding with a suitable adhesive. Various ways of joining a conformable composite bar precursor puzzle piece adapter and receiver to a tibial shank (upper bar) member of an orthosis are described in greater detail in U.S. patent application Ser. No. 15/098,489, the entire disclosure of which is hereby expressly incorporated by reference. As an alternative to the illustrated two-piece connection system, orthosis 110 may incorporate a one-piece system integrating adapter 160 and receiver 162 as a unitary body (not shown) that connects directly to joint component 120, 120' for pivotal movement about pin/bolt 164.

Conformable composite bar precursor 158 advantageously includes a calf support band 170 and a supramalleolar support band 172 carrying a supramalleolar precursor support 174, support bands 170 and 172 being joined by a single precursor upright 175 disposed opposite supramalleolar precursor support 174. Each of the adjustments associated with calf band 116 and supramalleolar support 117 of orthosis 110 may help a clinician to shape corresponding portions of precursor 158 to a wearer's leg and/or provide desirable bracing to shaped portions of precursor 158 when precursor 158 is attached to orthosis 110 during a rehabilitation/evaluation period. In addition, it will be appreciated that the compressibility and/or shape conformity of calf support band 170 to the wearer's upper fibula region will prevent uncomfortable pressure in this region, generally obviating the need for the interposition of a cushion integral to orthosis 110 or, as in the first REAFO device embodiment, a separate pad.

Embodiment: Third REAFO

A third configurable rehabilitation-evaluation ankle-foot orthosis, embodying aspects of the present invention, is described in this section as rehabilitation-evaluation ankle-foot orthosis 210 ("orthosis 210") and illustrated in FIGS. 1, 10-13, and 15-23. This embodiment is a highly configurable rehabilitation and evaluation orthosis, which may be used for the purpose of establishing candidacy for orthotic treatment, as well as to determine a specific functional type of orthosis, such as an ankle functional type, which is most advantageous for the candidate. An ankle functional type of orthosis may or may not include an actively articulating ankle component. Other optional ankle-type orthosis features may include a non-articulated, posterior spring and/or a specific angle of the ankle in the AFO.

Support Sections

Orthosis 210 includes four principal interconnected support sections, each of which is adjustable in at least one dimension with respect to each neighboring section. These four sections are a foot plate/stirrup assembly 212, a right tibial shank assembly 214 and left tibial shank assembly 214', a calf band assembly 216, and a supramalleolar support 217, as most clearly shown in FIG. 1, where only these sections are labeled.

Tibial Shank Angle Adjustment

Foot plate/stirrup assembly 212 includes a foot plate 213 and right and left stirrup shanks 218, 218' attached thereto, each pivotally connected to a respective one of tibial shank assemblies 214, 214' via a respective right or left active joint component 220, 220'. As illustrated, each active joint component 220, 220' is connected to the respective stirrup shank 218, 218' by an active pivotal joint 222, 222', through which resistive-assistive torques may be provided in dorsiflexion and plantarflexion directions in the sagittal plane. Parameters of pivotal joint 222, 222', including, for example, active angular ranges and magnitudes of dorsiflexion resistance and plantarflexion resistance torques, and any hard stop limits on angular range of motion in the sagittal plane, may be interdependently or independently adjustable. Active joint component 220, 220' may, for example, be a staged resistance joint component with highly independent parameter adjustment, such as those described in detail in U.S. patent application Ser. No. 14/738,212 and PCT Patent Application No. PCT/US2016/037010, the entire disclosures of which are hereby expressly incorporated by reference, Active joint components embodying aspects of the aforementioned applications are provided by Becker Orthopedic Appliance Company. In addition, each joint component 220, 220' is connected to the respective tibial shank assembly 214, 214' by an adjustable locking pivotal alignment joint 224, 224', lockable by a tibial shank angle alignment locking bolt 225, to provide independent neutral tibial shank angle adjustment 404 of tibial shank assembly 214, 214' relative to the respective stirrup shank 218, 218', as also described in greater detail in the above referenced applications.

In the illustrated embodiment, pivotal alignment joint 224, 224' shares an axis with active pivotal joint 222, 222', advantageously allowing a neutral angle of tibial shank assemblies 214, 214' relative to stirrup shanks 218, 218' to be adjusted while maintaining the alignment of tibial shank assemblies 214, 214' with active pivotal joint 222, 222', thus tending to maintain close sagittal plane alignment of tibial shank assemblies 214, 214' with the wearer's tibia. Alternatively, offsetting these two axes slightly (as in other embodiments of active pivotal joints disclosed in the above-referenced patent applications) may have other advantages, including that of permitting a thinner component body in which the thicknesses of a tibial shank and a stirrup shank need not overlap.

Tibial/Fibular Axis Alignment of Uprights

Alignment of the uprights, that is, stirrup shanks 218, 218' and tibial shank assemblies 214, 214', with the axis of the tibia or fibula facilitates the effective application of coronal three point loads. Strictly speaking, if supramalleolar support 217 is mounted laterally, the uprights should align with the axis of the fibula, to which pressure will be applied by supramalleolar support 217. Conversely, if supramalleolar support 217 is mounted medially, the uprights should align with the axis of the tibia. However, in practice, the tibia and fibula are generally aligned in the same orientation in the sagittal plane, such that sagittal alignment with one essentially implies sagittal alignment with the other. Such tibial/fibular axis alignment of the lateral uprights may require translation of the foot plate in the shoe, together with the insertion of a suitably sized and shaped posterior heel spacer or anterior toe padding, as needed, to retain the foot plate in its translated position, to better position a lower end of each lateral upright. Similarly, the upper end of each lateral upright may be positioned in the anteroposterior direction to align the uprights with tibial/fibular axis by performing the below-described calf-band anteroposterior adjustment 410.

Heel Width Adjustment

Instead of being fixedly attached to foot plate 213 as in previously described and illustrated embodiments, a respective horizontal bottom bar 228, 228' of each stirrup shank 218, 218' is inserted into a respective medial or lateral end of a stirrup shank slot 219 disposed below and extending mediolaterally across a width of foot plate 213. With reference to the exploded and assembled views of foot plate/stirrup assembly 212 shown in FIGS. 19 and 20, respectively, stirrup shank slot 219 houses a heel width adjustment pinion 230 that engages a respective tooth rack 232, 232' of each stirrup shank when assembly 212 is assembled, so that turning adjustment pinion 230 in a clockwise or counter-clockwise direction (viewed from below) provides for a heel width adjustment (HWA) 422, moving stirrup shanks 218, 218' apart from or toward each other, respectively, in opposite mediolateral directions, to widen or narrow a heel width clearance between them. HWA 422 may be lockable by a suitable locking mechanism (not shown), such as by frictional clamping or a normal contact stop.

HWA 422 is a significant feature of orthosis 210. For one, when a right or left heel gutter 234, 234' (optionally including a custom contoured portion 233, which may be attached, such as by adhesive or a mechanical fastener, or integrally formed therewith) is disposed over foot plate 213 where it meets a bottom end of one or both of stirrup shanks 218, 218' (typically only one, for intrinsic heel inversion or eversion), a properly adjusted heel width improves the contact of a wearer's heel on a respective heel gutter 234, 234', thereby promoting its desired function. In addition, an excessively large mediolateral spacing between stirrup shanks 218, 218' causes the sides of a wearer's shoe to be pulled apart while drawing the rear of the shoe forward, resulting in discomfort and potentially hindering therapeutic efficacy by producing unintended reaction forces transmitted through the shoe. Thus, providing a snug heel fit through HWA is beneficial.

Calf Band Anteroposterior, Sagittal Tilt, Height, Mediolateral Width, Coronal Tilt, and Mediolateral Position Adjustments Anteroposterior and sagittal tilt adjustments of calf band assembly 216 are provided as follows, Calf band assembly 216 is adjustably connected at each of its mediolateral sides to a right upper bar extension 235 and left upper bar extension 235' of the respective tibial shank assembly 214, 214' via a respective lockable calf band-upper bar joint 236, 236', comprising a locking bolt 238 and a generally horizontal anteroposterior adjustment slot 240, 240' formed in and generally aligned with a longitudinal axis of a respective elongate side bar 242, 242' of a respective right or left (outer or inner, lateral or medial) side calf band 244, 244' of calf band assembly 216, anteroposterior adjustment slot 240, 240' retaining locking bolt 238 for generally sagittal rotation and translational movements of and relative to locking bolt 238, when locking bolt 238 is loosened to permit such movements, Calf band-upper bar joints 236, 236' thus provide calf band assembly 216 two simultaneously lockable degrees of freedom relative to upper bar extensions 235, 235', namely, a calf band sagittal tilt adjustment 408 generally in the sagittal plane (calf band sagittal tilt adjustment 408 should be performed after tibial shank angle adjustment 404, as only the former can be performed without affecting the other), and a calf band anteroposterior adjustment 410 generally in a longitudinal dimension of side bars 242, 242'. Sagittal tilt adjustment 408 is registered by a protractor scale 245 disposed around locking bolt 238 and anteroposterior adjustment 410 is registered by a linear scale 247 disposed along anteroposterior adjustment slot 240, 240'.

Height adjustment of calf band assembly 216 is provided as follows. Also, each upper bar extension 235, 235' is connected to the respective joint component 220, 220' via a respective right or left upper bar component adapter 246, 246' and a right or left upper bar component 248, 248' connected between the respective upper bar component adapter 246, 246' and the respective joint component 220, 220'. Upper bar extension 235, 235' is slidingly connected to upper bar component adapter 246, 246' via an upper bar height adjustment locking bolt 250 retained in a generally vertical longitudinal slot 252 formed in upper bar component adapter 246, 246'. This effects a calf band height adjustment 406, as calf band assembly 216 is carried by upper bar extensions 235, 235'.

Figure 10:
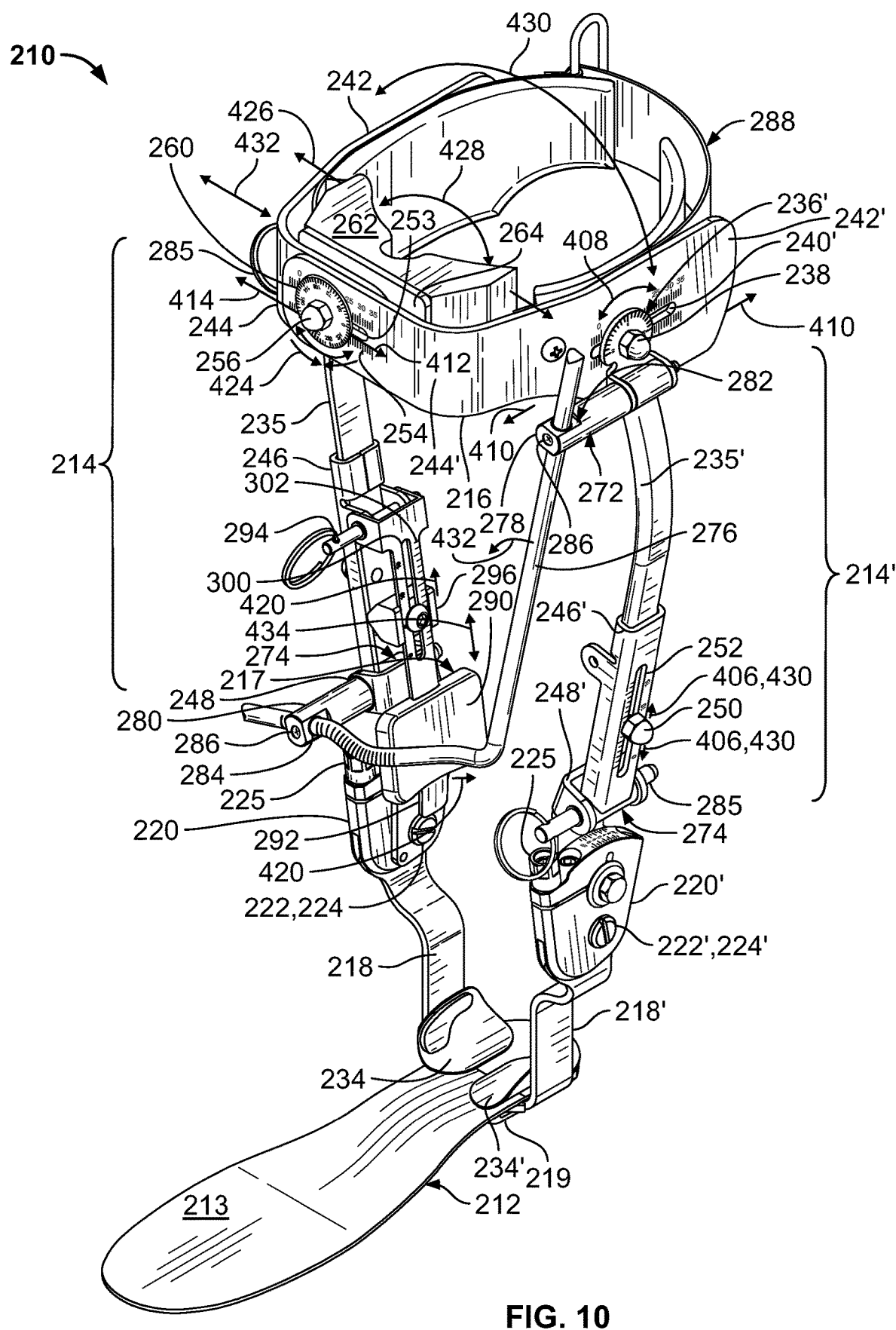
FIG. 10 is a front-left perspective view of the rehabilitation-evaluation ankle-foot orthosis shown in FIG. 1, with more detailed labeling.
Figure 11:
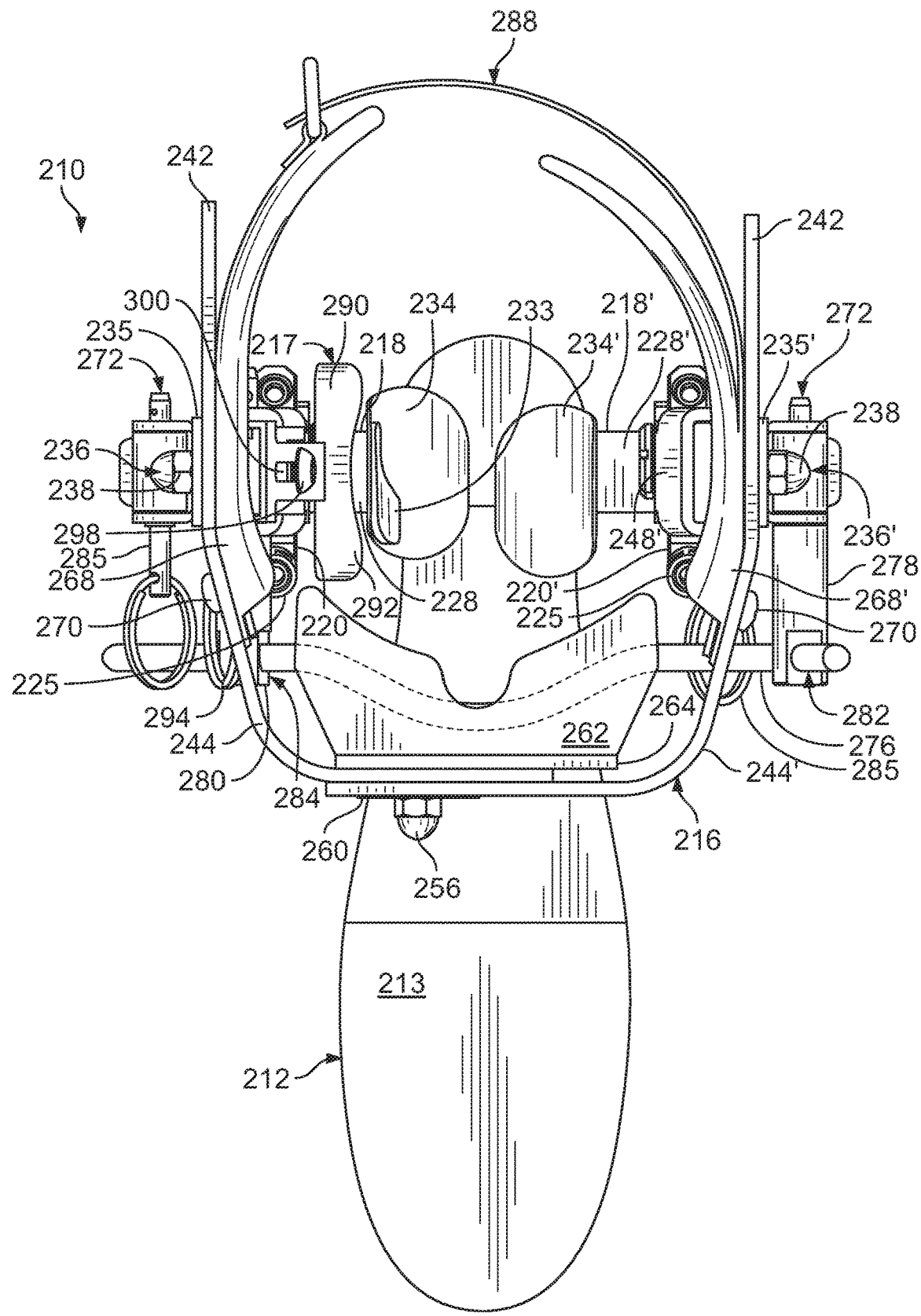
FIG. 11 is a top plan view of the rehabilitation-evaluation ankle-foot orthosis shown in FIG. 10.
Figure 21:
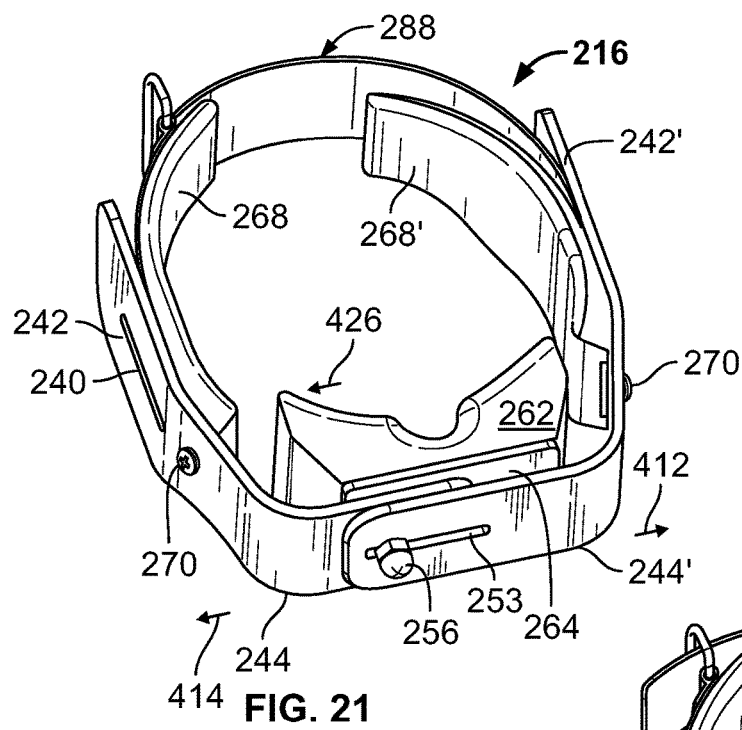
FIG. 21 is perspective view of the calf band assembly of FIG. 15, shown in an assembled configuration.
Figure 22:
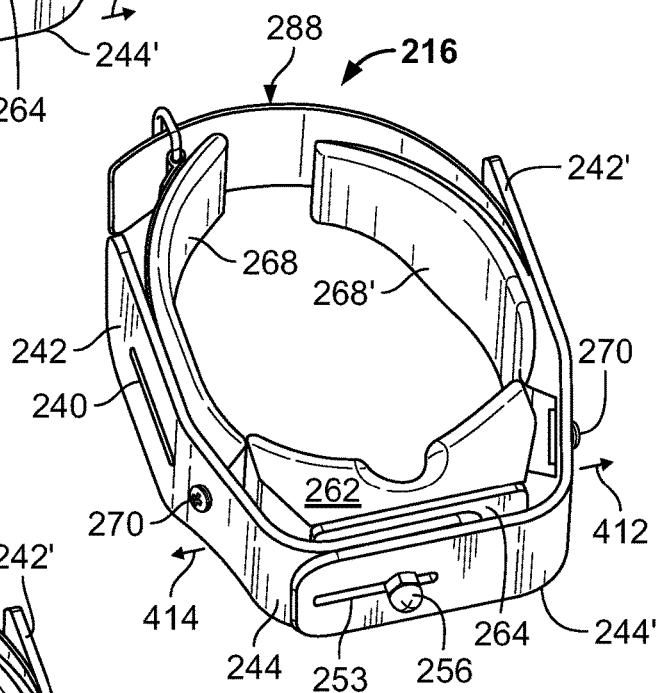
FIG. 22 is a perspective view of the calf band assembly as in FIG. 21, with a narrowing width adjustment.

Mediolateral width and internal coronal angle (or "coronal profile") adjustments of calf band assembly 216 are provided as follows. Right and left side calf bands 244, 244' are connected to permit independent adjustments of mediolateral position and coronal tilt of each with respect to the other. In particular, with reference to the exploded assembly views shown in FIGS. 15-18, one side calf band 244, 244' (shown as left side calf band 244', though the reverse is also possible) has a slot 253 formed therein and includes a linear scale 254 disposed along slot 253 for registering a relative mediolateral position of the other side calf band 244, 244' (from which a clearance width for receiving a wearer's leg may be determined), while the other side calf band 244, 244' carries a locking adjustment bolt 256 in a selected one of a plurality (three shown) of discrete mediolateral range of motion selection holes 258, each permitting a different range of right and left mediolateral width adjustments RWA, LWA of side calf bands 244, 244' when adjustment bolt 256 is mounted in the respective hole 258 and retained in slot 253. Mediolateral width adjustments 412 and 414 are further illustrated in FIGS. 21 and 22, depicting different width configurations of a separate calf band assembly 216. As shown in FIG. 10, a protractor scale 260 is carried by the side calf band 244, 244' that carries bolt 256 and registers internal coronal angle/coronal profile adjustments (ICAA) 424 of side calf bands 244, 244'. It will be appreciated that any coronal pivotal rotation of one of side calf bands 244, 244' about bolt 256 will produce an opposite coronal pivotal rotation of the other, as indicated by the pair of double arrows at 424 in FIGS. 10, 12, and 14, so as to fold the shape of calf band assembly 216 to a "V" shape, which may point generally upwardly or downwardly, having a characteristic internal coronal angle (not shown). Such folding of calf band assembly 216 to an internal coronal angle different from 180° would necessarily draw the upper ends of tibial shank assemblies 214, 214' closer together, and thus would require some flexing of those assemblies. ICAA thus meets with greater resistance the greater the internal coronal angle differs from 180°, assuming, that is, that tibial shank assemblies are generally relaxed (free of any internal bending stresses) when the internal coronal angle is 180°.

Figure 23:
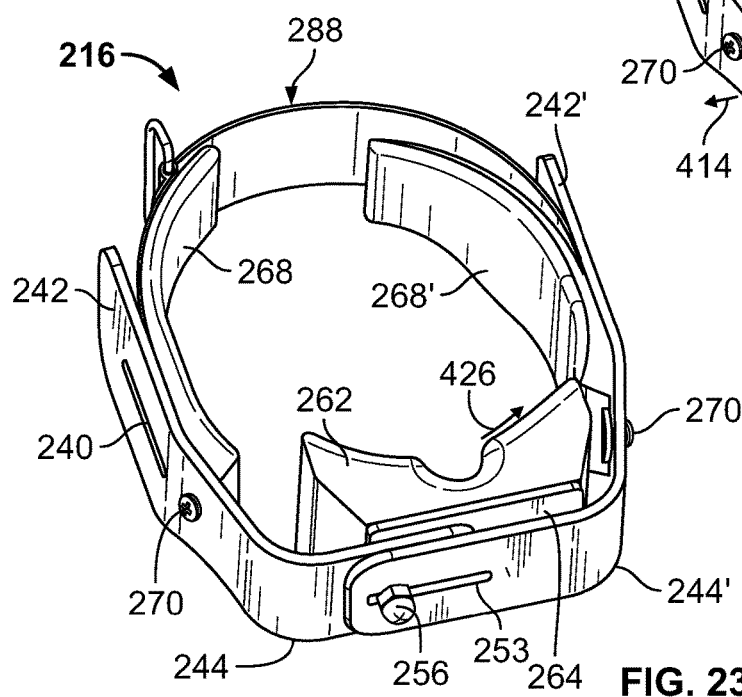
FIG. 23 is a perspective view of the calf band assembly as in FIG. 21, with a pretibial pad shifted left of center.

Pretibial pad mediolateral and coronal tilt adjustment independent of calf band mediolateral width and relative coronal tilt adjustments is also provided as follows. A pretibial pad 262 of calf band assembly 216 is adhered to a pretibial pad attachment plate 264 including a pretibial pad mediolateral adjustment slot 266 that also retains adjustment bolt 256. This permits a mediolateral pad adjustment 426 of pretibial pad 262, as illustrated in FIGS. 21 and 23, as well as coronal tilt pad adjustment 428 as indicated in FIG. 10. Additional padding of calf band assembly 216 is provided by right and left lateral pads 268, 268' fixedly attached to respective side calf bands 244, 244' by respective screws 270.

In addition, calf band assembly 216 as a whole is permitted to pivot in the coronal plane relative to each tibial shank assembly 214, 214' by a respective upper coronal pivot joint 272 disposed below the respective calf band-upper bar joint 236, 236'. Thus, it will be appreciated that a coronal tilt adjustment (CTA) 430 of entire calf band assembly 216, as indicated in FIG. 10 is inherently effected by raising or lowering one upper bar extension 235, 235' without equally raising or lowering the other upper bar extension 235, 235'.

Finally, a substantially independent calf band assembly mediolateral position adjustment is provided as follows. In addition to upper coronal pivot joints 272 connecting each tibial shank assembly 214, 214' to calf band assembly 216, a pair of lower coronal pivot joints 274 is also provided to connect each upper bar component adapter 246, 246' to its respective upper bar component 248, 248'. This forms an approximate parallelogram four-bar frame linkage composed of: (1) and (2) tibial shank assemblies 214, 214'; (3) calf band assembly 216, and (4) the combination of stirrup/foot plate assembly 212, joint components 220, 220', and upper bar components 248, 248', acting as a single fourth link. Thus, calf band assembly 216 remains approximately parallel as the linkage articulates, resulting primarily in a mediolateral (or "sway") adjustment (MLA) 432 of calf band assembly 216, with at most relatively minor vertical displacement and little or no coronal plane tilting thereof over a typical range of angles. Undesired vertical downward displacement accompanying a desired mediolateral adjustment of calf band assembly 216 away from its top dead center position can be corrected for by a height adjustment 406 at bolt 250, provided the latter has not reached its upper limit.

A sway bar 276 is connected between an upper coronal pivot clevis pin 278 of one of upper coronal pivot joints 272 and a lower coronal pivot clevis pin 280 of the contralateral lower coronal pivot joint 274. Sway bar 276 is slidingly received through a transverse hole 282 in upper clevis pin 278 and a transverse hole 284 in lower clevis pin 280. The other upper coronal pivot joint 272 and lower coronal pivot joint 274 are supported by cotter pins 285, which function equivalently to clevis pins 278, 280 aside from not being configured to receive ends of a sway bar.

An axially oriented set screw 286 is provided sunk into an end of each respective coronal pivot pin 278, 280, to selectively lock the position of sway bar 276 relative to its respective transverse hole 282, 284. Sway bar 276 is compelled to slide relative to at least one of transverse holes 282 and 284 when the parallelogram linkage of orthosis 210 is articulated. As such, a mediolateral adjustment of calf band assembly 216 can be made by loosening either or both of set screws 286, and the adjustment can then be locked by tightening both set screws 286.

From the foregoing, it will be appreciated that it may be convenient to provide a more permanent attachment of sway bar 276 to one of clevis pins 278, 280, such as by screwing a threaded end (not shown) of sway bar 276 into a tapped transverse hole (not shown) of one clevis pin, or even forming sway bar 276 and one of clevis pins 278, 280 as a single member, although the latter option could reduce the interchangeability of the resulting sway bar for use in different applications, as well as making it less compact to store. On the other hand, many combinations of suitable locking mechanisms and kinematic constraints for a single member or linkage connected between opposite corners of a four-bar parallelogram linkage composed of the structural support members of an orthosis, for indexing adjustment or selective freeing and locking of free articulation thereof, are possible within the scope of the present invention. As but one example, a sway bar similar in shape to sway bar 276, but composed of two separate segments with opposite threads joined by a turnbuckle, could permit fine adjustments by adjusting the length of the sway bar with the turnbuckle, without unlocking the ends of the sway bar. This may be particularly desirable when adjusting a device that a patient is wearing.

Calf band assembly 216 further includes a retention strap system 288 configured to attach behind a wearer's lower leg to adjustably retain pretibial pad 262 and right and left lateral pads 268, 268' with desired tightness to the front and mediolateral sides of an upper portion of a wearer's lower leg.

Supramalleolar Support Adjustment

Figure 12:
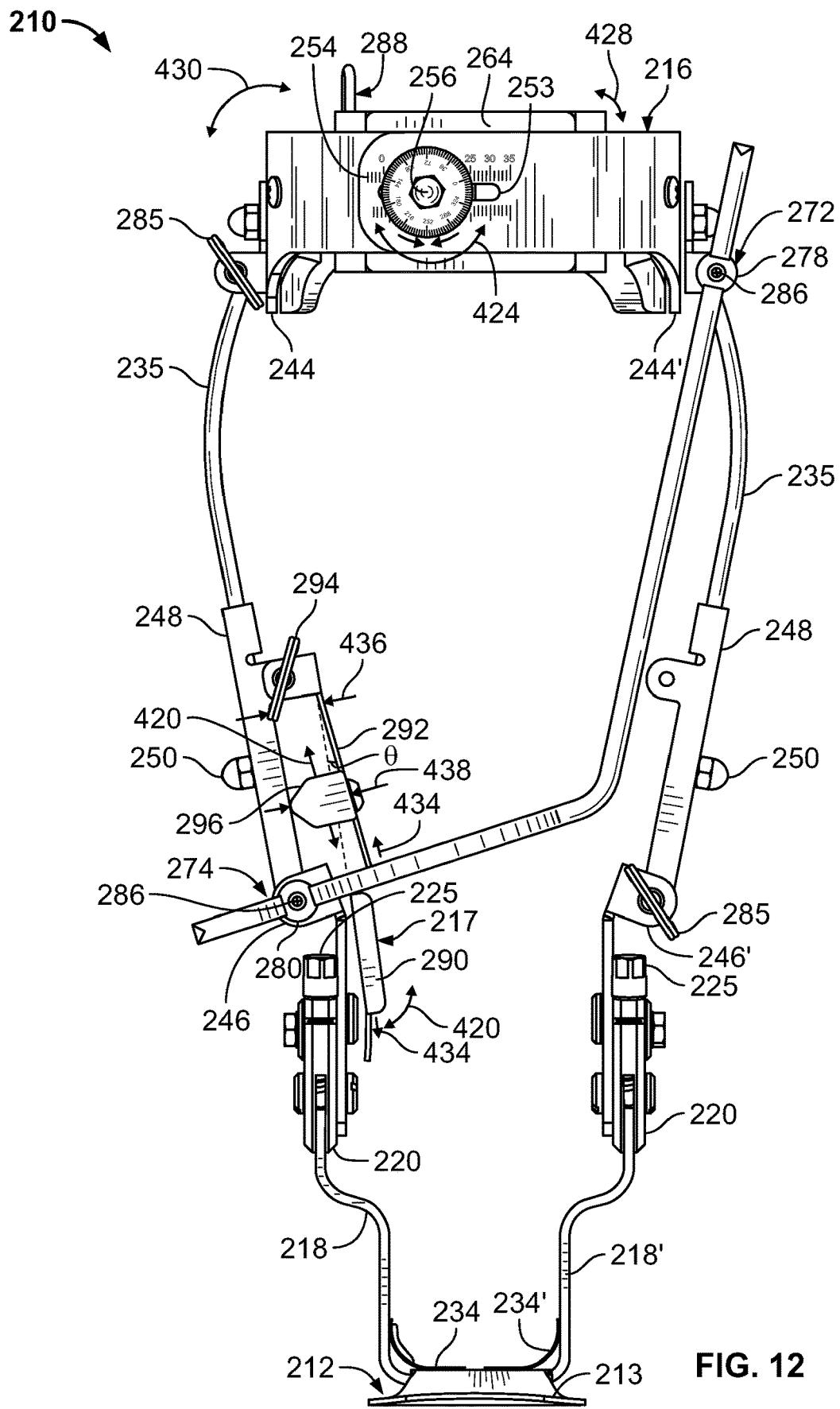
FIG. 12 is a front elevation view of the rehabilitation-evaluation ankle-foot orthosis shown in FIG. 10.
Figure 13:
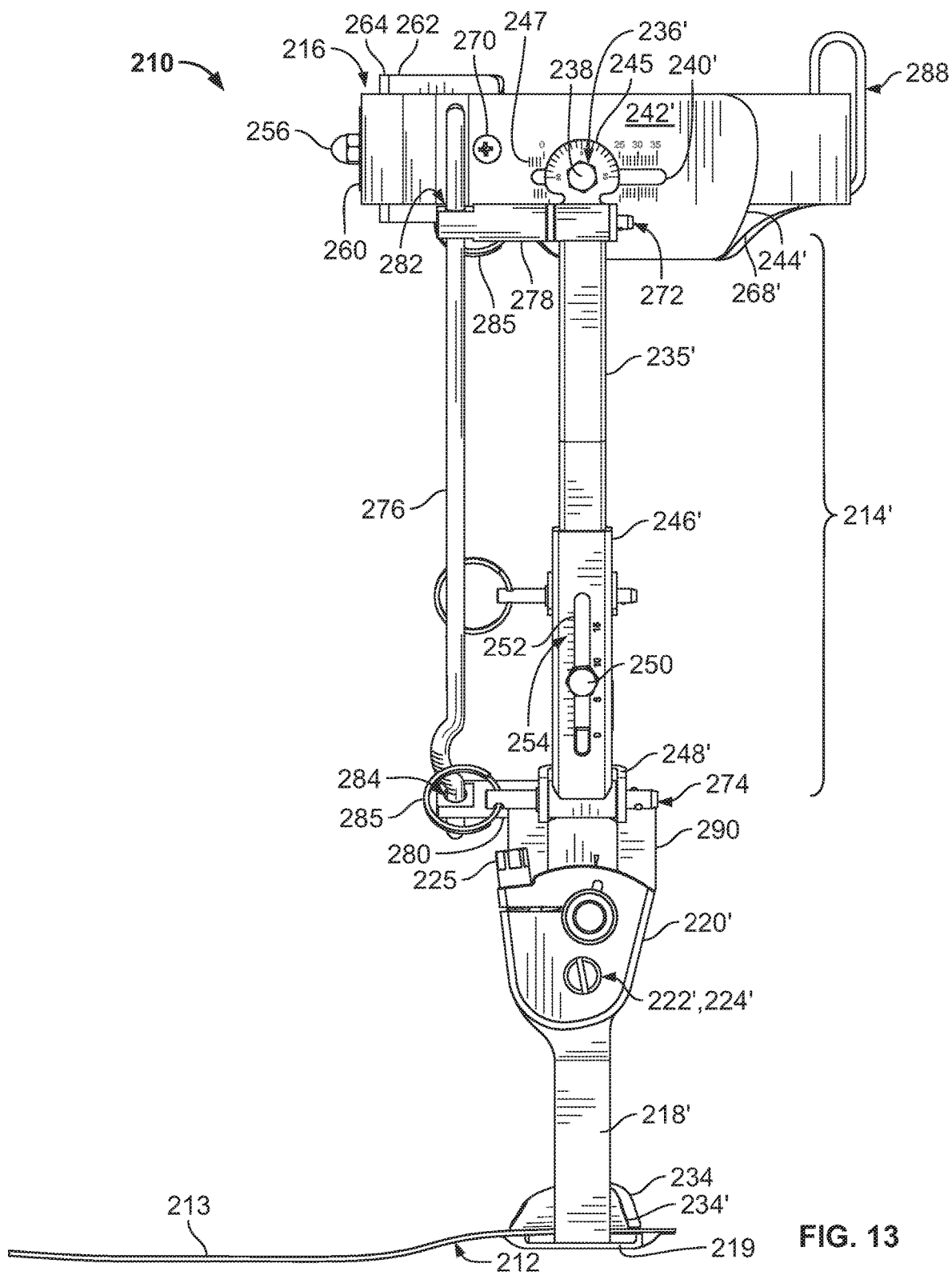
FIG. 13 is a left-side elevation view of the rehabilitation-evaluation ankle-foot orthosis shown in FIG. 10.

Supramalleolar support 217 comprises a supramalleolar pad 290 carried by and slidingly connected to a supramalleolar pad mount 292, to effect a supramalleolar support height adjustment SMSHA, as indicated in FIGS. 10, 12. Pad mount 292 is in turn configured to be carried by and pivotally connected to either of upper bar component adapters 246, 246' by a cotter pin 294 as shown in FIG. 10, for free pivoting in a coronal plane to effect approximate SMSMA 420. In addition, as best seen in FIGS. 10 and 12, supramalleolar pad mount 292 carries a slider 296 by a supramalleolar support mediolateral adjustment bolt 298 in an adjustment slot 300 with a linear adjustment scale 302 disposed thereon to register SMSMA 420, as depicted in FIGS. 10 and 12. Adjustment of SMSMA 420 is effected by cam action of slider 296 against a leg-facing side of upper bar component adapter 246, 246' and/or upper bar extension 235, 235'. In particular, a gap width 436 between pad mount 292 and adapter 246, 246'/upper bar extension 235, 235' proximate to pin 294 is less than a width 438 of slider 296 disposed in the gap, so that moving slider 296 upwardly towards pin 294 forces an angle $\theta$ between pad mount 292 and adapter 246, 246'/upper bar extension 235, 235' to increase, thus moving supramalleolar pad 290 in a tangential direction that is approximately mediolaterally inward (i.e., toward or against a wearer's leg above the ankle), while moving slider 296 downwardly away from pin 294 has the opposite effect.

Embodiment: Fourth REAFO

Figure 14:
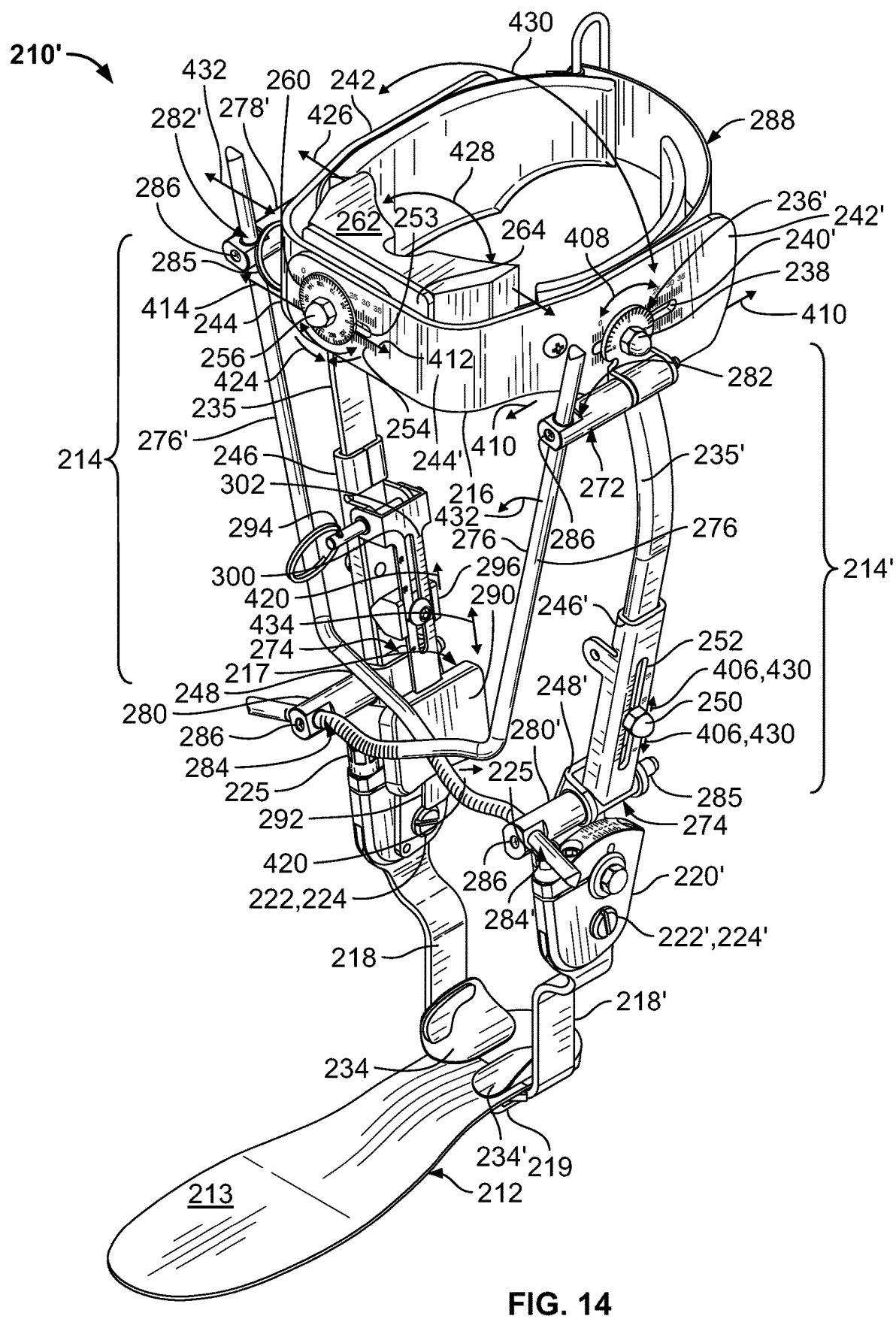
FIG. 14 is a front-left perspective view of a variation of the rehabilitation-evaluation ankle-foot orthosis shown in FIG. 10 including a second sway-bar component, according to another embodiment.
Figure 19:
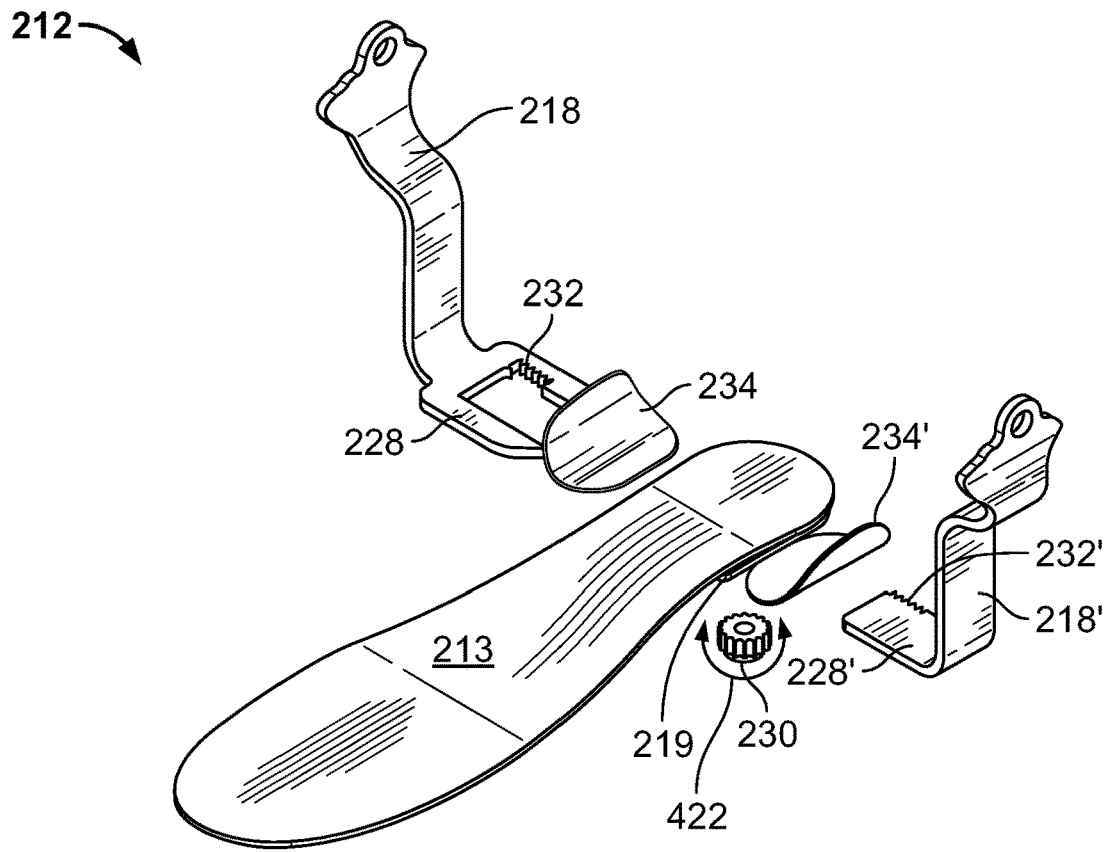
FIG. 19 is an exploded front-left perspective view of a foot plate-stirrup assembly of the rehabilitation-evaluation ankle-foot orthosis shown in FIG. 10.
Figure 20:
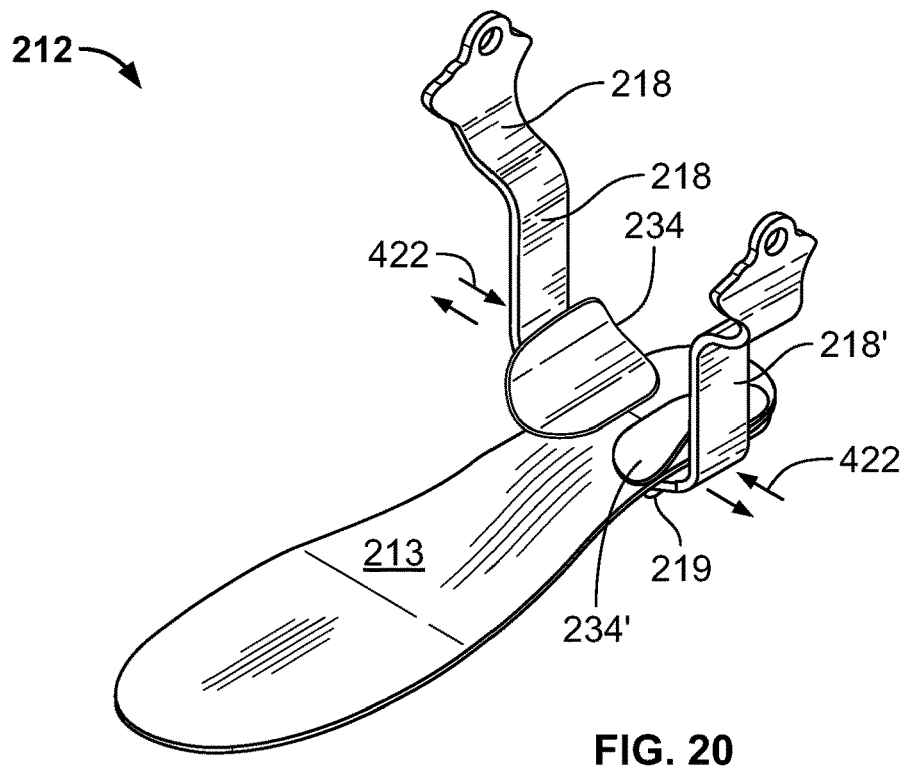
FIG. 20 is an assembled front-left perspective view of the foot plate-stirrup assembly shown in FIG. 19.

A fourth configurable rehabilitation-evaluation ankle-foot orthosis, embodying aspects of the present invention, is described in this section as rehabilitation-evaluation ankle-foot orthosis 210' ("orthosis 210'") and illustrated in FIG. 14. Orthosis 210' is nearly identical to orthosis 210, but further includes a second sway bar 276', connected between the upper coronal pivot joint 272 and opposite lower coronal pivot joint 274 that are not connected to sway bar 276. Upper and lower ends of sway bar 276' are received by coronal pivot clevis pins 278' and 280' through respective transverse holes 282' and 284' formed therein, each lockable by a respective set screw 286, in the same manner as for sway bar 276. The remaining components of orthosis 210' correspond to identical components of orthosis 210 and are designated in FIG. 14 by like reference numerals as in FIG. 10, depicting orthosis 210.

One advantage of providing a second sway bar 276' is that two sway bars 276, 276', provided that both are locked, promote greater stiffness of the parallelogram linkage formed by the four principal support component sections of orthosis 210'. It will also be appreciated that both sway bars 276, 276' must be unlocked from at least one clevis pin to permit parallelogram articulation for calf band assembly mediolateral adjustment. Height adjustment 406 of the entire calf band assembly 216 also requires unlocking both sway bars 276, 276'. However, calf band assembly coronal tilt adjustment 430, corresponding to a height adjustment 406 of only one upper bar extension 235, 235', only requires unlocking the sway bar 276 or 276' whose upper end connects to the clevis pin 278 or 278' of the respective upper bar extension 235, 235'.

Embodiments: Methods of Use of REO, Methods of Making Definitive Orthosis, Definitive Orthosis Methods of using an REO in rehabilitative and evaluative initial treatment, methods of using an REO to make a definitive orthosis, and definitive orthoses themselves, in accordance with aspects of the invention, will now be described. Included are a discussion of general REO methods and definitive orthoses, as well as specific examples of an illustrated REAFO method and definitive AFO and a stroke rehabilitation program.

General REO Methods

In addition to providing immediate rehabilitative therapeutic benefits, an REO device, which may, for example, be an REAFO device such as orthosis 10, 110, 210, or 210' as described above, is also a useful tool for evaluating the potential therapeutic benefits of longer term orthotic intervention, as well as for manufacturing a definitive orthosis. Adaptive or therapeutic benefits, lack thereof, or benefits interpreted as suboptimal and suggesting need for parametric adjustments, observed during the use of an REO in a rehabilitation/evaluation period, may inform whether a longer term definitive custom orthosis should be prescribed, and if so, what form it should take. Further, an REO in accordance with the invention may physically assist with the design of a definitive orthosis in various manners.

For instance, the REO may facilitate the direct-forming of the orthosis to the patient's limb using a conformable composite bar precursor ("CBar precursor" or conformable composite precursor/"CCP"). A CCP comprises a precursor member that is plastically conformable by hand to fit the anatomy and/or therapeutic needs of a particular patient, which, once conformed to the desired shape, may then be cured to retain the desired shape, thus forming a part of the definitive orthosis, which may be termed a "CBar", "CBar member", or "CBar component". CCPs and methods of making and using them, including various ways of temporarily connecting a CCP to a REAFO and of permanently affixing a CCP in a definitive AFO, are described in detail in U.S. patent application Ser. No. 15/098,489, the entire disclosure of which is hereby expressly incorporated by reference. Use of the REO in this process may take the form of attaching a portion of the CCP to an REO worn by the patient to anchor the CCP in proximity to the patient's limb, freeing the clinician's hands for shaping critical regions of the CCP, keeping already shaped regions in their desired positions relative to the patient's limb while shaping other critical regions. Also, or alternatively, adjustable features of the REO may be adjusted to press against corresponding regions of the CCP to clamp or retain the regions of the CCP in position between the REO features and portions of the wearer's limb with which the CCP regions functionally interact. In addition to bracing the CCP to simulate the greater stiffness that it will take on once cured, the stability provided by contact with the adjustable REO features may further assist the clinician in shaping other CCP regions without affecting shapes of regions already formed, or their relative positions.

The REO and the shaped CCP are then worn by the patient during the design process. The REO, carrying the shaped CCP, then serves as a means to evaluate the effectiveness of the orthotic design prior to curing of the CCP to complete fabrication of the definitive orthosis. It may be determined, for example, that the patient would not benefit from a definitive orthosis, that adjustment of one or more parameters implemented and measured/registered using the REO should be made and immediately applied to the definitive orthosis design, or that the evaluation period should be repeated with the aforementioned adjustment of one or more parameters, followed by reassessing whether to proceed directly with a definitive orthosis incorporating the adjusted parameter(s), proceed directly with a further adjusted definitive orthosis, further adjust parameters and repeat evaluation again, or terminate orthotic evaluation and treatment. Finally, the REO serves as a means to transfer optimized mechanical characteristics to the definitive orthosis having been fabricated from the CCP. These characteristics may include characteristics independent of the shape of the CCP or CBar member, such as adjustable active joint parameters (a neutral angle or position, active range(s) of motion, pre-load force(s) or torque(s)); the inclusion or exclusion of static foot plate features such as heel gutters, wedges, and/or various types of arch supports; or the selection of a solid, non-articulated brace type or a leaf spring element brace type for the definitive orthosis. The REO may also serve as a morphometric device for defining and functionally evaluating the shape and overall design of an orthosis fabricated using an alternative method such as 3D printing or fabrication by conventional vacuum thermoforming processes. For example, the REO may be used to determine shape, stiffness and alignment parameters, and these parameters may be conveyed to a CAD/CAM system, or directly to a configurable positive model apparatus (such as shape data receiver apparatus 304, described below). The conveyed parameters may be used to facilitate definitive orthotic fabrication by conventional/traditional means, such as thermoforming or lamination, and/or may serve as a model for contouring of the CCP.

Thus, methods according to the invention facilitate the design (affixing and shaping a CCP to the REO), evaluation (observing outcomes and adjusting parameters as appropriate), and functional and therapeutic validation of an orthotic design prior to fabrication.

The REO device must be highly configurable and adjustable to fit a variety of patients and conditions as a therapeutic aid for the purpose of design and validation. The device may also be used as a rehabilitation device in the form of a prefabricated, temporary orthosis for early mobilization of patients following a trauma, cerebrovascular accident (CVA) or other pathologic/traumatic event. As an evaluation tool, the device is used to determine candidacy of the patient for definitive orthotic treatment and to determine the best configuration and mechanical characteristics to treat the patient. The customized configuration, relative shape and position of orthotic supportive elements and mechanical characteristics of the evaluation orthosis can then be transferred to a definitive design by metering or translating the shape of the evaluation orthosis to the definitive orthosis by a variety of means. For example, morphometric features of the device may provide data to a CAD/CAM manufacturing system such as a model carver or 3D printer for fabrication of a definitive orthosis.

Figure 25:
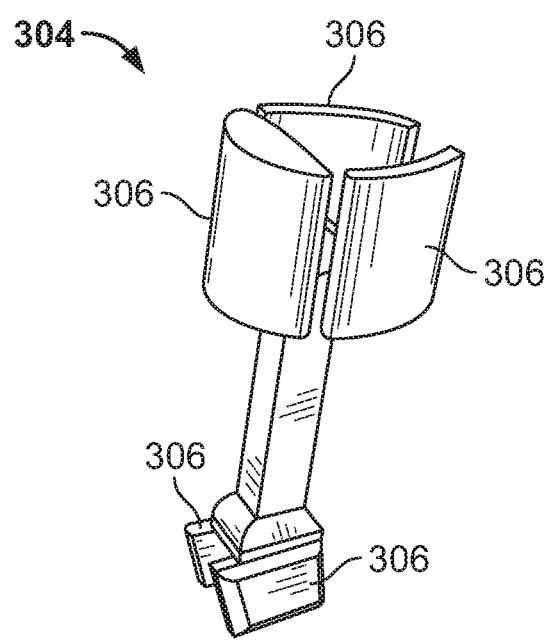
FIG. 25 is a perspective approximate representation of a shape-receiver apparatus over which components for a definitive orthosis may be formed using CBar or conventional custom orthosis manufacturing materials and methods.

The transfer of data from the device to the CAD/CAM system could be by a technician reading measurements from scales on the REO and manually entering the measurements into the CAD/CAM system, or in another embodiment, suitable adjustment sensors (not shown) may be employed in the REO to detect and measure parameter adjustments, and a suitable communication device (not shown) may remotely transmit those adjustments to the CAD/CAM system. In another embodiment, a system for manufacturing a definitive orthosis may further include an electromechanical shape data receiver apparatus, such as an AFO receiver apparatus 304, depicted by the conceptual graphic shown in FIG. 25. Receiver apparatus 304 includes a plurality of adjustable features 306, which are directed to adjust their positions and/or shapes in response to receiver apparatus 304 receiving a measurement data transmission from a remotely located, sensor-equipped REAFO. An orthotist/technician then may use receiver apparatus 304 as a positive mold, shaping a CCP (not shown) around receiver device 304 and curing the shaped CCP to form a definitive orthosis component. Alternatively, the optimized shape and mechanical characteristics may be transferred to a CBar precursor by utilizing the REO device to mechanically control the shape of the CCP, such as by adjusting REO parameters so that REO features press against portions of the CCP in the manner described above.

Many benefits of REO devices and methods according to the invention will be appreciated, including:

Rapid deployment of a reusable, customizable orthosis as an aid for therapeutic intervention;

Determination of the candidacy of a patient for orthotic intervention;

Determination of efficacy of orthotic treatment prior to creating a definitive orthotic design;

Design of an orthosis and functional, load-bearing evaluation of the design prior to fabrication;

Validation of the orthotic design and therapeutic benefit prior to fabrication; and Direct transfer of the evaluated design to the definitive orthosis.

Approach to orthotic treatment according to the invention may find application in the acute, sub-acute and chronic phases of patient rehabilitation for patients who have experienced stroke, traumatic brain injury, spinal cord injury or who were born with cerebral palsy or other pathologic neuromuscular conditions. The device and method described herein have been developed for the leg, but the device and method could conceptually be extended to the upper extremity or the spine.

As the patient progresses through the phases of recovery, their condition may change. The patient's response to therapy may be suggestive of their continuing need for orthotic support. For those patients with moderate to severe disability, an orthotic evaluation tool may help to determine the relative benefit for continued orthotic intervention. The evaluation of the orthotic influence of a prefabricated lower extremity orthosis is, however, not readily suggestive of the benefit and influence of a custom orthosis. The biomechanical coupling of the foot and ankle is complex and an uncoordinated neuromotor response to the orthotic stimulus is often difficult to anticipate.

The use of the device and method may also help to demonstrate a long-term need for bracing using a customized orthosis. For example, the American Heart Association (AHA) guidelines for stroke intervention state that "proper timing for using an orthosis can facilitate gait training and should be considered early on in the rehabilitation process to permit gait training to occur as early as possible . . . . Prefabricated orthoses can be used in the early stages of gait training, but a custom-fit device should be provided if it is determined that the patient may require long-term use of the orthosis."

In the acute and sub-acute phases of stroke rehabilitation and treatment, it is often necessary to fit orthoses on a very short time frame to help facilitate early mobilization of the patient. It may be initially unclear what therapeutic aids will be most effective and helpful to the rehabilitation process. Often, the path to recovery for the patient is unclear and results in changes in the patient's condition and therapeutic needs.

The AHA guideline regarding the use of orthoses for stroke rehabilitation is suggestive of a general summary to describe favorable attributes of an orthotic device and method used for rehabilitative care.

Orthoses should be available on a short time frame, early in the acute phase of rehabilitation. Proper timing of the provision of orthotic care can help facilitate early gait training.

REAFO Methods and Definitive Orthosis

The present invention also includes specific methods of using REAFO devices, such as orthoses 10, 110, 210, and 210' as described above. As an example, a method of using orthosis 110 will now be described in detail.

REAFO Method Using Orthosis with Integrated Plastically Deformable Precursor

First, orthosis 110 is adjusted to receive a patient's lower leg. As depicted in FIG. 9A, this adjustment includes retracting mediolateral support at calf band 116 and supramalleolar support 117. That is, left width adjustment 412 and right width adjustment 414 are made in the outward directions indicated, and supramalleolar support adjustment SMSA is also made in the outward (leftward) direction. Next, the patient dons orthosis 110 and anteroposterior adjustment 410 is made to position the front of calf band 116 proximate to a front side of the patient's lower leg. The height of calf band 116 is then adjusted (height adjustment 406) to below the fibula neck of the patient's leg. Conformable composite precursor 158 is installed by inserting puzzle piece adapter 160 into receiver 162 and then securing the sagittal pivotal connection of receiver 162 to joint component 120 about bolt 164. To be clear, it will be appreciated that installation of precursor 158 or an analogous precursor does not apply to a method of using the illustrated embodiments of orthoses 10, 210, or 210'. In those embodiments, a CCP may instead be shaped to a positive conformable model. Shape parameters of the positive conformable model may be adjusted to match corresponding shape parameters of the REO, either automatically through a telecommunicative link, or by human observation of REO parameters followed by direct adjustment of model parameters to match the human-observed REO parameters.

With precursor 158 installed, the patient again dons orthosis 110, and mediolateral adjustments 412 and 414 are made, drawing respective left and right calf band width adjustment bars 140, 140' inwardly toward the patient's leg so that calf support band 170 of precursor 158 contacts the patient's leg in quiet standing. The patient's weight is then shifted off of orthosis 110, and the mediolateral position of supramalleolar support 117 is then adjusted (SMSMA) to draw supramalleolar precursor support 174 to a position optimally resisting inversion or eversion of the patient's ankle.

Having thus conformed the shape of precursor 158 to properly fit the patient's lower leg, a functional assessment is then performed to optimize mechanical parameters of orthosis 110. In particular, neutral tibial shank alignment, resistive torques, active ranges of motion, and/or a recruitment angle of a late-stage spring component of joint component 120 are adjusted, and readjusted as appropriate in view of patient observations, to optimize sagittal support. Additional supramalleolar support adjustments may also be made based on observations of the patient bearing weight on and walking with orthosis 110 in place, with the effect of further modifying the shape of precursor 158.

The patient may continue to wear orthosis 110 during an extended rehabilitation period, or a single-visit evaluation may result in either a determination not to prescribe a definitive orthosis or a completed design of a definitive orthosis. When it has been determined that a definitive orthosis will benefit the patient, precursor 158 is removed from orthosis 110, cured, and incorporated as a permanent component of a definitive orthosis.

Although precursor 158 is depicted as a single-upright precursor, a similar double-upright precursor (not shown) could be configured for attachment to an orthosis similar to orthosis 110 with a second puzzle piece receiver 162 (not shown) fitted to the other joint component 120, by including a second upright portion continuing downwardly from calf support band 170 opposite upright 175. Supramalleolar precursor support 174 would remain free from the second upright to facilitate its inward displacement by adjustment of supramalleolar support 117 or its counterpart. It may be unnecessary to shape or form the second upright of such a precursor, as the presence of supramalleolar precursor support 174 or its equivalent would likely constrain the patient's leg to contact only one of the uprights in the precursor and in a definitive orthosis made therefrom, but including a second upright may facilitate the manufacture of the definitive AFO from the cured precursor.

Alternatively, a prefabricated second upright, analogous to tibial shanks 114, 114', may be incorporated into a definitive orthosis (not shown). According to still another alternative method, a two-upright precursor (not shown) may be attached using two corresponding puzzle piece adapters and receivers, with the upright on the side where supramalleolar support is to be provided including a shorter variation of supramalleolar support band 172, appropriately sized and shaped to wrap around an adjustable supramalleolar support feature of the REAFO (analogous to support plate 150) and to conform its position to that of the adjustable REAFO feature, instead of wrapping around an entire front or rear side of the patient's lower leg. Such a CBar precursor, shaped in this manner, could be cured after removing from the REAFO, and then incorporated into a definitive double-upright orthosis by appropriate methods described herein and/or in U.S. patent application Ser. No. 15/098,489, the entire disclosure of which is hereby expressly incorporated by reference.

Single-Upright REAFO

In other variations within the scope of the invention, an REAFO itself may be a single-upright REAFO (not shown), and may be used to facilitate manufacture of a single- or double-upright definitive orthosis, according to similar methods to those described above. The single upright of the REAFO may be a lateral-side upright, rear-side upright (which may, for example, attach at a single point or contiguous region behind a heel region of a foot plate, or may comprise diverging attachment legs that attach at two or more mediolateral side attachment points or regions), or front-side upright (which may, for example, attach at a single point or contiguous region in front of a toe region of a foot plate, or may comprise diverging attachment legs that attach at two or more mediolateral side attachment points or regions).

REAFO Method Using Orthosis with Sway Bar

A fitting procedure, therapeutic intervention, and orthotic design method using orthosis 210 or orthosis 210' will now be described.

Fitting Procedure

It will be understood that the fitting and adjustment procedure now to be described is a starting point, intended to approximate a best shape and function for orthosis 210, 210'. Iterative adjustments will typically be necessary to find optimal support. This method will utilize both objective and subjective clinical feedback and will be based upon the clinician's experience and manner of clinical practice. According to the method, orthosis 210, 210' is first adjusted or prepared to receive a patient's lower leg. Thus, stirrup shanks 218, 218' are relatively retracted to widen a heel receiving space between them, and one or both side calf bands 244, 244' are retracted to widen a calf clearance between them. Sway bar(s) 276 (and, if included, 276') are released, such as by loosening set screw(s) 286.

One or more heel gutters 234, 234', if to be included, are selected and installed. If the patient exhibits a calcaneal neutral or varus foot type, a smooth medial and lateral gutter are selected. For a calcaneal valgus foot posture, a smooth lateral gutter and medial sustentaculum support gutter are selected. Supramalleolar support 217 is then installed by connecting it to the appropriate left or right upper bar component adapter 246, 246'. That is, if the patient's hindfoot is valgus, supramalleolar support 217 is connected to the upper bar component adapter 246, 246' located at the medial side. If the patient's hindfoot is varus, supramalleolar support 217 is instead installed at the lateral side upper bar component adapter 246, 246'. Once installed, supramalleolar support 217 is also retracted to make room for the patient's lower leg, by moving slider 296 downward.

Then, the REAFO is donned to the patient's limb, initially without bearing the patient's weight. Mediolateral HWA is performed on stirrup shanks 218, 218' to contact the patient's medial and lateral heel sides in non-weight bearing posture. Next, a patient's shoe is donned over stirrup-foot plate assembly 212 to secure foot plate 213 to the patient's limb.

With reference to FIGS. 10, 12, and 14, several initial calf band adjustments are then performed, including height adjustment 406, anteroposterior adjustment 410, right and left mediolateral width adjustments 414 and 412, coronal tilt adjustment 430, internal coronal angle/coronal profile adjustment ICAA 424. Then, with the patient standing, the mediolateral "sway" adjustment 432 of calf band 216 is performed, to accommodate the coronal posture of the patient's lower limb, followed by re-locking sway bar(s) 276, 276'.

Supramalleolar support 217 is then adjusted in quiet standing, and through a functional evaluation process, to optimize its contribution to the support of the patient's ankle, knee, and hip. These adjustments include SMSMA 420 (performed by moving slider 296 up to move pad 290 mediolaterally against the patient's leg or down to retract it) and height adjustment (SMSHA) 434, performed by sliding pad 290 up and down on pad mount 292.

Finally, using the adjustment features of joint components 220, 220', sagittal resistance and neutral alignment (designated tibial shank angle adjustment 404 in FIG. 4A) thereof are adjusted to optimize active ankle joint support function in the sagittal plane.

Therapeutic Intervention

In a therapeutic intervention; an REAFO such as orthosis 210, 210', thus fitted, is worn by the patient during a rehabilitation-evaluation period. During this period, the REAFO is used to provide stability for body weight support, to administer acute or subacute rehabilitation, and/or to establish patient candidacy for definitive orthotic treatment.

Orthotic Design

According to an orthotic design method, an REAFO such as orthosis 210, 210' is used to determine a functional type of orthosis best suited to the patient's supportive needs. The efficacy and fitting adjustments of the various components of the REAFO will help determine whether to include certain componentry in a definitive orthosis, as well as facilitating the design of the components selected for inclusion, including the optimal shape of the definitive orthosis and its supportive elements, and the tuning of its active joint components, if any.

For the purpose of this evaluation, shape and stiffness characteristics of an REAFO will be similar to those characteristics of the definitive orthosis. For example, the rigidity of the lateral bars (i.e., of the stirrup shanks 218, 218' and tibial shank assemblies 214, 214', collectively constituting the lateral structural uprights of orthosis 210, 210') of the REAFO will approximate the rigidity of the lateral bars of the definitive orthosis. It may be necessary to interchange REAFO componentry to effectively evaluate the orthotic design with respect to these stiffness characteristics for various materials used to construct the definitive orthosis. Alternatively, an adjustable stiffness spring component may be incorporated into one or more structural components of the REAFO, for example, by dividing sway bar 276, 276' into two segments connected by a compressive spring element (not shown).

Definitive Orthosis

Figure 24:
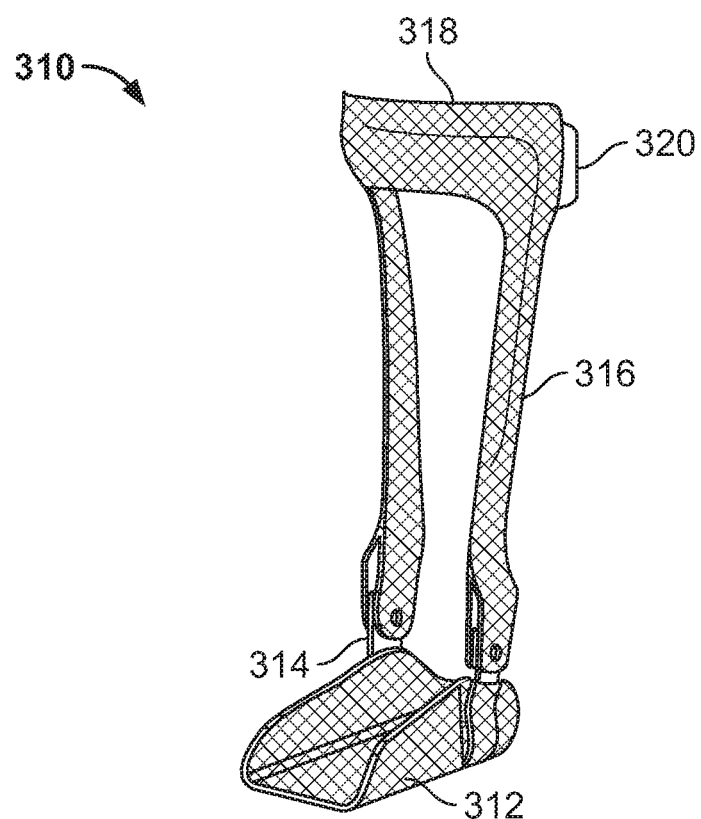
FIG. 24 is a perspective view of a definitive orthosis according to another embodiment of the invention.

A definitive ankle-foot orthosis 310, such as may be formed from a double-upright CBar precursor, without a supramalleolar precursor support, is depicted in FIG. 24. Orthosis 310 includes a lower CBar component 312 affixed to a stirrup component 314 and an upper CBar component 316, which may have been formed from a CBar precursor shaped in an REAFO according to a method analogous to that described above. Upper CBar component 316 is shown pivotally connected to stirrup component 314 for sagittal pivoting with respect to lower CBar component 312. As desired, a suitable joint component may be interposed at the pivotal connection between upper CBar component 316 and lower CBar component 312, for which an adapter may be used, such as adapter 293, as described in U.S. patent application Ser. No. 15/098,489, the entire disclosure of which is hereby expressly incorporated by reference. Upper CBar component 316 includes a calf support band 318, configured to be secured to an upper portion of a wearer's lower leg by a strap system 320.

Stroke Rehabilitation Program

Early intervention in stroke rehabilitation is believed to contribute to positive results for patients. Under early intervention, patient mobilization begins shortly after stroke while patients are still in the hospital. One useful tool for this phase of stroke recovery is the ankle foot orthosis. Ankle foot orthoses assist the rehabilitation team/therapist in mobilizing the patient early in the rehabilitation process.

Sometimes, therapists use generic ankle foot orthoses for this purpose. Some therapists, however, prefer more configurable support for their patients to assist in their early rehabilitation.

Thus, a pre-fabricated REAFO, such as one of orthoses 10, 110, 210, and 210' described above, is useful for therapeutic treatment of stroke inpatients. Preferably, the range of adjustability of the parameters of an REAFO according to the invention allows it to fit most patients while they are still in the hospital. In an embodiment, the REAFO is comprised of an adjustable metal and composite frame and ankle joints providing plantarflexion resistance and staged dorsiflexion resistance. Advantageously, the device includes features to manage foot and ankle posture as well as adjust the level of support of the ankle and knee for rehabilitation.

The REAFO is also used to evaluate the functional benefits of ankle and knee support provided by the orthosis. The ankle joints are highly adjustable and tunable for the patient's needs in the early flaccid as well as late spastic stages of stroke recovery.

Usage of the REAFO during an evaluation period helps to determine which patients would benefit from the ankle and knee support provided by a definitive ankle foot orthosis. If it is determined that the patient would benefit from a definitive ankle foot orthosis, the foot section of the REAFO may be converted to a definitive, custom composite AFO using CBar technology. A CBar precursor leg section replaces the upper section of the REO and is directly formed to the limb. By direct forming the upper CBar to the limb, the optimal elements of orthotic support may be quickly and cost effectively incorporated into the orthosis on the last day of inpatient rehabilitation. CBar technology can dramatically reduce delivery time, cost and equipment needed to produce a custom composite ankle foot orthosis for the recovering stroke patient prior to discharge from the hospital.

As the patient continues to recover as an outpatient, staged resistance ankle joints attached to the custom CBar orthosis are highly customizable to adapt to the changing needs for support of the patient. Initial orthoses should be pre-fabricated rather than custom until the patient's long-term need is determined. Orthoses, whether initial or customized, should support the ankle and knee to improve stability and gait and prevent falls. Customized orthoses should be provided only to patients who demonstrate long-term need for bracing.

Variations of the Invention

Devices and methods according to the invention may be used to treat a broad range of pathologic musculoskeletal conditions with similar requirements. A non-exclusive functional description of various devices and methods in accordance with the present invention may be summarized as follows:

1. The particular orthoses described herein are AFOs, but the device and method may be generalized to be any form of orthosis for the lower extremity, upper extremity or spine.
2. The orthosis is comprised of a frame/structure that is fabricated of metal, plastic, composite or some hybrid of metal, polymer and/or composite materials.
3. The AFO is designed to be pre-fabricated and to accommodate a wide range of limb shapes.
4. The AFO is comprised of supportive features customary in ankle foot orthoses, however these features are adjustable to meet the needs of a variety of biomechanical deficits. These adjustments may include modifying states or relative positions of elements that remain connected to the AFO. If required to translate a design into a definitive orthosis, adjustments may also include interchange of stiffness elements or spring elements simulating stiffness elements correlating to the relative stiffness/level of support of definitive orthoses of differing material type or construction, for the purpose of evaluation.
5. A highly customizable lower extremity orthosis that will fit a broad range of patient limb shapes.
6. The adjustable features comprise elements of orthotic support. These features are highly configurable to produce an optimally-supportive orthosis from the pre-fabricated frame/structure.
7. The invention encompasses an adjustable lower-extremity orthosis that may be configured to provide multi-plane direct support to the ankle, and indirect support to the knee.
8. The invention encompasses devices and methods that facilitate fitting by customary orthotic practice.
9. The invention encompasses a device that includes orthotic supportive elements including but not limited to:
   a. Sagittal ankle support to provide plantarflexion resistance and/or dorsiflexion resistance
   b. Sagittal ankle alignment adjustment
   c. Coronal ankle support in the form of three point coronal bending across the subtalar joint
   d. Accommodation for transverse plane orientation of the ankle mortise to align the mechanical axis of the AFO to that axis. Although not shown in the illustrated embodiments, this may entail, for example, a lockable rotation adjustment of the foot plate in a transverse plane relative to the positions of joint components 20/20', 120/120', 220/220', and or an active-resistance transverse-rotation joint component interposed between the foot plate and joint components 20/20', 120/120', 220/220'.
   e. Accommodation of leg shape and coronal posture of the limb f. Adjustment of calf band anteroposterior shape and supportive position as well as mediolateral shape and supportive position relative to other supportive elements of the orthosis
10. The invention encompasses a pre-fabricated lower-extremity orthosis to reduce the time frame of delivery, early in the acute phase of rehabilitation.
11. The invention encompasses a reusable pre-fabricated lower-extremity orthosis to reduce cost of care.
12. The invention encompasses an effective lower extremity orthosis that will improve the patient's stability, gait and help to prevent falls.
13. The invention encompasses an adjustable lower-extremity orthosis that may be used to determine the patient's long-term need for orthotic bracing.
14. The invention encompasses an orthotic device and method, used to evaluate the patient's need for orthotic support.
15. The invention encompasses an orthotic device and method, which translates the evaluation into a series of measurements or forms and effectively facilitates the design of a definitive lower-extremity orthosis.
16. The optimally-supportive orthosis possesses features which facilitate its use as a therapeutic aid. These features may include the following:
    a. A prefabricated rehabilitation orthosis that may be reused for multiple patients during rehabilitation.
    b. A prefabricated rehabilitation orthosis that may be dispensed quickly in the early stages of patient rehabilitation.
    c. A prefabricated rehabilitation orthosis which may be easily adjusted with configurable elements of orthotic support to suit the specific supportive needs of a multitude of patients.
    d. Configurable elements of orthotic support which provide support similar to that support inherent in a custom orthosis.
    e. Configurable elements of orthotic support which may include control of ankle stiffness, ankle range of motion, ankle position in the sagittal plane, and indirect knee support.
    f. Configurable elements of orthotic support which may include control of coronal ankle position, coronal foot position, as well as coronal and transverse plane support of the foot and ankle.
17. The invention encompasses methods of fitting and adjustment of the inventive orthosis.
18. The prefabricated rehabilitation orthosis may also be used as an evaluation tool to determine the effectiveness of orthotic support for the patient and to help determine whether the patient would benefit from long-term orthotic support.
19. The orthosis evaluation tool as configured and adjusted for the specific needs of a specific patient may be used as a measurement tool or geometrical form to create a definitive orthosis for continued rehabilitation, or long-term use by the patient.
20. The orthosis evaluation tool, used as a measurement tool, will indicate the specific form, shape, configuration and measurements of a custom orthosis for the purpose of producing a custom orthosis to reproduce the desired orthotic function.
21. The invention encompasses an REO as a device used to design and evaluate the shape, comfort, effectiveness and overall therapeutic benefit of an orthotic design prior to fabrication of the definitive orthosis.
22. The invention encompasses an REO as a device used to design and shape a Conformable Composite Precursor prior to curing the CCP to fabricate the definitive orthosis.
23. The invention encompasses an REO as a device used to determine the optimal design and shape of a lower extremity orthosis prior to fabrication of the orthosis and to measure and translate the shape and mechanical characteristics of the orthotic design to the definitive orthosis through some means of fabrication, including but not limited to a CAD/CAM manufacturing method, such as computerized numerical control (CNC) carving of an anatomical mold for customary orthotic vacuum thermoforming/fabrication, 3D printing or other method of fabrication.

Variations of the Invention

In addition to the supportive elements and combinations thereof that are described and illustrated herein, other combinations of the described supportive elements, other dimensions, ranges, or modes of adjustment thereof, as well as other supportive elements not described, whether permanent, interchangeable, or adjustable, may be advantageously incorporated into a configurable orthosis according to the invention.

More generally, while the invention has been described with respect to certain embodiments, as will be appreciated by those skilled in the art, it is to be understood that the invention is capable of numerous changes, modifications and rearrangements, and such changes, modifications and rearrangements are intended to be covered by the following claims.

What is claimed is:

1. A configurable orthosis for a user having a limb comprising a first limb segment having a lateral side, a physiological joint that articulates about at least a first physiological joint axis, and a second limb segment having a lateral side, wherein the lateral side of the user's second limb segment is adjacent said lateral side of the user's first limb segment and the second limb segment is joined to the first limb segment by the physiological joint, the orthosis comprising:

a first link configured to extend along the lateral side of the first limb segment when the orthosis is worn by the user;

a second link configured to extend along the lateral side of the second limb segment when the orthosis is worn by the user, the second link being connected to the first link proximate to the first physiological joint axis at a lateral side of the physiological joint when the orthosis is worn by the user;

a plastically deformable precursor member removably affixed to the first link, the precursor member including a first contact surface; and a first support member movably connected to the first link for movement to a fixed first support member adjustment position relative to the first link, said movement of the first support member to the first support member adjustment position configured to engage and deform the precursor member and to move said first contact surface into contact with a first contact portion of the user's first limb segment, when the orthosis is worn by the user, the first contact surface of the precursor member configured to transmit an aligning force to said first contact portion of the user's first limb segment to urge or restrain a first articulation of the user's first limb segment about the first physiological joint axis relative to the user's second limb segment.

2. A rehabilitation and evaluation orthotic treatment method using the configurable orthosis of claim 1, the method comprising
   aligning the first link at the lateral side of the patient's first limb segment and the second link at the lateral side of the patient's second limb segment;
   with the precursor member attached to the first link and the first contact surface of the precursor member positioned between the first support member and the first contact portion of the patient's first limb segment, moving the first support member to the fixed first support member adjustment position to engage and deform the precursor member to move the first contact surface of the precursor member into contact with the first contact portion of the patient's first limb segment to urge or restrain said first articulation of the user's first limb segment about the first physiological joint axis; and
   providing the orthosis including the deformed precursor member for the patient to wear during a rehabilitation and evaluation period.

3. The method of claim 2, the first support member being connected for at least two degrees of freedom of movement relative to the first link.

4. The method of claim 3, said at least two degrees of freedom of movement comprising translation in at least one direction and rotation about at least one axis independent of said translation.

5. The method of claim 4, the orthosis further comprising
   a first elongate slot formed in one of the first support member and the first link;
   a pin carried by the other of the first support member and the first link, the pin being retained in the first elongate slot to permit translation of the first support member relative to the first link along a direction aligned with a length of the first elongate slot and rotation of the first support member relative to the first link about an axis of the pin; and
   a locking mechanism configured to selectively restrain said translation and said rotation of the first support member relative to the first link.

6. The method of claim 5, the orthosis further comprising a second elongate slot formed in the other of the first support member and the first link, the pin being retained in the second elongate slot to permit translation of the first support member relative to the first link along a direction aligned with a length of the second elongate slot.

7. The method of claim 3, said at least two degrees of freedom of movement comprising independent translation in two non-parallel directions.

8. The method of claim 2 wherein the orthosis further comprises an orthotic joint component, the orthotic joint component including
   an orthotic joint connecting one of the first link and the second link for pivotal movement relative to the joint component about an orthotic joint axis approximately aligned with the first physiological joint axis when the orthosis is worn by the user;
   a biasing component configured to produce a biasing torque to urge said one of the first link and the second link to articulate relative to the joint component link in a biased pivoting direction about the orthotic joint when an angular orientation of said one of the first link and the second link relative to the joint component is within an active angular range within which the biasing component is engaged, and
   a lockable alignment joint connecting the other of the first link and the second link for pivotal movement of the other link to a lockable angular orientation relative to the joint component about an alignment joint axis parallel to the orthotic joint axis, to determine a neutral angular orientation of the first link relative to the second link toward which the biasing component biases said one of the first link and the second link.

9. The method of claim 8 wherein the users first limb segment has a contralateral side generally opposite to the lateral side of the user's first limb segment and the user's second limb segment has a contralateral side generally opposite to the lateral side of the user's second limb segment, the contralateral side of the user's second limb segment being adjacent the contralateral side of the user's first limb segment, the first contact portion of the user's first limb segment being comprised in a front side of the user's first limb segment disposed between said lateral and contralateral sides, the orthosis further comprising
   a first contralateral link aligned with the contralateral side of the user's first limb segment when the orthosis is worn by the user;
   a second contralateral link aligned with the contralateral side of the user's second limb segment when the orthosis is worn by the user;
   a contralateral orthotic joint component connected between the first link and the second link to permit pivotal movement of the first link relative to the second link about said orthotic joint axis; and
   the first support member being a lateral connecting member configured to join the first link in fixed relation to the lateral connecting member and to the first contralateral link.

10. The method of claim 9, the orthosis being an ankle-foot orthosis, the first link and first contralateral link being tibial shank components; the second link and second contralateral link being stirrup uprights, the first support member being a calf band configured to be disposed near an upper portion of the user's lower leg, and the aligning force transmitted by the first contact surface of the precursor member tending to urge the user's lower leg to pivot rearwardly in a sagittal plane to produce plantarflexion of the user's foot.

11. The method of claim 8, wherein said orthotic joint axis and said alignment joint axis are the same.

12. The method of claim 2, the orthosis further comprising
   a second support member movably connected to the first link for movement to a fixed second support member adjustment position relative to the first link;
   a second contact surface of the precursor member;
   said movement of the second support member to the second support member adjustment position configured to engage and deform the precursor member and to move said second contact surface into contact with a second contact portion of the user's first limb segment, when the orthosis is worn by the user;
   the second contact surface of the precursor member configured to transmit an aligning force to said second contact portion of the user's first limb segment to urge or restrain a second articulation of the user's first limb segment relative to the user's second limb segment.

13. The method of claim 12, said second articulation being articulation about a second physiologic joint axis.

14. The method of claim 13, said second physiologic joint axis being generally orthogonal to said first physiologic joint axis.

15. The method of claim 12, said second articulation being articulation about the first physiologic joint axis.

16. The method of claim 2, wherein the plastically deformable member is curable and the method further comprises observing the patient during the rehabilitation and evaluation period, and when said observation indicates prescribing the patient a custom orthosis:
removing the deformed precursor member from the first link;
curing the deformed precursor member to form a non-plastically deformable cured custom orthotic member configured to be worn on the patient's first limb segment with the first contact surface in contact with the first contact portion of the patient's first limb segment;
connecting the cured custom orthotic member to a second limb segment orthotic member configured to be worn on the patient's second limb segment when the cured custom orthotic member is worn on the patient's first limb segment, to form the custom orthosis; and
providing the custom orthosis to the patient.

17. The method of claim 16, further comprising, before said curing the deformed precursor member:
based on observations of the patient during the rehabilitation and evaluation period, further moving the first support member to a post-evaluation first support member adjustment position, and further deforming the precursor member to change the aligning force transmitted by the first contact surface of the precursor member to the first contact portion of the patient's first limb segment.

18. The method of claim 2, the first support member configured to be disposed at the lateral side of the user's first limb segment when the orthosis is worn by the user and the first support member being connected to the first link for lateral and contralateral movement relative to the first link, and said first contact portion being comprised in the lateral side of the user's first limb segment.

19. The orthosis of claim 1, the first support member being connected for at least two degrees of freedom of movement relative to the first link.

20. The orthosis of claim 19, said at least two degrees of freedom of movement comprising translation in at least one direction and rotation about at least one axis independent of said translation.

21. The orthosis of claim 20, further comprising
a first elongate slot formed in one of the first support member and the first link;
a pin carried by the other of the first support member and the first link, the pin being retained in the first elongate slot to permit translation of the first support member relative to the first link along a direction aligned with a length of the first elongate slot and rotation of the first support member relative to the first link about an axis of the pin; and
a locking mechanism configured to selectively restrain said translation and said rotation of the first support member relative to the first link.

22. The orthosis of claim 21, further comprising a second elongate slot formed in the other of the first support member and the first link, the pin being retained in the second elongate slot to permit translation of the first support member relative to the first link along a direction aligned with a length of the second elongate slot.

23. The orthosis of claim 19, said at least two degrees of freedom of movement comprising independent translation in two non-parallel directions.

24. The orthosis of claim 1, further comprising an orthotic joint component, the orthotic joint component including
an orthotic joint connecting one of the first link and the second link for pivotal movement relative to the joint component about an orthotic joint axis approximately aligned with the first physiological joint axis when the orthosis is worn by the user;
a biasing component configured to produce a biasing torque to urge said one of the first link and the second link to articulate relative to the joint component link in a biased pivoting direction about the orthotic joint when an angular orientation of said one of the first link and the second link relative to the joint component is within an active angular range within which the biasing component is engaged, and
a lockable alignment joint connecting the other of the first link and the second link for pivotal movement of the other link to a lockable angular orientation relative to the joint component about an alignment joint axis parallel to the orthotic joint axis, to determine a neutral angular orientation of the first link relative to the second link toward which the biasing component biases said one of the first link and the second link.

25. The orthosis of claim 24 wherein the user's first limb segment has a contralateral side generally opposite to the lateral side of the user's first limb segment and the user's second limb segment has a contralateral side generally opposite to the lateral side of the user's second limb segment, the contralateral side of the user's second limb segment being adjacent the contralateral side of the user's first limb segment, the first contact portion of the user's first limb segment being comprised in a front side of the user's first limb segment disposed between said lateral and contralateral sides, the orthosis further comprising
a first contralateral link aligned with the contralateral side of the user's first limb segment when the orthosis is worn by the user;
a second contralateral link aligned with the contralateral side of the user's second limb segment when the orthosis is worn by the user;
a contralateral orthotic joint component connected between the first link and the second link to permit pivotal movement of the first link relative to the second link about said orthotic joint axis; and
the first support member being a lateral connecting member configured to join the first link in fixed relation to the lateral connecting member and to the first contralateral link.

26. The orthosis of claim 25, the orthosis being an ankle-foot orthosis, the first link and first contralateral link being tibial shank components, the second link and second contralateral link being stirrup uprights, the first support member being a calf band configured to be disposed near an upper portion of the user's lower leg, and the aligning force transmitted by the first contact surface of the precursor member tending to urge the user's lower leg to pivot rearwardly in a sagittal plane to produce plantarflexion of the user's foot.

27. The orthosis of claim 24, wherein said orthotic joint axis and said alignment joint axis are the same.

28. The orthosis of claim 1, further comprising
a second support member movably connected to the first link for movement to a fixed second support member adjustment position relative to the first link;

a second contact surface of the precursor member;

said movement of the second support member to the second support member adjustment position configured to engage and deform the precursor member and to move said second contact surface into contact with a second contact portion of the user's first limb segment, when the orthosis is worn by the user;

the second contact surface of the precursor member configured to transmit an aligning force to said second contact portion of the user's first limb segment to urge or restrain a second articulation of the user's first limb segment relative to the user's second limb segment.

29. The orthosis of claim 28, said second articulation being articulation about a second physiologic joint axis.

30. The orthosis of claim 29, said second physiologic joint axis being generally orthogonal to said first physiologic joint axis.

31. The orthosis of claim 28, said second articulation being articulation about the first physiologic joint axis.

32. The orthosis of claim 1, the first support member configured to be disposed at the lateral side of the user's first limb segment when the orthosis is worn by the user and the first support member being connected to the first link for lateral and contralateral movement relative to the first link, and said first contact portion being comprised in the lateral side of the user's first limb segment.

33. The orthosis of claim 1, wherein the plastically deformable precursor member is curable after being deformed to a permanent deformed shape.

* * * * *